(12) United States Patent
Anderson et al.

(10) Patent No.: US 6,645,765 B1
(45) Date of Patent: Nov. 11, 2003

(54) PLANT REGULATORY SEQUENCES FOR CONTROL OF GENE EXPRESSION

(75) Inventors: Heather M. Anderson, St. Louis, MO (US); Catherine A. Chay, St. Louis, MO (US); Guilan Chen, Wildwood, MO (US); Timothy W. Conner, Wildwood, MO (US)

(73) Assignee: Monsanto Technology LLC, St. Louis, MO (US)

( * ) Notice: Subject to any disclaimer, the term of this patent is extended or adjusted under 35 U.S.C. 154(b) by 134 days.

(21) Appl. No.: 09/665,189

(22) Filed: Sep. 15, 2000

Related U.S. Application Data

(60) Provisional application No. 60/154,182, filed on Sep. 16, 1999.

(51) Int. Cl.[7] ............................ C12N 5/10; C12N 15/11; C12N 15/63
(52) U.S. Cl. ................... 435/410; 435/320.1; 536/24.1
(58) Field of Search ...................... 536/24.1; 435/320.1, 435/410

(56) References Cited

U.S. PATENT DOCUMENTS 5,925,804 A * 7/1999 Hockema et al. ........... 800/295

FOREIGN PATENT DOCUMENTS

| EP | 1 033 405 A2 | | 9/2000 |
|---|---|---|---|
| WO | WO94/01572 | * | 1/1994 |
| WO | WO 96/31609 | * | 10/1996 |
| WO | WO9640925 | | 12/1996 |
| WO | WO9943797 | | 9/1999 |

OTHER PUBLICATIONS

Bokhari–Riza et al, "Characterization of histone H2A and H2B cDNA clones isolated from maize ovule cDNA library," Maydica, p. 115–18, (Feb. 8, 1994).

* cited by examiner

*Primary Examiner*—Terry McKelvey
(74) *Attorney, Agent, or Firm*—Monsanto; Forchisha M. Davis

(57) ABSTRACT

The present invention relates to nucleic acid sequences for regulating gene expression in plants. In particular, the invention relates to 5' regulatory sequences which are useful for regulating expression of heterologous DNAs in plants and methods for identifying multiple 5' regulatory sequences which confer a particular expression profile when operably linked to DNA sequences. The invention also relates to expression vectors containing the 5' regulatory sequences and to transgenic plants containing the expression vectors.

7 Claims, 14 Drawing Sheets

SEQUENCE LISTING

<160> NUMBER OF SEQ ID NOS: 75

<210> SEQ ID NO 1
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: synthetic primer sequence

<400> SEQUENCE: 1
gtaatacgac tcactatagg gc                                          22

<210> SEQ ID NO 2
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: synthetic primer sequence

<400> SEQUENCE: 2
actatagggc acgcgtggt                                              19

<210> SEQ ID NO 3
<211> LENGTH: 31
<212> TYPE: DNA
<213> ORGANISM: Artificial Sequence
<220> FEATURE:
<221> NAME/KEY: misc_feature
<222> LOCATION: (1)..(31)
<223> OTHER INFORMATION: synthetic primer seqeunce

<400> SEQUENCE: 3
agggcaagct tggtcgacgg cccgggctgg t                                31

```
<210> SEQ ID NO 4
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: synthetic primer sequence

<400> SEQUENCE: 4
cggcagggtt tcccagtca cga                                              23

<210> SEQ ID NO 5
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: synthetic primer sequence

<400> SEQUENCE: 5
agcggataac aatttcacac agga                                            24

<210> SEQ ID NO 6
<211> LENGTH: 27
<212> TYPE: DNA
<213> ORGANISM: Artificial Sequence
<220> FEATURE:
<221> NAME/KEY: misc_feature
<222> LOCATION: (1)..(27)
<223> OTHER INFORMATION: synthetic primer sequence

<400> SEQUENCE: 6
cttgacggac cctccgctgg cgtccat                                         27

<210> SEQ ID NO 7
<211> LENGTH: 36
<212> TYPE: DNA
<213> ORGANISM: Artificial Sequence
<220> FEATURE:
<221> NAME/KEY: misc_feature
<222> LOCATION: (1)..(36)
<223> OTHER INFORMATION: synthetic primer sequence

<400> SEQUENCE: 7
tggtctagac tgctgcgact ggcgagtggg ggaaat                               36

<210> SEQ ID NO 8
<211> LENGTH: 27
<212> TYPE: DNA
<213> ORGANISM: Artificial Sequence
<220> FEATURE:
<221> NAME/KEY: misc_feature
<222> LOCATION: (1)..(27)
<223> OTHER INFORMATION: synthetic primer sequence

<400> SEQUENCE: 8
tccttaccca tggctgaagg aaaatgt                                         27

<210> SEQ ID NO 9
<211> LENGTH: 36
<212> TYPE: DNA
<213> ORGANISM: Artificial Sequence
<220> FEATURE:
<221> NAME/KEY: misc_feature
<222> LOCATION: (1)..(36)
<223> OTHER INFORMATION: synthetic primer sequence
```

```
<400> SEQUENCE: 9
tggtctagat acactgctcg tcgggcgtca gtagag                                36

<210> SEQ ID NO 10
<211> LENGTH: 27
<212> TYPE: DNA
<213> ORGANISM: Artificial Sequence
<220> FEATURE:
<221> NAME/KEY: misc_feature
<222> LOCATION: (1)..(27)
<223> OTHER INFORMATION: synthetic primer sequence

<400> SEQUENCE: 10
ggtcatgtcg aagaagacgc gagggtt                                          27

<210> SEQ ID NO 11
<211> LENGTH: 36
<212> TYPE: DNA
<213> ORGANISM: Artificial Sequence
<220> FEATURE:
<221> NAME/KEY: misc_feature
<222> LOCATION: (1)..(36)
<223> OTHER INFORMATION: synthetic primer sequence

<400> SEQUENCE: 11
tggtctagag agactgggag ctagggtttg gggata                                36

<210> SEQ ID NO 12
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: synthetic primer sequence

<400> SEQUENCE: 12
gaatgtgatc tcaaggcgct tctcatagcc                                       30

<210> SEQ ID NO 13
<211> LENGTH: 41
<212> TYPE: DNA
<213> ORGANISM: Artificial Sequence
<220> FEATURE:
<221> NAME/KEY: misc_feature
<222> LOCATION: (1)..(41)
<223> OTHER INFORMATION: synthetic primer sequence

<400> SEQUENCE: 13
aagaacagca atggtagatc ttgaatcaga acacaatgct g                          41

<210> SEQ ID NO 14
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: synthetic primer sequence

<400> SEQUENCE: 14
tatattccag tggatgcgcc gctgggtacg                                       30

<210> SEQ ID NO 15
<211> LENGTH: 41
<212> TYPE: DNA
<213> ORGANISM: Artificial Sequence
```

```
<220> FEATURE:
<221> NAME/KEY: misc_feature
<222> LOCATION: (1)..(41)
<223> OTHER INFORMATION: synthetic primer sequence

<400> SEQUENCE: 15
tgatcgtgac cgccatggta gatcttcctc cttgttatct c                41

<210> SEQ ID NO 16
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: synthetic primer sequence

<400> SEQUENCE: 16
tcgcttccct gtccctggtg cattttgagc                             30

<210> SEQ ID NO 17
<211> LENGTH: 37
<212> TYPE: DNA
<213> ORGANISM: Artificial Sequence
<220> FEATURE:
<221> NAME/KEY: misc_feature
<222> LOCATION: (1)..(37)
<223> OTHER INFORMATION: synthetic primer sequence

<400> SEQUENCE: 17
atgccgccat ggtagatctc ccctactgcg ccgaccc                     37

<210> SEQ ID NO 18
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: synthetic primer sequence

<400> SEQUENCE: 18
gcacgaacac cttcttcccc ttcagatccg                             30

<210> SEQ ID NO 19
<211> LENGTH: 39
<212> TYPE: DNA
<213> ORGANISM: Artificial Sequence
<220> FEATURE:
<221> NAME/KEY: misc_feature
<222> LOCATION: (1)..(39)
<223> OTHER INFORMATION: synthetic primer sequence

<400> SEQUENCE: 19
tcgtcgccat ggtagatctt gggttggaag aaccggatc                   39

<210> SEQ ID NO 20
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: synthetic primer sequence

<400> SEQUENCE: 20
agcttgtcga gcttctcgtc gaccgacacc                             30
```

<210> SEQ ID NO 21
<211> LENGTH: 42
<212> TYPE: DNA
<213> ORGANISM: Artificial Sequence
<220> FEATURE:
<221> NAME/KEY: misc_feature
<222> LOCATION: (1)..(42)
<223> OTHER INFORMATION: synthetic primer sequence

<400> SEQUENCE: 21
aatggccatg gttagatctt cgcgaggctt cgaaacgaaa gg            42

<210> SEQ ID NO 22
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: synthetic primer sequence

<400> SEQUENCE: 22
cgcgttcagc tccagatcgt tgtcatctcc                          30

<210> SEQ ID NO 23
<211> LENGTH: 37
<212> TYPE: DNA
<213> ORGANISM: Artificial Sequence
<220> FEATURE:
<221> NAME/KEY: misc_feature
<222> LOCATION: (1)..(37)
<223> OTHER INFORMATION: synthetic primer sequence

<400> SEQUENCE: 23
cgcgatgagc catggtagat cttccttgct tgtctga                  37

<210> SEQ ID NO 24
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: synthetic primer sequence

<400> SEQUENCE: 24
taggtggctc ctaaggccag gatgggctgc                          30

<210> SEQ ID NO 25
<211> LENGTH: 41
<212> TYPE: DNA
<213> ORGANISM: Artificial Sequence
<220> FEATURE:
<221> NAME/KEY: misc_feature
<222> LOCATION: (1)..(41)
<223> OTHER INFORMATION: synthetic primer sequence

<400> SEQUENCE: 25
aagcggagcc gtggtagatc tctttgctag ctagctagta c             41

<210> SEQ ID NO 26
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: synthetic primer sequence

<400> SEQUENCE: 26
acgttgaggt cggcgcgcac gaacaccttc          30

<210> SEQ ID NO 27
<211> LENGTH: 34
<212> TYPE: DNA
<213> ORGANISM: Artificial Sequence
<220> FEATURE:
<221> NAME/KEY: misc_feature
<222> LOCATION: (1)..(34)
<223> OTHER INFORMATION: synthetic primer sequence

<400> SEQUENCE: 27
tcgtcgccat ggtagatctt gggttggaaa gaac          34

<210> SEQ ID NO 28
<211> LENGTH: 36
<212> TYPE: DNA
<213> ORGANISM: Artificial Sequence
<220> FEATURE:
<221> NAME/KEY: misc_feature
<222> LOCATION: (1)..(36)
<223> OTHER INFORMATION: synthetic primer sequence

<400> SEQUENCE: 28
tatctagatc agatccgcgc ttggcggagg gaatcc          36

<210> SEQ ID NO 29
<211> LENGTH: 27
<212> TYPE: DNA
<213> ORGANISM: Artificial Sequence
<220> FEATURE:
<221> NAME/KEY: misc_feature
<222> LOCATION: (1)..(27)
<223> OTHER INFORMATION: synthetic primer sequence

<400> SEQUENCE: 29
cgattcgaag tggtgctcct ccgagtc          27

<210> SEQ ID NO 30
<211> LENGTH: 32
<212> TYPE: DNA
<213> ORGANISM: Artificial Sequence
<220> FEATURE:
<221> NAME/KEY: misc_feature
<222> LOCATION: (1)..(32)
<223> OTHER INFORMATION: synthetic primer sequence

<400> SEQUENCE: 30
ataggcctga tccctgtctt ggatggatca gg          32

<210> SEQ ID NO 31
<211> LENGTH: 27
<212> TYPE: DNA
<213> ORGANISM: Artificial Sequence
<220> FEATURE:
<221> NAME/KEY: misc_feature
<222> LOCATION: (1)..(27)
<223> OTHER INFORMATION: synthetic primer sequence

<400> SEQUENCE: 31
cacagctcct cctccgcctg ctccttg          27

<210> SEQ ID NO 32
<211> LENGTH: 26
<212> TYPE: DNA

```
<213> ORGANISM: Artificial Sequence
<220> FEATURE:
<221> NAME/KEY: misc_feature
<222> LOCATION: (1)..(26)
<223> OTHER INFORMATION: synthetic primer sequence

<400> SEQUENCE: 32
tgtgcatcga gtcacgcgag atacccc                                    26

<210> SEQ ID NO 33
<211> LENGTH: 33
<212> TYPE: DNA
<213> ORGANISM: Artificial Sequence
<220> FEATURE:
<221> NAME/KEY: misc_feature
<222> LOCATION: (1)..(33)
<223> OTHER INFORMATION: synthetic primer sequence

<400> SEQUENCE: 33
ataggcctgg cttggcacag ctcctcctcc gcc                             33

<210> SEQ ID NO 34
<211> LENGTH: 26
<212> TYPE: DNA
<213> ORGANISM: Artificial Sequence
<220> FEATURE:
<221> NAME/KEY: misc_feature
<222> LOCATION: (1)..(26)
<223> OTHER INFORMATION: synthetic primer sequence

<400> SEQUENCE: 34
catcaccgcc ccgtacagct tcatcg                                     26

<210> SEQ ID NO 35
<211> LENGTH: 27
<212> TYPE: DNA
<213> ORGANISM: Artificial Sequence
<220> FEATURE:
<221> NAME/KEY: misc_feature
<222> LOCATION: (1)..(27)
<223> OTHER INFORMATION: synthetic primer sequence

<400> SEQUENCE: 35
tgggcacgat ctcgtagtcg gagccag                                    27

<210> SEQ ID NO 36
<211> LENGTH: 34
<212> TYPE: DNA
<213> ORGANISM: Artificial Sequence
<220> FEATURE:
<221> NAME/KEY: misc_feature
<222> LOCATION: (1)..(34)
<223> OTHER INFORMATION: synthetic primer sequence

<400> SEQUENCE: 36
ataggcctgt cccagaccca acctctcctc tcct                            34

<210> SEQ ID NO 37
<211> LENGTH: 33
<212> TYPE: DNA
<213> ORGANISM: Artificial Sequence
<220> FEATURE:
<221> NAME/KEY: misc_feature
<222> LOCATION: (1)..(33)
<223> OTHER INFORMATION: synthetic primer sequence

<400> SEQUENCE: 37
gttgtcgctc ttcttcggcg cgcgcccgaa cat                             33
```

<210> SEQ ID NO 38
<211> LENGTH: 40
<212> TYPE: DNA
<213> ORGANISM: Artificial Sequence
<220> FEATURE:
<221> NAME/KEY: misc_feature
<222> LOCATION: (1)..(40)
<223> OTHER INFORMATION: synthetic primer sequence

<400> SEQUENCE: 38
ataggcctcc tccgcggtgc cgccgccgct cgccgatgtg                              40

<210> SEQ ID NO 39
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: synthetic primer sequence

<400> SEQUENCE: 39
ccgagatcga tgccgatagc cgggccatcg                                         30

<210> SEQ ID NO 40
<211> LENGTH: 36
<212> TYPE: DNA
<213> ORGANISM: Artificial Sequence
<220> FEATURE:
<221> NAME/KEY: misc_feature
<222> LOCATION: (1)..(36)
<223> OTHER INFORMATION: synthetic primer sequence

<400> SEQUENCE: 40
ataggccttt cttctcactc agcggttgcg gagcac                                  36

<210> SEQ ID NO 41
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: synthetic primer sequence

<400> SEQUENCE: 41
ttctgcaggt ccttcagctc cttgaggatg                                         30

<210> SEQ ID NO 42
<211> LENGTH: 39
<212> TYPE: DNA
<213> ORGANISM: Artificial Sequence
<220> FEATURE:
<221> NAME/KEY: misc_feature
<222> LOCATION: (1)..(39)
<223> OTHER INFORMATION: synthetic primer sequence

<400> SEQUENCE: 42
ataggcctac aaactccttt ttgcaggcag gcaggcagg                               39

<210> SEQ ID NO 43
<211> LENGTH: 30
<212> TYPE: DNA
<213> ORGANISM: Artificial Sequence
<220> FEATURE:
<221> NAME/KEY: misc_feature
<222> LOCATION: (1)..(30)

<223> OTHER INFORMATION: synthetic primer sequence

<400> SEQUENCE: 43
gctgctacca agcacagcaa cagccttcac                30

<210> SEQ ID NO 44
<211> LENGTH: 42
<212> TYPE: DNA
<213> ORGANISM: Artificial Sequence
<220> FEATURE:
<221> NAME/KEY: misc_feature
<222> LOCATION: (1)..(42)
<223> OTHER INFORMATION: synthetic primer sequence

<400> SEQUENCE: 44
ataggccttg tttatgtgat ctcaggcgac ccccgcggcg ag                42

<210> SEQ ID NO 45
<211> LENGTH: 26
<212> TYPE: DNA
<213> ORGANISM: Artificial Sequence
<220> FEATURE:
<221> NAME/KEY: misc_feature
<222> LOCATION: (1)..(26)
<223> OTHER INFORMATION: synthetic primer sequence

<400> SEQUENCE: 45
gatttggccc ccttcatggc ggattc                26

<210> SEQ ID NO 46
<211> LENGTH: 41
<212> TYPE: DNA
<213> ORGANISM: Artificial Sequence
<220> FEATURE:
<221> NAME/KEY: misc_feature
<222> LOCATION: (1)..(41)
<223> OTHER INFORMATION: synthetic primer sequence

<400> SEQUENCE: 46
ataggcctgg cggattcgag cggcgacacg gagcgcagcg t                41

<210> SEQ ID NO 47
<211> LENGTH: 27
<212> TYPE: DNA
<213> ORGANISM: Artificial Sequence
<220> FEATURE:
<221> NAME/KEY: misc_feature
<222> LOCATION: (1)..(27)
<223> OTHER INFORMATION: synthetic primer sequence

<400> SEQUENCE: 47
cacggcagcc tctcgcgggt ctcccac                27

<210> SEQ ID NO 48
<211> LENGTH: 39
<212> TYPE: DNA
<213> ORGANISM: Artificial Sequence
<220> FEATURE:
<221> NAME/KEY: misc_feature
<222> LOCATION: (1)..(39)
<223> OTHER INFORMATION: synthetic primer sequence

<400> SEQUENCE: 48
aggcctctct atctctcccc caagacgcaa cgcagggag                39

<210> SEQ ID NO 49
<211> LENGTH: 32

<212> TYPE: DNA
<213> ORGANISM: Artificial Sequence
<220> FEATURE:
<221> NAME/KEY: misc_feature
<222> LOCATION: (1)..(32)
<223> OTHER INFORMATION: synthetic primer sequence

<400> SEQUENCE: 49
gaagctgggg taatcaacgg tcccctgatt cg                          32

<210> SEQ ID NO 50
<211> LENGTH: 39
<212> TYPE: DNA
<213> ORGANISM: Artificial Sequence
<220> FEATURE:
<221> NAME/KEY: misc_feature
<222> LOCATION: (1)..(39)
<223> OTHER INFORMATION: synthetic primer sequence

<400> SEQUENCE: 50
ataggcctgg tcacacgcga gggggggccgc gcctgatgc                   39

<210> SEQ ID NO 51
<211> LENGTH: 37
<212> TYPE: DNA
<213> ORGANISM: Artificial Sequence
<220> FEATURE:
<221> NAME/KEY: misc_feature
<222> LOCATION: (1)..(37)
<223> OTHER INFORMATION: synthetic primer sequence

<400> SEQUENCE: 51
ataggcctcg gcggcggggt cggtgggact gcggctg                      37

<210> SEQ ID NO 52
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: synthetic primer sequence

<400> SEQUENCE: 52
agaggcagcg gcgaggagat ggagggcgac                              30

<210> SEQ ID NO 53
<211> LENGTH: 879
<212> TYPE: DNA
<213> ORGANISM: Zea mays

<400> SEQUENCE: 53
actctggctt ggagggtccc gaacttacca actttaggtg gaaccgtttt ggattttctt    60
ttgcaatcta atatataaaa gatgtgtttc aatattcaat ggtatagtcc tttttttcata  120
cattgatata tatatataca tatattataa ttatagatat attatgcata ctattcaagc   180
tttgaactag taattaccctt taaggaatac tccctctgac tcaaaataat attcgtttta  240
gctcttgatt ttaatgtcta caatcattac atgatgataa atatagacat atgcatagaa   300
catatacacc aaatattgta tagatgcact aaaattccaa aactaatttt atttaggttc   360
agagggagta tttaatcaag tattgtacta atggtttggt tcccaccaat attacttcgt   420
ctattggcaa attgttatag taacaacacg ttgagtcaaa atgtataaat ttgatcaca    480
aatatacgct agcataataa aggttcacgt ataaaaatga taacattaga tttttacacg   540

```
agaaatatac gctgggcacc acattatttg tagaaaaaat agctgctgaa aggtctctgt    600
cccattctgc cttttgctt gcacctgatt gggtgaacca tccctcccgc ggatcgcctt    660
gctgtaaccc atcccagtcg tcgaaatcct tccggatctt gagcattcct cgcacgcgga   720
tcgctttcct cgcacgcgga tcgacgggcc caccacatct ccccatccac gccattttaa   780
atacacccag tttcgatgtt gagcggcatc acaattcact ccactcatct tttctcgttt   840
agaacctcta aaatttcccc cactcgccag tcgcagcag                          879
```

<210> SEQ ID NO 54
<211> LENGTH: 879
<212> TYPE: DNA
<213> ORGANISM: Zea mays

<400> SEQUENCE: 54

```
actctggctt ggagggtccc gaacttacca actttaggtg gaaccgtttt ggattttctt    60
ttgcaatcta atatataaaa gatgtgtttc aatattcaat ggtatagtcc ttttttcata   120
cattgatata tatatataca tatattataa ttatagatat attatgcata ctattcaagc   180
tttgaactag taattacctt taaggaatac tccctctgac tcaaataat attcgtttta    240
gctcttgatt ttaatgtcta caatcattac atgatgataa atatagacat atgcatagaa   300
catatacacc aaatattgta tagatgcact aaaattccaa actaattttt atttaggttc   360
agagggagta tttaatcaag tattgtacta atggtttggt tcccaccaat attacttcgt   420
ctattggcaa attgttatag taacaacacg ttgagtcaaa atgtataaat tttgatcaca   480
aatatacgct agcataataa aggttcacgt ataaaatga taacattaga tttttacacg   540
agaaatatac gctgggcacc acattatttg tagaaaaaat agctgctgaa aggtctctgt   600
cccattctgc cttttgctt gcacctgatt gggtgaacca tccctcccgc ggatcgcctt   660
gctgtaaccc atcccagtcg tcgaaatcct tccggatctt gagcattcct cgcacgcgga   720
tcgctttcct cgcacgcgga tcgacgggcc caccacatct ccccatccac gccattttaa   780
atacacccag tttcgatgtt gagcggcatc acaattcact ccactcatct tttctcgttt   840
agaacctcta aaatttcccc cactcgccag tcgcagcag                          879
```

<210> SEQ ID NO 55
<211> LENGTH: 745
<212> TYPE: DNA
<213> ORGANISM: Zea mays

<400> SEQUENCE: 55

```
aaatagagcc catcgaagcc cactaaatat ttaacatttc tgagctagtt gtacttttc     60
cttttttaac ccaaatttt aatgtggcac ccacaaacaa cccaatttr ttttggttat    120
atatgttatg tactttttatt tatgttattt catgtgattt gtgctaacct gacacattaa   180
ttttgggtta attaagttgg acagrcacac ttaagtattc gygggtcgtg ttttggatcg   240
acggcgccat gttttggatc gacggcttga cgtcttggtc cacgggctgg cacaccacga   300
cccgtaattg aaattgtact ttagtggact gtgcccctagt ggattgtgct ttaataagcc   360
tggggtgtac catattgggc taatccagat atacatgtac accggggagt atttatcttt    420
grcacaagga gtatacataa taataacgat attgttcgct tcagattaaa ttaaaccaag   480
cgagtatgcg tgcatgtgta cgtcggatgc tttgtttgtt catttgtggc ccgtgaagta   540
atatttgggc ccaatagccc attcatccat gtcctaaccc tagggcgcgt tccttataaa   600
acctatctcc attctgttct cactctcaga caccagacgc agtcggctgc cgcagactgg   660
```
trgtagccgg cgcgccgtca ccgtatcctc agatcagcgg cgagcagata ccacaccact    720
ctactgacgc ccgacgagca gtgta                                         745

<210> SEQ ID NO 56
<211> LENGTH: 446
<212> TYPE: DNA
<213> ORGANISM: Zea mays
<220> FEATURE:
<221> NAME/KEY: misc_feature
<222> LOCATION: (1)..(446)
<223> OTHER INFORMATION: n=a,g,t or c

<400> SEQUENCE: 56
ctagagagat cgggagctag ggtttgggga tattttttcct tctctctacg agtgtgatct    60
gatctgcggt agagaggga gaacgggtgc ggtaaaatag ccggcccaa gggcaagggg    120 gcgccgggta gcgtttgcgt cgaaccaacg cgattctccc tgccgcaggt gctggtggtg    180
gccccggccc gcgccgttcg ttcaaaaggg gcctactata cacgtaacac gccgaagcca    240
gagccgttcg tccacttcag acagtgtaca gttaggattc acatatatga tatatccgtt    300
angctgtgtg acctgtgtcc aactgcattt ggatgccaac gcgcatttac cgtgatgtca    360
ttgccgctac tgtttgacta tctataccac tatataatct aaaaaaattt accaaccccg    420
ggccgtcnac acgcgtgccc tatagt                                        446

<210> SEQ ID NO 57
<211> LENGTH: 1159
<212> TYPE: DNA
<213> ORGANISM: Zea mays

<400> SEQUENCE: 57
aaagtccata tttcttagat ccatgaatgg ctactacact caattaactc tattgatggc     60
aacaataaaa agagatcaaa attatgggta aatagccaac acatataact ccaccgcata    120
agcgcgtcac cacaatacccc aaaacaacta agaaccgat ggtcgatgag cgatcataag    180
atcaacctct ttaacaacat ctacaaccgt ttgtgcacag cctgattgag tgacccaatg    240
aggctatgct gctttaagcg gttaaggaaa atttccacaa caagcataga aaaacaagt     300 tggagcacac gtgacacgtt atgccattag ctcaagtggt gcgtaaaaca cgatgataat    360
gactcgagtg atgagagaaa aagatatgtt cttaacttgg acgacaatca aagctcaatg    420
acatatgaaa gtatggacac actatgctct attgtcacca tagggcaaga gttcagtaga    480
aggcaaattg ttcgacaaca agctatgttg gtcttttgat tctgacgagt caatgatagc    540
ttttcaatga tactattaac tttctaaaat taggaagcaa caaaaatct acaaaaaca     600 tactttttaa cttttggtaa aagctaaact tttttgagtt ttttttccgaa agcacgccta    660 gtcagccacc agctggcacg cgagtctccc aacaatagga gggaccacct gtcatgctgt    720
gggaccacga agaaaacccct ccagagacga cgatagacct ccgtccatag acgcggtcta    780
ccgtggtccg gacgctcccg gccgcgaatt caggtcgtgg cgggccctgc cgacccaact    840
actggtccag aggcctccac gcgagccgtg ggccgtggtc taggagccgg gtccgcctat    900
ctacttgacg tcacggaaa cccggacccg gtaggaagga gctataaaga caagccaaac    960
gagggcatcc cttcttcagc cgcacgcttc ttgttgccaa agaattccct cccctagccg   1020
ccgccgccgc cgctcgtctc cctgagaggt gccgggaccg aggaactggc cgggtactag   1080
gtagagaatc ggttttttctt gtctcagccc ggggtctgct gcgtctggtg gtggtgaagg   1140
ggagaaattc gtgagatct                                              1159

<210> SEQ ID NO 58
<211> LENGTH: 762
<212> TYPE: DNA
<213> ORGANISM: Zea mays

<400> SEQUENCE: 58

| | | | | | |
|---|---|---|---|---|---|
| gtcgacgtct | gattggacca | gaatttcaga | tggtgagcaa | aagtgccact | tgcctgcctc | 60 |
| cttttctcgt | gcctgcctaa | catgtgcctt | tgatctctag | ggcaattata | ataaagacaa | 120 |
| gcaggttata | ttataagtca | aggataaaaa | gaaaggagaa | acaatatact | atttaagatc | 180 |
| agatataaaa | gagttaataa | ttttttgaga | cacatatact | ggttacattg | ttacaatctg | 240 |
| tatatatcac | attgttcgaa | tatgttccaa | atttttacga | tgattcgtgc | tctaccggaa | 300 |
| ctacttctag | attttgaaaa | ctttatgaga | attttcttat | tttagatata | ctaaggctaa | 360 |
| ttttggttga | tttttggctc | gctagctacc | attacctctg | catctagaca | ttacaaattt | 420 |
| acaataaata | aagttcctag | attttgaacg | aaaccagcag | agcgcacacc | gtccttgccc | 480 |
| cacggaacaa | ggaaaagggt | atatgctccc | gcagccctcg | tggaaaccaa | gggcggacct | 540 |
| tcccctcctc | caagcaaatc | cgaggccac | ccacgggccg | ctcgaacatc | tgtcaccgcc | 600 |
| aagtggcccc | accccacccc | tcccctccgc | tgccccttct | tctacaaata | ccccggccgg | 660 |
| ccgcggccgt | tcccgaatcg | agcggtgact | ggcgaggcaa | aagcattgcg | accacagaca | 720 |
| gcgcgcgctt | caaggccttt | tttttgaga | taacaaggag | ga | | 762 |

<210> SEQ ID NO 59
<211> LENGTH: 973
<212> TYPE: DNA
<213> ORGANISM: Zea mays

<400> SEQUENCE: 59

| | | | | | |
|---|---|---|---|---|---|
| cctgacgtag | atagagaaga | tgctcttagc | tttcattgtc | tttcttttgt | agtcatctga | 60 |
| tttacctctc | tcgtttatac | aactggtttt | ttaaacactc | cttaactttt | caaattgtct | 120 |
| ctttctttac | cctagactag | ataattttaa | tggtgatttt | gctaatgtgg | cgccatgtta | 180 |
| gatagaggta | aaatgaacta | gttaaaagct | cagagtgata | aatcaggctc | tcaaaaattc | 240 |
| ataaactgtt | ttttaaatat | ccaaatattt | gtacatggaa | aataataaaa | tttagtttag | 300 |
| tattaaaaaa | ttcagttgaa | tatagttttg | tcttcaaaaa | ttatgaaacg | gatcttaatt | 360 |
| attttccctt | aaaaccgtgc | tctatctttg | atgtctagtt | tgagacgatt | atataatttt | 420 |
| ttttgtgctt | aactacgacg | agctgaagta | cgtagaaata | ctagtggagt | cgtgccgcgt | 480 |
| gtgcctgtag | ccactcgtac | gctacagccc | aagcgctaga | gcccaagagg | ccggaggtgg | 540 |
| aaggcgtccc | gccactatag | ccactcgccg | caagagccca | agaggccgga | gctggaagga | 600 |
| tgagggtctg | ggtgttcacg | aattgcctgg | aggcaggagg | ctcgtcgtcc | ggagccacag | 660 |
| gcgtggagac | gtccgggata | aggtgagcag | ccgctgcgat | aggggcgcgt | gtgaaccccg | 720 |
| tcgcgcccct | cggatggtat | aagaataaag | gcattccgcg | tgcaggattc | acccgttcgc | 780 |
| ctctcacctt | ttcgctgtac | tcactcgcca | cacacacccc | ctctccagct | ccgttggagc | 840 |
| tccggacagc | agcaggcgcg | gggcggtcac | gtagtaagca | gctctcggct | ccctctcccc | 900 |
| ttgctccata | tgatcgtgca | acccatcgag | ctacgcgcgt | ggactgcctt | ccctgggtcg | 960 |
| gcgcagtagg | gga | | | | | 973 |

```
<210> SEQ ID NO 60
<211> LENGTH: 693
<212> TYPE: DNA
<213> ORGANISM: Zea mays

<400> SEQUENCE: 60
aaaagtcaag agcatcatat atttgtgaac agtgcgggtc cataagagga agctcacctt      60
atttagcgtg tgtgcggtga gatgagatga tttggttctt gtttaggttg ttcgcttagc     120
tttttttttt accgatatcc gttttaagct gaagcattga tttcattaaa attttcgaag     180
gtgagaatcc gtccgatccc tgctactccg cagcgctaaa agctgcagct gcaggtcagc     240
aaccagttgg agccaaaaca atggtcgagg ccgccggagc ggaggccacg agacgagacc     300
ggggacgatc gatagcaggc cacctccatc tggccgttgc ctttccaaca catcggtttc     360
ccttccagaa ccttcccacc ctcccattcc aaaaccatcg aatccgcgcc gtccattacc     420
aatccgcggg cccaggaaac ccgcaggcgc cgctcttacc cccttcccaa gccacaccgt     480
tcccccgccg ccaccaggtc ccaccaagcg cggccccgc gtgtcaggcg cacaaacagc      540
cacacaccgc ccgtgtggct gcgtccggct gtctgtctat aaagaaaaac agaccgtcca     600
ttcgatcgcc tcacccgaag cacatcccgt cgcatcccat cccactacca cccatctcgt     660
cgtccgccga ttcgatccgg ttcttccaac cca                                   693

<210> SEQ ID NO 61
<211> LENGTH: 1107
<212> TYPE: DNA
<213> ORGANISM: Zea mays

<400> SEQUENCE: 61
ataaacggag ggaaattaaa ttaagggcca ccctctgatg actgatgcat ctcgcgcaac      60 cttattttg ttgcagcaac agcaacaaag cgttgcttct gcgccactca tcttatatat      120
ccctcatgtt tggaaaaaaa ataataatga aaagaacgtg caccactctt tgctggcagc     180
ctggcaccga cacacacatg tgatacaaac aatgatattt agatttgatt tgaatagagc     240
atcagtttgg tgaaacacgc acctttgtgc acgcactgtg caattattag tttgttataa     300
gacttagaag cgcacgttga cacctaatcg caccatgatg tatggctgga acccgaaacc     360
tggtcgcggg ccgagatgca gatgatgcag cggaaacgca cactggctca cttttttcgtt    420 tctttgaaaa ggatagttag ctattacatt ttttagcaaa catttatcga tagcgcaact     480
actactagta aactagtgtc gcgttcgatg tctccgaact tgtcacacag cattagcaga     540
ccacggcgca cacgataatt ttcagttaac aggatccaat tatacctgca catccccatg     600
acagcattaa gaaagtataa cataatttct atccaaaaaa aagttaagat aacataatca     660
ggatggtata gctgccgaaa gagactggtt tgttaaagca cggagcctaa tgacacactg     720
acacgccgtc cgtccgcgtc cagcccacgc gaagccggcg gccagctcag cgttcaccgc     780
gccatccccg atcccggtcg cggcgccgac ggatcagacg ggacaggcgg gctagcctcg     840
acacgacgag aaccccgagg tccgcacggc cgggctcttc ccgtcgcgcc agatgtcaga     900
cgccgtcacg acgcgcggag catccggcac ccccgccgca cattccgtca ggcgcctga      960 cggagaccgc ggccgctata aatgaaaccc gcgctgtcct gctcgctcgc gcacacggca    1020
gacggcacac acaccacacc acacctcctc gcttccactc cgctcgtctg acatctcgtc    1080
ccgtcctttc gtttcgaagc ctcgcga                                        1107

<210> SEQ ID NO 62
```

```
<211> LENGTH: 631
<212> TYPE: DNA
<213> ORGANISM: Zea mays

<400> SEQUENCE: 62
atcgtgtccc ttgagtggat gaagccttga ccggaatcgc gcccatcaga cctttgcagc      60
tttgtgctga tgaaggttac cagctgagat taggagtctt gagattaccc ctaattatgg     120
tccccgacac catatatccc acttttacgt caccacgtcg tcaagatttc accgtttacc     180
ttttcatctt ctatagcgat tttttttctaa attctcccct atttctacta caactataaa    240
atatattttc catacctact cattatctat tatcaaattt cttcttacta acgattacta     300
aggtgtacgg aaaacaaaaa tgataagtgt tttaaggtga acgccaacaa caaggggtga     360
gaaaaagaaa ccgccatgta gtggggctgc taggggacgg ccgtgccctg tagcccctaa     420
tcccctgtga tcggatcatc acaaaatatc tttggagcgc ggttgatatt atcactataa     480
atagggtttt acacgaaaaa tcgcaccatc tagaggttta tgaagcctcc aaaaaaaata    540
tctaaacaac tacttcctag tataaagtga cagtagcggg ggagaaggga accgaaacca    600
agcaacccaa tccaaaccag acaagcaagg a                                   631

<210> SEQ ID NO 63
<211> LENGTH: 1026
<212> TYPE: DNA
<213> ORGANISM: Zea mays

<400> SEQUENCE: 63
atctttgccg agagctctcc tgtgccgagt gtcctgcact cggtaaacca gctcgttacc      60
gagagcagga gtttaccgag tggctctcgg caaagtcgcc tttgccgagt gcccgacaaa     120
aggcactcgg caaagctgcc ggcattcggc aaagcctgca attccggtag tgttttacca     180
cgttgacaaa aaaatgaag aaatccgata ttttagtcat tatggatatg gcgcggtgtc      240
aaatcggtat agtcataatc ctttccatag gattgtccca tgctcgacac attaacacta     300
agtttatccc tgaataacac ggctacctcc atcctaatct tttctattga tcaattgcct     360 attttttaagg cgcagttgtt cttggccata tctgtggaga tgattttttt aaagacgtcc    420
aactctagct agctagtccg tgtatgtgaa cggtgttagg tagtcattgg atccgttgac     480
tatatttgta aaggtggtag ccgttctttt taattttaac gccgctggga agaaattaaa     540
cgtggtacat ctatgtatcg ttttcttaac agtgatataa taatatacta tcattgcatg     600
cgtccgcaat tgctctctcg cggctcgttc taccgtggga agaagagctg acccgtcgcc    660
gccccacatg catacgatgc gtccttatct gtcgcggctc gtgcaaacgc ggggcgggct    720
gagcgcccca gcccaccact tgcaccactt gcatttactt aattagttca taacacatca    780
catctgtatc ttacattatc tttaaaaaaa tgattcacac attatttata tatgagatat    840
aataagtttc caggaagcat ctttggcgac ttacgtacgt gtatcagaga catggagtga    900
taaactattg ggcaaccatt tagcaatcct agctagccag ctcgtctata aatagatgca    960
tcagctccac ttggtctaca cacttcacaa gcagctcaaa gctctagtac tagctagcta   1020
gcaaag                                                              1026

<210> SEQ ID NO 64
<211> LENGTH: 1039
<212> TYPE: DNA
<213> ORGANISM: Zea mays

<400> SEQUENCE: 64
```

```
cctcgagcga agggtggcgt ctatgccttc gccccaacac taactcatta gagtcccacc      60
gcgccattgc aacacgacaa tgggtgtcgc ttgccgtcac catcatctat cgctaccttg     120
cctcctgcac tcgctcctcc tacttgtcgt cgtctcacca acgctatctc acgacaaatt     180
cgatgactcg ccagaacgac gcgcttatgc ggctgctccg ccctagtgcc tcgtcctcag     240
tcagtccacc tattttctcc ttctagctct tctttcggga gccaaaaagg ttttttggta     300
ttcatatcct tttgggaaca ctagattatc atttaatatt catgttatta tcattaatct     360
atatttatgg tctagtctgg tgttgcgttg tcggccccac ctagaatttt gttctgcgtc     420
cgccactgag ataatttggt tcttgtttag gttgttcgct tagctttaat tcgtaccaat     480
atccgtttta agctgaagca ttgatttcat taaaattttc aaaggtgaga atccgatccg     540
atccctgcta ctccgcagcg ctaaaagctg cagctgcagg tcagcaacca gttggagcca     600
aaacaatggt cgaggccgcc ggagcggagg ccacgacgacg agaccgggga cgatcgatag     660
caggccacct ccatctggcc gctgcctttc aacacatcg gtttcccttc cagaaccttc     720
ccaccctccc attccaaaac catcgaatcc gcgccgtcca ttaccaatcc gcgggcccag     780
gaaacccgca ggcgccgctc ttacccccctt cccaagccac accgttcccc cgccgccacc     840
aggtcccacc aagcacggcc cccgcgtgtc aggcgcacaa acagccacac accgcccgtg     900
tggctgcgtc cggctgtctg tctataaaga aaaacaggcc gtccattcga tcgcctcacc     960
cgaagcacat cccgtcgcat cccatcccac taccacccat ctcgtcgtcc gccgattcga    1020
tccggttctt tccaaccca                                                 1039

<210> SEQ ID NO 65
<211> LENGTH: 1888
<212> TYPE: DNA
<213> ORGANISM: Zea mays

<400> SEQUENCE: 65
cctgcctttc acatctagtg gcatcttaaa tctgtcagtc cagcttatca agattagtca      60
ttcagttatg atgtcttcta taaggtacaa tcataactag aatgaaaaga aagtgcaatt     120
accaggcgag aacacagcat ggtacatgag gattccagct acaactgata tattaatggc     180
gtgtttggtt tgcaggttgg gctgtttccg gagtcattca gtcctgtgtc cgagcctaca     240
tcagcgttgg tttgaatcgc tgaatgatgt cgtccatcac tgtattgttc taataacaga     300
ctaacatgcg ggttcagctc actccacaac aaactgtcgg accgctccat ccggagccag     360
gccacgacgg atgagtcaaa tcgttggacc aaacgcgcag taaacgaatc caccatgcct     420
ttagttggaa cgctacggtg caaatctgat aaatatagag catcgtcatt tatacctat     480
caccaaagaa ttagctgata cctaacttt attactgtga aatatgttag aaaatgaggc     540
attactagtt ttaatttagt ccagaaaacc attgtaattt atgtgacgac atgtatacca     600
ctattcgtat aagcagtaca caaaaagac acgcaaaaag tatggaaaac aggaagttcc     660
ctgtgaaggg accgatgctc aaagtatcag cggcccaatt cacacaagac atctcgtgtg     720
tatgttcgat ataattgtac gaactcgatg caggcaggtc tacgcagtgc agtccctcaa     780
acagcgccga cggcgaagaa ccagagcgga tgaagcgagc agttgcaagt acgttactca     840
aaaacctgat cgtccacaca ctcgtgcaag tgtacatatg cggacgacga tttcagggag     900
aggagaaggg taacgaacag taacggtcac gccattagaa ccagaaactg aggagacatt     960
agggcaataa accgacgtcc ttctactagt tatagaaaga aaacagacgg tcattatgat    1020
```

```
gagggaaatt tggatccata ccattaaaag atcaccactt tggatccata ccattactat   1080
ctcacttaca tgtgggtcca catgagtcaa tgacatgtgg ggtccatgat atatatctaa   1140
agtttggatc ttttaatggt atagatccaa ttgttcctta tgataatcat cactcaatgc   1200
aaaatatata actgtttgaa agaaatattt agaccaagct cgacctacca cgaactacgg   1260
cctcgcccat gaccacggct cagacctagc cggcggcggc ggcgcgcgcg ttcaggtcaa   1320
cggtaaacca agcatgatga aggatgaaca tcccacggca gtgcgttttc acaacgaatc   1380
tcaagttctc aacccgatcg gatcataaga gctttgtaaa cgttcccgca ccattgtttt   1440
cttatcgttg atcaggagac gctgaaaggg aagtggaaag tcttgaggga atgaaaagga   1500
aagaaagcaa agaggggaaa aaaggcgagc aaaaggaggc ggaaacatgc tttcagccgt   1560
ccgtggcgtg attcaaacgc gagaagatgc cctgcccctg cagccgtaca cggtccgatc   1620
acctgaccga actgacggct cagatttgct caacatctgc actataagtc gttccaccga   1680
catgcgggcc cgttatacat agaaccccac agtcagtgag acacatggtc ttctctctgg   1740
tggaagcggt gggtgcacat gctgctagca gtataaatat gctgaaagcc tgaaacccta   1800
ggcgaagctt atcgcttatc atccgcgcct ctacatttct tctctctctg ctcctccgcc   1860
tccgcctgat ccatccaaga cagggatc                                     1888

<210> SEQ ID NO 66
<211> LENGTH: 1379
<212> TYPE: DNA
<213> ORGANISM: Zea mays

<400> SEQUENCE: 66
aaaatatcga ttcatgaagc acccttttgg ctgcttcata gatttaggcc ctgtttggga     60
gggtcatttc aagaattgca gattcggttt tctagcttcg ccatgaaacg gtttcaacag    120
attagtaaga caggattcaa gagtgtttgg tttgcacata gactccagct tctgtaatat    180
agttaatttg tgcgagtttc cttaattacc tttgatgatt aatggatgga gaaagagaca    240
cgaattgata ggtcatgtaa caaatgaatg tatggtgggg aattttttgtg caacttcatg    300 aggaggtatg aaaacaatgt ttttgaagca cccttcgagg agcttcaaaa atttcatgaa    360
actggtctct agtttcagtt tttttggaac tagagctcgt ggagctggac ccgtttggat    420
agaacaagct gaaatagacc tgaaattttt gaaatgaagc tcttccaaac agacccttgg    480
tgaacttagg gtccatttca cctttttttg gtgaaactga gttggtgaag ctaagagtgt    540
ttgactagag ttttcggccc tgtttgggag agctttactt taagaatttt aagtctatt    600 cagcttctat ccaaacacgt ctagctccac gagctatagc ttaaaaattg aaactagagg    660
gcagttttat gaaaattttc aaactcctta aagggtgctt caaaaacact attttatac    720 ctcctcatga agttgtacca aaatcaccca ccatgccgct ggttaaatga cctaccgatt    780 catgtcttt tctccaccg ttaatcatca aggtttatta agaaactca cataaattaa    840 ctgtattaca gaagctgaag tctatataca atccaaacat tcttgaacac cggcttacca    900
atctgttgaa gttgtttcgt gatgaaactg aaaaccaaa actataattt tgaaataga    960 gcccttccaa acaagacctt atagagctaa gctagatttt atgaagtgaa gtagtcccaa   1020
acatccccta aacaaacag attggtaagt ggcatggtcg atcggttcaa cgtgtttaga   1080 cctttcgct attttgaatt gggctggacc tacggcaggg actagctagt cgtttcgtga   1140
tatggtttcg tgatatggag tcgatagtgt gcgcccaggc ccagtttgct cgattcaatt   1200
tgccatgggt atttatttgg tgggcactag gcctcactca gcccaccggc gcctatcccc   1260
```

```
aaccctaggt cagcccatat atataaaccc gatatatagg gtctcacttg tgtacccccaa    1320 cgagaagagc ggcggcgcgg gcggacaagg agcaggcgga ggaggagctg tgccaagcc     1379
```

<210> SEQ ID NO 67
<211> LENGTH: 1892
<212> TYPE: DNA
<213> ORGANISM: Zea mays

<400> SEQUENCE: 67

```
ctgatctcgt ggagtcatcg ttccgcgagt gctgagcaat gagagttaaa tggtctgaca      60
aactcacaca agggatgcag gtcgaaatca cctcacgaga atactataat tatcttggat     120
tattagtacc atttctttat tcttagtgaa tacaatgtga gtgatttttt tttgggagga     180
agcaatcaat acagcttgtc atgcttcaaa tagtctctat tgacattggt tgctatagaa     240
gacaccatat gagctcttaa ttggaatata tatcatcaca aatttagtgt tatctttaaa     300
attaaagtta actttaaaat atttaacctc ctagcatata ccacaaatta aagagtaaag     360
cagcacgcga acctgcaaca tgcttagatt tcttgcctgg cattgcgtca ctgcatatgt     420
ttggttgcta agctagatta cctcgattta tgtgctagta agatttttct cttgtgtttt     480
cttgttgtcc caaattaggt cgtttgatct agtaagattt tatcatttta gcctgattta     540
aagggtgttt gatttcaccc aactaaactt tagtatctaa tgaatgataa ttacatgtat     600
taaacatggg ctaattataa aactttgaag gatagttatt ggtattaaat atggtctaat     660
tataaaactt attgtacata tgaagactaa aagacaagac actttattaa acccattcaa     720
gtctatattt aatactcaca attgatattt aaatatttga catgatataa actgaagtaa     780 actttatttta ccaaaggcac cccctttagc tcgggtggcc tcacaaagcg cgctatgaga     840
aacctgctag accaggcgag ccattttttgc tacaacgcga catcaaggaa aagagccatt     900
tttgctaaac ttaacatcaa ggaaaatact gtcggtgcag gaatcgagag aagcaaaggt     960
acaagaacta aacagccatc agtttgtcgg ttggctagac tgcaaagtgc aaagtaccag    1020
gcggcccttt gtgctgccca gcaaggcagg acgaggctgc tatgctggag aacaaagcag    1080
ccgctgcagc ccctgctcca tgtgggtccc tcggtggcgc actaccgagc gtagtcgctg    1140
gcgtaatcgc gtctcctcat ctcttgcggt aggggtgtt tggttagagg gaccaaagat    1200
tagtatctag tttttagtcc tatttagtac ctttttttgct aaatactagg actaaaatga    1260 tttagtctttt agtactttac atatgtgcta aaagggacta aaccatatta attctatatt    1320
tacctctcat ttagttcaat tcaattgtac taatagcact aatagcagaa gaatgttaaa    1380
aactatttta gtcttattat gagtcattta atatattctt attatttta gcccccttgaa    1440 ataaacatgt taggaattaa actttaattt cctaactaaa ctttagtcct tagactaaaa    1500
aaaacaaaac acgccaaac aacggactcg tgtgaaagt aagcagaagc atctagacgc     1560
gcgggggcgg ttggggcctc gctgaccatc agaactgaca acagcgctgc cgcacctacc    1620
cctctccact acgactccac attttccaac ggatttttat ttttctaaga aaattagttt    1680
ttttagaaaa atagaaatca cttggttgca ctaaaaaaag caggcatact cgtcactcgg    1740
tcgccgcgcg acctcccagt tcgtctatta aaggggaacc agtgaaccac ccgatgcaac    1800
ttgcgtagag agttgggcgc agagaatccc caagcaaaca aacagggtag agggagagga    1860
gaggagagga gaggagaggt tgggtctggg ac                                  1892
```

<210> SEQ ID NO 68

<211> LENGTH: 427
<212> TYPE: DNA
<213> ORGANISM: Zea mays

<400> SEQUENCE: 68

| | | | | | | |
|---|---|---|---|---|---|---|
| cctaaaacgg | gcccggaccg | ggccgggccg | ggccgggcgg | cccatttgga | cagtcacgag | 60 |
| tgagaaggcg | agagcttgtc | caaacgagca | ttttcgggcg | tgtgaacacc | catttcagca | 120 |
| aagccgtcgt | tgtccagttc | agcgaagcgc | attctgcggc | tttggcgtga | cccattatgc | 180 |
| tagctcagca | ctgagaatac | gcgtccgctg | cagcgttggc | gtacaggccg | gactacatta | 240 |
| gccaacgcgt | atcgccagtg | gcaaaccctc | ttcgcttcta | actccgctgg | gccaccagct | 300 |
| ttgaccgccg | cctcccttcc | cctccgctac | tgctcctccc | cacccactc | ccccgcagga | 360 |
| gcggcggcgg | cggcggcggc | ggcgaggtcg | taccccacat | cggcgagcgg | cggcggcacc | 420 |
| gcggagg | | | | | | 427 |

<210> SEQ ID NO 69
<211> LENGTH: 1185
<212> TYPE: DNA
<213> ORGANISM: Zea mays

<400> SEQUENCE: 69

| | | | | | | |
|---|---|---|---|---|---|---|
| atccgaccaa | ataacatatg | tatccgtcac | ttatccgtcc | aaataaatat | ctggtcgctg | 60 |
| tatccgtatc | tatcccgttt | ctaactattt | gtatatgatc | ccgaatccga | ttgaaataca | 120 |
| ttagggtagg | atacaagatg | agcccctatc | cgtctgtata | cgtcccgttt | ttacccatac | 180 |
| tcgtcaaact | ttttaggact | tgtttgattg | tgtccgaatc | aaaggggatt | gaaggagatt | 240 |
| aaatccctcc | ctaataaaaa | ataaatgaaa | aaagatttaa | tcttcttcaa | ttcaaacgca | 300 |
| atggaacaag | gcgttagaag | tttcatccaa | cttttttgct | ggtcttaatt | gcaacttctc | 360 |
| ctagagcact | gttgactcca | tcttccataa | ctccattaag | ctcagagcta | gaacctacat | 420 |
| ttatgcacaa | ttttttttatt | tcaaaagaa | cctacgtcta | ttccaaacga | tgtgataaaa | 480 |
| aatgcaataa | ttttgtaggg | ctagtttaga | aactcaaatc | ccctatataa | tcaaaggaga | 540 |
| tttaagtttc | tcgtagagct | tatttggatg | catgggattg | taagagctcg | tatggtgttt | 600 |
| gatcgagttt | cttcatcaat | gtagaccttg | tttagatact | ctcatattta | cttcaataca | 660 |
| tgtgtattga | ggtgaactag | agtgtaaatt | agtttaagtt | acactttaat | ccactttatt | 720 |
| acacgtggat | tggggtgaat | attgagtatc | gaaacaatga | ctcatcaggg | aggcttgtct | 780 |
| ctgtgggctg | gttctaagcg | taagcgggcc | ggccagcact | tatggtatat | gacttgggct | 840 |
| gagatctggt | cacaacccat | ccctccgtca | aagattcctt | ttactcacgt | gaaagcaacc | 900 |
| agaaaggaaa | aaaaaggccg | tttaaatagc | cgaaaggcgc | ccgtggaaaa | gacgccgcca | 960 |
| tgcgccttcg | ttcacacgat | cgcgtgccaa | cggctcagat | gtccccacga | cgcgcccagg | 1020 |
| aacattccag | aacaccacag | cccacgcgct | gacgacgagc | cctttgttcc | ctataaaagc | 1080 |
| cactgcccgg | ctcagtctct | cgccctctcg | aaacccagt | ccctgctcc | attctcagcc | 1140 |
| gccgccaatc | ccttcccgtg | ctccgcaacc | gctgagtgag | aagaa | | 1185 |

<210> SEQ ID NO 70
<211> LENGTH: 1552
<212> TYPE: DNA
<213> ORGANISM: Zea mays

<400> SEQUENCE: 70

| | | | | | | |
|---|---|---|---|---|---|---|
| ctgcttgtgc | tgaagatgac | gactgaacaa | ttggtgcacc | catagagctt | ccacttgttt | 60 |

```
ttctcttgtt tcctttcaaa gaattgacaa tacactatta gacatgttca agttcatact    120
ctgaaatcaa caatacactg caactctgca ataaaaaaac atacctgc tgaaacagag     180
ctgctgctgc tgcctctcac agaaggaggt agtggtggtc gctgcggctg tggaggcagt    240
ggcaatatgc tttccaaacc taggttgttg ttcccagtct ctgactccgc aggcattgag    300
tctgaatggc gtgctcctcc tcctccgggt cctgttccag agtgagacat atcgagtctc    360
aactactgca aacaatcaaa tgccaatacg ccactctatg aacaattgag caattaacca    420
aacaatcagt taaccaaatg cgctggatgc ctgaattgga tttggagctt ggcgagagag    480
acatacacgt acgtactgcg gctgcggtac tggccgtgtc ttcggcactc ggctcggcag    540
acggcagatg gagcctggag gctggagaac gacgcctgga cggctggacc gacgacttcg    600
acggccgtgt cttcgacgcc tggacggctg gaccgacggg acggcttcga cggctggaga    660
acgacgcctg gacgcctgga cagcagtgtt ggcgatagca ggacgcctc gacggcggtc    720
ggcgaacagc aggacaacct ggacggcggt cggcgaacag caggatggcc tggacggcgg    780
tcggcggacg gccggacggg tgagtgtcgc gacgtctcgt gttgtcggcg gacggacgga    840
tggctggaag aaaaaaaata cttagggttt cactttagca attagcaatt agcatggtcg    900
catggacttt agcaatttgc atcgtctgac cgagtgcagc cgtgcaggag tagcgtggtc    960
gcgtcgcgtg gagcccaagc ctgtaggctg tatcctgttg ggctgttggg atgttgggtt   1020
gggcttggta gatttaggcc tttacttgtg actccgcttc gggttaaatc cggaataaat   1080
atggaaatat cccgaccgaa tacaggatcc cgacaatccg aacggaaaat agcatttccc   1140
gtttccgtcc cgctcccgtc gacggccaac ccgtaacccg tccgaaccc gtacttttcc   1200
ggaaatccga aaacgggcgg gttaaatgtg aaaatgggg cgggtcggga cgggattttt   1260
tccgtccgtt ttcatcccta agcccaagtc aactgcggga agtcgagcaa tgcaaaccag   1320
acactcggac ccggccggca acgtaggacg aacgttccac tcctcttgcc gcagagaaaa   1380
tggataaaag ccgactcgga cccgctttga agttgaaac ccgtctcgca ccacaagcga   1440
gcgagggacc cggggcggaa gaagagagag aagacgtctc tctcctctcg gcgtccccgt   1500
tccccaacct ctcgtctgct gcctgcctgc ctgcctgcaa aaaggagttt gt           1552

<210> SEQ ID NO 71
<211> LENGTH: 676
<212> TYPE: DNA
<213> ORGANISM: Zea mays

<400> SEQUENCE: 71
atccgtccgt atccgatccg attacatccc tagttgtatg cataaaagtg caaaaggctg     60
gaacatgttt cgattatctt aaaaaacatg ataacttatt aaggccttgt tttagtacac    120
cagctaaatt ttaactgact aaagtataga gagtctccca ccgttcataa atatttaaca    180
ctattgactt ttaaaaaaaa cattgaccac tcgtcttatt aaaaaactat taagttgtca    240
tttttattga tttcattatt taaggtagtt tatgcttgac ttaaaatttt atatttttaa    300
taaatatttt gaataagatg agtgattaaa gtatttttt taaaaagacg gtgtcatata    360
ttaaacgtag actgatgtac gtgctgagag caacgcaaaa ctccaaatac ggtctaaaat    420
gtaaatgaaa ctccgatcca acgggcggca gggcctgctg tcgttgcgg aatagtaacg    480
caacttgact gcaatgtttg gctgcgccta caaatccaac gcaccaacac accgcgcgcg    540
tcctcatcct cacttcaggt ctgcagcccc caactacccc cagcctcgga aggaaccttc    600
```

```
cagaagcgca agactctaaa ggccgtcgcc ttcccattct tcctcgccgc gggggtcgcc    660
tgagatcaca taaaca                                                   676

<210> SEQ ID NO 72
<211> LENGTH: 2452
<212> TYPE: DNA
<213> ORGANISM: Zea mays

<400> SEQUENCE: 72
acttttgctt tagatcctga tacatcttac cgctaccagg atgaatagag taatcagagt     60
catgggtttc cttcagaata atttctcggg ggctgtctat atcaggaaca catatccgga    120
tcttgaacca tattgtgcct tgctcatcct ccgtgaagtc tggacatcta ccttcagtca    180
tcagatcctt aatttcttgg attttagcat cactgatctg acctttgtgt atttcttgct    240
ccaaggtagg ttccacttta atagtgatcc cttcagtgtg tgcaactatt cctaggttga    300
gtcttctaaa atcttctact aactcatcgg gtaactgagc gacaacaact gcatgaacat    360
gctcctttcg actcaaggca ttcgcaacca gattcgcctt gccgaatgaa tagtgaatct    420
ccaagtcata gtctttaatg agctccaacc aacaatgttg ctcgaggttg aattttttct    480
gagtgaagat acattttaag ctcttgtgat cagtgtagac ttgacactta gttcccattg    540
tataatgcct ccaaatcttg agagtgtgca ctacggccgc caattctaag tcatgagtgg    600
ggtagttcaa ctcatgtttc cgcaacttgc gagacgcgta ggcaatgaca tgtccctctt    660
gcatgagaac acatcccaag ccctggtggc acacatcaca atcgcaatat atatcaaacc    720
ccttctatag atccgacata attaacaccg ggggtgactt caatctgaac ttcagctgaa    780
agttcagctg attgaaacta tcttgacatt cacgagacca attaaactcc tttctcttca    840
ctaatagtga ggtcataggc ttaataaaaa tggagaatcc ttcaacacgg gcctgcccgt    900
cagccatgtg atccacgcgg cacatgcaca cacccctccg ccctgcccaa attttccaaa    960
atcccgccac agccctgcg ccaccgcttt tgcgcggatg acctcgggcg tctcgaaacc    1020
gcgagcacgc ccctccgcca ctcatacgcg ggcggccgca gctataggtg tacatttggg    1080
gcgggcctaa tgggtcggcc cgaagcacgg aaaaagcat gacccaggca cgtcacgaca    1140
cgaaatattt tagtgtcggg ccggcatggc ccgatatatc gggccgggtt tgggccgagg    1200
tcgcggccca tgggcgggca cgagcacggc ctgtttaagg caggcacgaa aaggctcata    1260
tatttattaa aatcacactt cattccacac tttcatgtac ttgataaaga acacaaagct    1320
agagataatg ttagttagtt gttttttgta gctttgaatt agagtatgtg atgtaatttt    1380
atttttgtta tgaacattag ataatgaact gaacttacga actttatata gagctgatta    1440
tactcttttt ctttctaaaa aagtgatttg taaacgaggt agtcattgca tagctctagc    1500
aacttaatac aattattaag tttgcttttg gtcaaattta tttgtcttat ttttttattt    1560
ttttattaaa tttgttttga attttgggct ctcatgtgaa tttcgggtcc tgatgtgaat    1620
tccaggccaa aaattgaatt tcgggcccta atgtgaattt cggcttttta tagtttcggg    1680
ccgcccgaaa tgagcccgac acgtttaagc aattacgggc cgggccgtgg gctgcccgtc    1740
atggcccgaa attcaaataa tacaggcctt ttcgggcttg gccaggctg gacggcccga    1800 atatacacct atagccgtag ccctggccgt cgtagcggat cacaggatga caaccgggtc    1860
ccgcgcctgt ctggtctaac gggacagtgg gcaatgtgcc cgtggttacg gtgaccgaat    1920 ttttttgcatt ttggtccttc atcggaaaaa aattcacgtt tggaccctag aaaatttaa    1980 tgttattttt ggactcttta ctcggcgccg taggctatgg cgccgagctg tgttacctcg    2040
```

```
gcgccacatg ctacagcgcc gagtaaaggg tccaaaaatg aaattaaaat tttctagggt    2100
ctaaacgtga atttttttcc gatgaagaac caaaatgcaa aaaaaattcg gttgcggtga    2160
gaaaaggtct aggccggtac gggaattcaa attgggaggc gggtgcgggc cctcgctgcg    2220
cgggcagaat cgctgatacg cccttgggcc acgccttcct tcgtatcccg tgcgcctgcc    2280
ctgccctcct gcagcgcccg tcgcctccct ttcccctttc ctccctctcc ccgcgagccg    2340
ccagaggcaa tttctccctc gattcgaccc cgattcgtcc gcccgcgacc gggattccct    2400
ccgccaagcg cggatctgaa cgctgcgctc cgtgtcgccc ctcgaatccg cc           2452

<210> SEQ ID NO 73
<211> LENGTH: 3892
<212> TYPE: DNA
<213> ORGANISM: Zea mays

<400> SEQUENCE: 73
actacgagtg cttaccttct tttcctttgc catgaggcaa gtgtgatgct cattggggaa      60
aagagccgac ttgttgaagg ccgaggcgac gagtccttcg ttgtcggagt cggacgagga    120
gcaatccgag tcccactcct ttccaaggtg tgcctcgccc ttcgcctttt tgtaggcttt    180
cttcttttcc cacttcccgc tctttccttg ttcttggtca ctatcattat cgggacaatt    240
agcaataaag tgaccaatct taccacactt gaagcaggag tgctttccct tcgtcttgct    300
cttgttggga tgctccttgc gacctttgag cgccgtcttg aagcgcttga tgatggggc     360 catttcatcc tcatttagcc cggccgcctc gacttgcgcc accttgttag gtagcgcctc    420
cctgctactt gttgctttga gagcaacagt ttgaggctcg tggattgggc cattcaatgc    480
ctcatcaaca tatcttgcct ccttgatcat cattcgctcg cttacaaact ttccgagtat    540
ttcctcgggc gtcatcttga tgtacctagg attctcacga atagagttta caagatgagg    600
atcaaagaca gtgaaggacc ttagcataag tcggacgacg tcgtggtccg tccatctcgt    660
actcccatag ctccttatct tgttgaccag ggtcttgagc ctattgtacg tttgagttgg    720
ctcctctccc gtgatcatcg cgaaccttcc tagttcgcct tccaccaact ccatcttggt    780
gagcatgttg gcgttgttcc cctcatgcga gatcttgagg gtgtcctaga tctgcttggc    840
gttatccaag ccgctcacct tattgtattc ttccctgcac aaagatgcta aagaacagt     900 agtagcttgt gcatttttat ggatttgttc attgataaac atagaattat ccgaactatc    960
aaattgcatt ccattttcta ctatctccca aatacttgga tgaagagaga gcaaatggct   1020
acgcattttg tgactccaaa atccacagtc ctctccatca aagtgtggag gtttaccaag   1080
tggaatggaa agcaaatgag cattggaatt atgcggaata cgaaataat cgaaagaaaa    1140 gttcgagtta aacattttat ttttctcctc gtgttcatcg tccttttgag acaaggaaga   1200
ttcgtcgctg tcgtggtaga caatcttctt gatgcgcctc ttcttctttc catccttctt   1260
cttttgactc gagccagagt cattggcttt gtcgtccctt ggctcgttga agatggacta   1320
cttctcattg tcattgacca ccatcccctt tcccttagga tccatctatt cgggcgatta   1380
gtccctttct tgaagagaac ggctctgata ccaattgaga gcacctagag gggggggggg   1440
tgaataggta atcctgtaaa aacttgaaac ttatagccac aaaacttggt taagtgttag   1500
taggttgaat agcgagctct tgtgaacaca agtatcacag aaaagcaatc acaaaagaca   1560
cgcaagttat cccgtggttc ggccaagtac aacacttgcc tagtccacgt tgtggcgtcc   1620
caatggacga gggttgcact caaccccttt caagtgatcc aaagatccac ttgaatacca   1680
```

-continued

```
cgatgttctt ctttctttac tctttctcgt ttgcgaggaa tctccacaac ttggagtctc    1740
tcgcccttac aataaggatc aaagtgaaag cactagagta agggaggaaa gcaacacaca    1800
caaatctcaa aagcaacagc acaaaacacg cacactagtc acaacttgag ctctaagttc    1860
acacacgaag ttctcaactc aagaggagct caaattgcta tcacaaagaa tcaaatgcgc    1920
tagaatggag tcttggtgct tagagatgat caaagaatgc ttggtgtgct cctccatgcg    1980
cctaggggtc cctttatag ccccaagtca gctaggagcc gttgagagca atccaggaag    2040
gctatccttg ccttctgtcg agtggtgcac cggacagtcc ggtgcaccac catacactgt    2100
ccggtgctga ttgctttcct attctggcgc agccgaccgt tgaagatttg agccgttgg    2160
cgcaccggac actgtccggc gcacaccgga cagtacggtg cccccatcag accgttggct    2220
cggctacgcg tcacgcgcgg attgcgcggc cgaccgttgg cgcagtcgac cgttggctca    2280
ccggacagtc cggtgcacca ccggacagtc cggtgaattt tagccgtaca ccgttgatca    2340
cttcccgaga gcgacgactt cgccgtggat ggctcaccgg acagtccggt gatttatagc    2400
catacaacgc cgtcgagtcc tgagagcgga tgttcaccga gactggtcct ggcgcaccgg    2460
acactgtccg gtgcacaacc ggacagtccg gtgcacccaa accgaaacta cctttggctg    2520
aacacagcca actcttttcc aaattgtttt ctcctgtttc tagcacttag acacaataca    2580
ttagtcttca aaacaatgta ctaagtctag aaacatacct ttgtgttgat tcgcacttca    2640
tccaccattt ggcactgttt aacacttaaa catttgtgtt ggcacttaat caccaaaata    2700
cttagaaatg gcccaagggc acatttccct ttcaatggga tattcagaaa acttggatgc    2760
ttgaagttgt ggtggttcgg ggtatttata gccctcaacc accaaggtag ccgttggaga    2820
ggctgctgtc gataggcgca ccggacagtc cggtgcgcca ccggacactc actgttcagt    2880
gtccggtgcg ccaccacgtc acccagccgt tagggttctg gagcagtcga ccgttggtgc    2940
cttttgtctgc ttgtggcact ggacagtctg gtggtgcacc ggacagtccg gtgcccctct    3000
gactcgcagc tctgacttct gccgtgacac tgtagcgctg tcagagtcgt ccgttgcgcg    3060
taggtagccg ttaccccgct ggctcaccgg acagtccgat gaattatagc ggagcgtgcc    3120
tacgttttcc cgagagtgac tgcttggctc ctgtacggcc ctggtgcacc ggacactgtc    3180
cggtgcgcca gaccacagca cactcaagtc ccttttgatc cttttgaatt gggttcctaa    3240
cttgaatatt ttattggttt gtgttgaacc ttatgcacct gtaatacatg agttctagag    3300
caaactagtt agtccatatg tttatgttgg acattcaacc actaaaatta attgtaggaa    3360
aatgttaacc ttatttgatt atttcccttt caattagcct atgctattta tcatggcttt    3420
aagttgttcc aatggatgtg aaaagtgcct tcctcaacga tactgtcaag gaagaagttt    3480
atgctgagca acctcacgac tttgaagaag gtgagtatcc ctctcatatt tataagctct    3540
aaaaaatgtt ttacgcttaa gcaattaagc caagggcatg atatgaatgt ctaaaacact    3600
ttcttattac taatagtttt aaagttggta aaacggacat tactttttt aataagactt    3660
gtttttatgc taaatctatg ttgatgatat tatcgtaccc acgtcaacaa tagatcttca    3720
ctgacaaccg gtcccagcac gtccagtctc acctgtcata cgcggttccg tccccttcgc    3780
cccccgtttg ggctcagaa gcttcccctt ccgtctccat atcttcttct tggtccgccg    3840
tctccactcc gcgttccctg gctccctgcg ttgcgtcttg ggggagagag ag           3892
```

<210> SEQ ID NO 74
<211> LENGTH: 1257
<212> TYPE: DNA
<213> ORGANISM: Zea mays

<400> SEQUENCE: 74

```
atccaagttt aatggagact cctggacttg gacacatgtt ttttgtctat tgaataattg      60
agcgttactc attgcacgtg ttttgttacc taggtatatg cgtcgagtcc agcggtgtgt     120
gttgaccgaa taattgtacc tatttggttt ccttcgtgat gggctaagga ttgcagccgt     180
gagtgcaagg tattttagag ggcgttggtt gcatgcgtag agatgggct agacccaata      240
tcgatgtgca agctagggtc gccctgcgtg tatttgtcta agcaagcaac acatagtcag     300
tgaacccctt tgtagtttgt aattgtttat caaatcacta actcagtaag gccttgttcg     360
gtaattccta ttgttgggga ggagaccgag tacaacctca tcgtagagcg aagaccatgt     420
taggcggaga ctaaactcac cctcgttcta aactaacaaa gaccctactt cgccatcaat     480
tgccttcgca ggttccttgg tgcatggatt ccgaccaaag agacctccga tggaacgggc     540
ccgacattga ggggttgcgc cggacggcag ccagatgacc acgacttcgc cacgcccggg     600
gagtgaagtc ctcgtcaccc atgcgatgtg gagccctcgc tcaacctccg tttggcccag     660
ttggtcgaag gggaattggg gacttccctg tgctctggag gcgactcctt cactaccgca     720
caaccagccg tcgattgagg gaaagttagc atgaagacat ttgaggacac cgacaacagt     780
tatacttcgt gctgttcgac acggttcttc atagggcgca ctcagaccca cctgtcagcg     840
gaacgcgtgg gtctgtatga atgcactgt aattacctcg ttacatagaa tattacttaa      900
tatactttgg accaattgcg aaagaaaacg gaggatgagt tggccattag cgaacacaag     960
atatagccca cgcggcccac accccatcca catcaccgtt cggatcggac ggtcagtaat    1020
ctcgcgtggg acgaaagcta gccggctacc atccgtcggc cacaactcct gcgtccattc    1080
aaagctatca agccccgcag tcgcgagtaa agaacaacag caggccaccg ctgctataaa    1140
accctccgcc tccaccggcg gctcgccaaa ctccgtttcg aattctaggg ttttgctgct    1200
ctccgacccc gagctccgaa ggccgcagca tcaggcgcgg ccccctcgc gtgtgac       1257
```

<210> SEQ ID NO 75
<211> LENGTH: 1148
<212> TYPE: DNA
<213> ORGANISM: Zea mays

<400> SEQUENCE: 75

```
gtgtgaccaa ctttagttat ttgacgtttt ttaattagtt gtttgacgat ttttagtttt      60
ttttgctatt cctaccaatt ttcaggtgta agtgcacatt tccgggctta catacaagca     120
taggagaaac tacagatgga catagcaact tccactgatt tgcttggtgt tgaaaccaga     180
agcacaggct tcattttctc cattggaaaa gaacctatga aaacccgtcc ttcagtgttt     240
gctctgggtg aacgaataaa cattttgaag gcgaagttat tagcacttcc attcagatga     300
tgacataggc cccgtttggt tagggtgac taaaatttag tgactaaatt ttagttactt      360
ttagtcccta agaaacaaa catggtgact agaatgtggt gactaaactt tagttctta      420
gtcaccaagg ggtgactaaa agggactaaa gtaaattttt taccttattt gccctctcaa     480
ctttcttctt atagcaaaca tccattaatt aatagaggta aaacagtcat tattcacagc     540
aattaatgct cattagtccg gtttagtcac tggaaccaaa cagagtactt tagcgactaa     600
actttagtca ttaaaatcta atctagtgac taaaggaacc aaacagagcc ataatgttta     660
gaattttgaa gttcataaat ggctcaatca tggtagtggg agcttaactc agttattgtg     720
ctacagggtg catatatcca gaagttctta cactgttaat aagatgttta atttgtagac     780
```

-continued

| | | | | | |
|---|---|---|---|---|---|
| aaaatttgcc | atcgtagcat | agccaatatg | ctcagtctga | actgtttgat | tattttcatg | 840
| tctggagatc | tcagcttctt | tgtatctgtt | gttgcaccca | tgaagcggta | acaatttttt | 900
| tcgaaaacga | aaaaggaaaa | ccattatgcg | tttccgagta | tcgagcgtct | ccttgacgcg | 960
| ggcgcccggg | gccatctcca | ccgtcagtgg | cgagatcgga | cggcctgctg | gaggtgttgg | 1020
| gcccatccgt | ccccgggtac | tgggaccacc | gatccctctt | caatacaaaa | ccagccgcag | 1080
| ttctccattt | tcgagcgcag | aagcgagaga | gatccggagc | agccgcagtc | ccaccgaccc | 1140
| cgccgccg | | | | | | 1148

PLANT REGULATORY SEQUENCES FOR CONTROL OF GENE EXPRESSION

This application claims the benefit of U.S. Provisional Application No. 60/154,182 filed Sep. 16, 1999.

FIELD OF THE INVENTION

The present invention relates to the isolation and use of nucleic acid molecules for control of gene expression in plants, specifically novel plant promoters.

BACKGROUND OF THE INVENTION

One of the goals of plant genetic engineering is to produce plants with agronomically important characteristics or traits. Recent advances in genetic engineering have provided the requisite tools to transform plants to contain and express foreign genes (Kahl et al. (1995) World Journal of Microbiology and Biotechnology 11:449–460). Particularly desirable traits or qualities of interest for plant genetic engineering would include but are not limited to resistance to insects and other pests and disease-causing agents, tolerances to herbicides, enhanced stability, yield, or shelf-life, environmental tolerances, and nutritional enhancements. The technological advances in plant transformation and regeneration have enabled researchers to take pieces of DNA, such as a gene or genes from a heterologous source, or a native source, but modified to have different or improved qualities, and incorporate the exogenous DNA into the plant's genome. The gene or gene(s) can then be expressed in the plant cell to exhibit the added characteristic(s) or trait(s). In one approach, expression of a novel gene that is not normally expressed in a particular plant or plant tissue may confer a desired phenotypic effect. In another approach, transcription of a gene or part of a gene in an antisense orientation may produce a desirable effect by preventing or inhibiting expression of an endogenous gene.

Isolated plant promoters are useful for modifying plants through genetic engineering to have desired phenotypic characteristics. In order to produce such a transgenic plant, a vector that includes a heterologous gene sequence that confers the desired phenotype when expressed in the plant is introduced into the plant cell. The vector also includes a plant promoter that is operably linked to the heterologous gene sequence, often a promoter not normally associated with the heterologous gene. The vector is then introduced into a plant cell to produce a transformed plant cell, and the transformed plant cell is regenerated into a transgenic plant. The promoter controls expression of the introduced DNA sequence to which the promoter is operably linked and thus affects the desired characteristic conferred by the DNA sequence.

Since the promoter is a 5' regulatory element that plays an integral part in the overall expression of a gene or gene(s), it would be advantageous to have a variety of promoters to tailor gene expression such that a gene or gene(s) is transcribed efficiently at the right time during plant growth and development, in the optimal location in the plant, and in the amount necessary to produce the desired effect. In one case, for example, constitutive expression of a gene product may be beneficial in one location of the plant, but less beneficial in another part of the plant. In other cases, it may be beneficial to have a gene product produced at a certain developmental stage of the plant, or in response to certain environmental or chemical stimuli. The commercial development of genetically improved germplasm has also advanced to the stage of introducing multiple traits into crop plants, often referred to as a gene stacking approach. In this approach, multiple genes conferring different characteristics of interest can be introduced into a plant. It is important when introducing multiple genes into a plant, that each gene is modulated or controlled for optimal expression and that the regulatory elements are diverse, to reduce the potential of gene silencing which can be caused by recombination of homologous sequences. In light of these and other considerations, it is apparent that optimal control of gene expression and regulatory element diversity are important in plant biotechnology.

The proper regulatory sequences must be present and in the proper location with respect to the DNA sequence of interest, for the newly inserted DNA to be transcribed and thereby, if desired translated into a protein in the plant cell. These regulatory sequences include but are not limited to a promoter, a 5' untranslated leader, and a 3' polyadenylation sequence. The ability to select the tissues in which to transcribe such foreign DNA, and the time during plant growth in which to obtain transcription of such foreign DNA is also possible through the choice of appropriate promoter sequences that control transcription of these genes.

A variety of different types or classes of promoters can be used for plant genetic engineering. Promoters can be classified on the basis of range or tissue specificity. For example, promoters referred to as constitutive promoters are capable of transcribing operatively linked DNA sequences efficiently and expressing said DNA sequences in multiple tissues. Tissue-enhanced or tissue-specific promoters can be found upstream and operatively linked to DNA sequences normally transcribed in higher levels in certain plant tissues or specifically in certain plant tissues. Other classes of promoters would include but are not limited to inducible promoters which can be triggered by external stimuli such as chemical agents, developmental stimuli, or environmental stimuli. Thus, the different types of promoters desired can be obtained by isolating the upstream 5' regulatory regions of DNA sequences which are transcribed and expressed in a constitutive, tissue-enhanced, or inducible manner.

The technological advances of high-throughput sequencing and bioinformatics has provided additional molecular tools for promoter discovery. Particular target plant cells, tissues, or organs at a specific stage of development, or under particular chemical, environmental, or physiological conditions can be used as source material to isolate the mRNA and construct cDNA libraries. The cDNA libraries are quickly sequenced and the expressed sequences catalogued electronically. Using sequence analysis software, thousands of sequences can be analyzed in a short period, and sequences from selected cDNA libraries can be compared. The combination of laboratory and computer-based subtraction methods allows researchers to scan and compare cDNA libraries and identify sequences with a desired expression profile. For example, sequences expressed preferentially in one tissue can be identified by comparing a cDNA library from one tissue to cDNA libraries of other tissues and electronically "subtracting" common sequences to find sequences only expressed in the target tissue of interest. The tissue enhanced sequence can then be used as a probe or primer to clone the corresponding full-length cDNA. A genomic library of the target plant can then be used to isolate the corresponding gene and the associated regulatory elements, including promoter sequences.

Multiple promoter sequences which confer a desired expression profile such as promoters capable of regulating expression of operably linked genes in multiple tissues can be isolated by selectively comparing cDNA libraries of target tissues of interest with non-target or background cDNA libraries to find the 5' regulatory regions associated with the expressed sequences in those target libraries. The isolated promoter sequences can be used for selectively modulating expression of any operatively linked gene and provide additional regulatory element diversity in a plant expression vector in gene stacking approaches.

SUMMARY OF THE INVENTION

The present invention provides nucleic acid sequences, which comprise regulatory sequences located upstream of the 5' end of plant DNA structural coding sequences that are transcribed in multiple tissues of interest and shown in SEQ ID NOS: 53–75.

In one aspect, the present invention provides nucleic acid sequences comprising a sequence selected from the group consisting of SEQ ID NOS: 53–75 or any fragments, regions, or cis elements of the sequence that are capable of regulating transcription of operably linked DNA sequences.

The present invention also provides nucleic acid sequences comprising a sequence selected from the group consisting of SEQ ID NOS: 53–75 that are promoters.

Another aspect of the present invention relates to the use of at least one fragment, region, or cis element thereof of the disclosed 5' promoter sequences that can be combined to create novel promoters or used in a novel combination with another heterologous regulatory sequence to create a hybrid or chimeric promoter capable of modulating transcription of an operably linked DNA sequence.

Hence, the present invention relates to the use of nucleic acid sequences disclosed in SEQ ID NOS: 53–75, or any fragment, region, or cis elements of the disclosed sequences that are capable of regulating transcription of a DNA sequence when operably linked to the DNA sequence. Therefore, the invention not only encompasses the sequences as disclosed in SEQ ID NOS: 53–75, but also includes any truncated or deletion derivatives, or fragments or regions thereof which are capable of functioning independently as a promoter including cis elements that are capable of functioning as regulatory sequences in conjunction with one or more regulatory sequences when operably linked to a transcribable sequence.

The present invention thus encompasses a novel promoter or a hybrid or chimeric promoter comprising a nucleic acid of SEQ ID NOS: 53–75. The hybrid or chimeric promoters can consist of any length fragments, regions, or cis elements of the disclosed sequences of SEQ ID NOS: 53–75 combined with any other transcriptionally active minimal or full-length promoter. For example, a promoter sequence selected from SEQ ID NOS: 53–75 may be combined with a CaMV 35S or other promoter to construct a novel hybrid promoter. A minimal promoter can also be used in combination with the nucleic acid sequences of the present invention. A novel promoter also comprises any promoter constructed by engineering the nucleic acid sequences disclosed in SEQ ID NOS: 53–75 or any fragment, region, or cis element of the disclosed sequences in any manner sufficient to transcribe an operably linked DNA sequence.

Another aspect of the present invention relates to the ability of the promoter sequences of SEQ ID NOS: 53–75, or fragments, regions, or cis elements thereof to regulate transcription of operably linked transcribable sequences in multiple tissues. Fragments, regions, or cis elements of SEQ ID NOS: 53–75 that are capable of regulating operably linked DNA sequences in certain tissues may be isolated from the disclosed nucleic acid sequences of SEQ ID NOS: 53–75 and used to engineer novel promoters that confer a desired expression profile.

The present invention also encompasses DNA constructs comprising the disclosed sequences as shown in SEQ ID NOS: 53–75 or any fragments, regions, or cis elements thereof, including novel promoters generated using the disclosed sequences or any fragment, region, or cis element of the disclosed sequences.

The present invention also includes any cells and transgenic plants containing the DNA disclosed in the sequences as shown in SEQ ID NOS: 53–75, or any fragments, regions, or cis elements thereof.

The present invention also provides a method of regulating transcription of a DNA sequence comprising operably linking the DNA sequence to any promoter comprising a nucleic acid comprising all or any fragment, region or cis element of a sequence selected from the group consisting of SEQ ID NOS: 53–75.

In a another embodiment the present invention provides a method regulating expression of DNA sequences in multiple tissues by operably linking a sequence selected from the group consisting of SEQ ID NOS: 53–75, or any fragment, region, or cis element of the disclosed sequences to any transcribable DNA sequence. The fragments, regions, or cis elements of the disclosed promoters as shown in SEQ ID NOS: 53–75 can be engineered and used independently in novel combinations including multimers, or truncated derivatives and the novel promoters can be operably linked with a transcribable DNA sequence. Alternatively the disclosed fragments, regions, or cis elements of the disclosed sequences can be used in combination with a heterologous promoter including a minimal promoter to create a novel hybrid or chimeric promoter and the novel hybrid promoter can be operably linked to a transcribable DNA sequence.

The present invention also provides a method of making a transgenic plant by introducing into the cell of a plant a DNA construct comprising: (i) a promoter comprising a nucleic acid comprising a sequence selected from the group consisting of SEQ ID NOS: 53–75, or fragments, regions, or cis elements thereof, and operably linked to the promoter, (ii) a transcribable DNA sequence and (iii) a 3' untranslated region.

The present invention also provides a method of isolating at least one 5' regulatory sequence of a desired expression profile from a target plant of interest by evaluating a collection of nucleic acid sequences of expressed sequence tags (ESTs) derived from one or more cDNA libraries prepared from a plant cell type of interest, comparing EST sequences from at least one target plant cDNA library and one or more non-target cDNA libraries of ESTs from a different plant cell type, subtracting common EST sequences found in both target and non-target libraries, designing gene-specific primers from the remaining ESTs after the subtractions which are representative of the targeted expressed sequences, and isolating the corresponding 5' flanking and regulatory sequences, which includes promoter sequences from a genomic library prepared from the target plant using the gene specific primers.

The foregoing and other aspects of the invention will become more apparent from the following detailed description and accompanying drawings.

DETAILED DESCRIPTION OF THE INVENTION

Definitions and Methods

Figure 1:
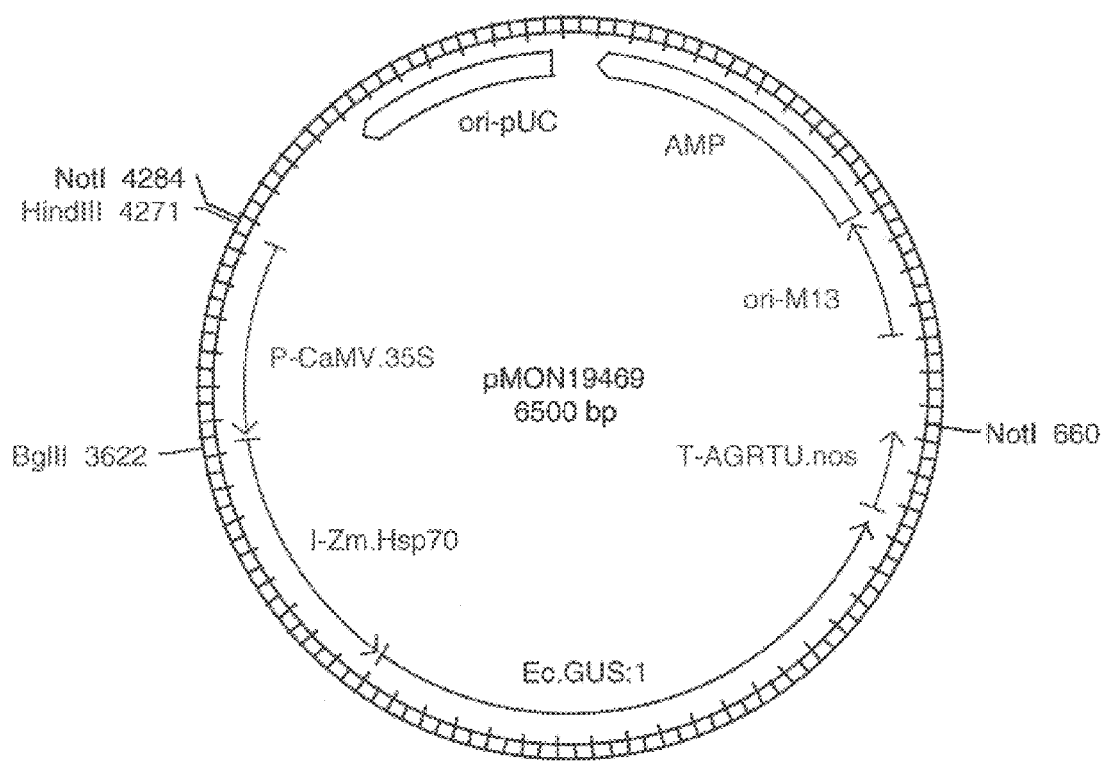
FIG. 1 is a plasmid map of pMON19469

The following definitions and methods are provided to better define the present invention and to guide those of ordinary skill in the art in the practice of the present invention. Unless otherwise noted, terms are to be understood according to conventional usage by those of ordinary skill in the relevant art. The nomenclature for DNA bases as set forth at 37 CFR §1.822 is used. The standard one- and three-letter nomenclature for amino acid residues is used.

"Nucleic acid (sequence)" or "polynucleotide (sequence)" refers to single- or double-stranded DNA or RNA of genomic or synthetic origin, i.e., a polymer of deoxyribonucleotide or ribonucleotide bases, respectively, read from the 5' (upstream) end to the 3' (downstream) end. The nucleic acid can represent the sense or complementary (antisense) strand.

"Native" refers to a naturally occurring ("wild-type") nucleic acid sequence.

"Heterologous" sequence refers to a sequence which originates from a foreign source or species or, if from the same source, is modified from its original form.

An "isolated" nucleic acid sequence is substantially separated or purified away from other nucleic acid sequences with which the nucleic acid is normally associated in the cell of the organism in which the nucleic acid naturally occurs, i.e., other chromosomal or extrachromosomal DNA. The term embraces nucleic acids that are biochemically purified so as to substantially remove contaminating nucleic acids and other cellular components. The term also embraces recombinant nucleic acids and chemically synthesized nucleic acids.

The term "substantially purified, as used herein, refers to a molecule separated from substantially all other molecules normally associated with it in its native state. More preferably, a substantially purified molecule is the predominant species present in a preparation. A substantially purified molecule may be greater than 60% free, preferably 75% free, more preferably 90% free from the other molecules (exclusive of solvent) present in the natural mixture. The term "substantially purified" is not intended to encompass molecules present in their native state.

A first nucleic acid sequence displays "substantially identity" to a reference nucleic acid sequence if, when optimally aligned (with appropriate nucleotide insertions or deletions totaling less than 20 percent of the reference sequence over the window of comparison) with the other nucleic acid (or its complementary strand), there is at least about 75% nucleotide sequence identity, preferably at least about 80% identity, more preferably at least about 85% identity, and most preferably at least about 90% identity over a comparison window of at least 20 nucleotide positions, preferably at least 50 nucleotide positions, more preferably at least 100 nucleotide positions, and most preferably over the entire length of the first nucleic acid. Optimal alignment of sequences for aligning a comparison window may be conducted by the local homology algorithm of Smith and Waterman Adv. Appl. Math. 2:482, 1981; by the homology alignment algorithm of Needleman and Wunsch, J. Mol. Biol. 48:443, 1970; by the search for similarity method of Pearson and Lipman, Proc. Natl. Acad. Sci. USA 85:2444, 1988; preferably by computerized implementations of these algorithms (GAP, BESTFIT, FASTA, and TFASTA in the Wisconsin Genetics Software Package Release 7.0, Genetics Computer Group, 575 Science Dr., Madison, Wis. The reference nucleic acid may be a full-length molecule or a portion of a longer molecule. Alternatively, two nucleic acids are have substantial identity if one hybridizes to the other under stringent conditions, as defined below.

A first nucleic acid sequence is "operably linked" with a second nucleic acid sequence when the sequences are so arranged that the first nucleic acid sequence affects the function of the second nucleic-acid sequence. Preferably, the two sequences are part of a single contiguous nucleic acid molecule and more preferably are adjacent. For example, a promoter is operably linked to a gene if the promoter regulates or mediates transcription of the gene in a cell.

A "recombinant" nucleic acid is made by an artificial combination of two otherwise separated segments of sequence, e.g., by chemical synthesis or by the manipulation of isolated segments of nucleic acids by genetic engineering techniques. Techniques for nucleic-acid manipulation are well-known (see, e.g., Sambrook et al., Molecular Cloning, A Laboratory Manual, 2nd Ed., Cold Spring Harbor Press, Cold Spring Harbor, N.Y., 1989, and Ausubel et al., 1992).

Methods for chemical synthesis of nucleic acids are discussed, for example, in Beaucage and Carruthers, Tetra. Letts. 22:1859–1862, 1981, and Matteucci et al., J. Am. Chem. Soc. 103:3185, 1981. Chemical synthesis of nucleic acids can be performed, for example, on commercial automated oligonucleotide synthesizers.

A "synthetic nucleic acid sequence" can be designed and chemically synthesized for enhanced expression in particular host cells and for the purposes of cloning into appropriate vectors. Host cells often display a preferred pattern of codon usage (Murray et al., 1989). Synthetic DNAs designed to enhance expression in a particular host should therefore reflect the pattern of codon usage in the host cell. Computer programs are available for these purposes including but not limited to the "BestFit" or "Gap" programs of the Sequence Analysis Software Package, Genetics Computer Group, Inc., University of Wisconsin Biotechnology Center, Madison, Wis. 53711.

"Amplification" of nucleic acids or "nucleic acid reproduction" refers to the production of additional copies of a nucleic acid sequence and is carried out using polymerase chain reaction (PCR) technologies. A variety of amplification methods are known in the art and are described, inter alia, in U.S. Pat. Nos. 4,683,195 and 4,683,202 and in PCR Protocols: A Guide to Methods and Applications, ed. Innis et al., Academic Press, San Diego, 1990. In PCR, a primer refers to a short oligonucleotide of defined sequence which is annealed to a DNA template to initiate the polymerase chain reaction.

"Transformed", "transfected", or "transgenic" refers to a cell, tissue, organ, or organism into which has been introduced a foreign nucleic acid, such as a recombinant vector. Preferably, the introduced nucleic acid is integrated into the genomic DNA of the recipient cell, tissue, organ or organism such that the introduced nucleic acid is inherited by subsequent progeny. A "transgenic" or "transformed" cell or organism also includes progeny of the cell or organism and progeny produced from a breeding program employing such a "transgenic" plant as a parent in a cross and exhibiting an altered phenotype resulting from the presence of a recombinant construct or vector.

The term "gene" refers to chromosomal DNA, plasmid DNA, cDNA, synthetic DNA, or other DNA that encodes a peptide, polypeptide, protein, or RNA molecule, and regions flanking the coding sequence involved in the regulation of expression. Some genes can be transcribed into mRNA and translated into polypeptides (structural genes); other genes can be transcribed into RNA (e.g. rRNA, tRNA); and other types of gene function as regulators of expression (regulator genes).

"Expression" of a gene refers to the transcription of a gene to produce the corresponding mRNA and translation of this mRNA to produce the corresponding gene product, i.e., a peptide, polypeptide, or protein. Gene expression is controlled or modulated by regulatory elements including 5' regulatory elements such as promoters.

"Genetic component" refers to any nucleic acid sequence or genetic element that may also be a component or part of an expression vector. Examples of genetic components include, but are not limited to promoter regions, 5' untranslated leaders, introns, genes, 3' untranslated regions, and other regulatory sequences or sequences which affect transcription or translation of one or more nucleic acid sequences.

The terms "recombinant DNA construct", "recombinant vector", "expression vector" or "expression cassette" refer to any agent such as a plasmid, cosmid, virus, BAC (bacterial artificial chromosome), autonomously replicating sequence, phage, or linear or circular single-stranded or double-stranded DNA or RNA nucleotide sequence, derived from any source, capable of genomic integration or autonomous replication, comprising a DNA molecule in which one or more DNA sequences have been linked in a functionally operative manner.

"Complementary" refers to the natural association of nucleic acid sequences by base-pairing (A-G-T pairs with the complementary sequence T-C-A). Complementarity between two single-stranded molecules may be partial, if only some of the nucleic acids pair are complementary; or complete, if all bases pair are complementary. The degree of complementarity affects the efficiency and strength of hybridization and amplification reactions.

"Homology" refers to the level of similarity between nucleic acid or amino acid sequences in terms of percent nucleotide or amino acid positional identity, respectively, i.e., sequence similarity or identity. Homology also refers to the concept of similar functional properties among different nucleic acids or proteins.

"ESTs" or Expressed Sequence Tags are short sequences of randomly selected clones from a cDNA (or complementary DNA) library which are representative of the cDNA inserts of these randomly selected clones (McCombie, et al., Nature Genetics, 1:124, 1992; Kurata, et al., Nature Genetics, 8: 365,1994; Okubo, et al., Nature Genetics, 2: 173, 1992).

The term "electronic Northern" refers to a computer-based sequence analysis which allows sequences from multiple cDNA libraries to be compared electronically based on parameters the researcher identifies including abundance in EST populations in multiple cDNA libraries, or exclusively to EST sets from one or combinations of libraries.

"Subsetting" refers to any method of comparing nucleic acid sequences from different or multiple sources which can be used to identify the profile of the nucleic acid sequences which reflects gene transcription activity and message stability in a particular tissue, at a particular time, or under particular conditions.

"Promoter" refers to a nucleic acid sequence located upstream or 5' to a translational start codon of an open reading frame (or protein-coding region) of a gene and that is involved in recognition and binding of RNA polymerase II and other proteins (trans-acting transcription factors) to initiate transcription. A "plant promoter" is a native or non-native promoter that is functional in plant cells. Constitutive promoters are functional in most or all tissues of a plant throughout plant development. Tissue-, organ- or cell-specific promoters are expressed only or predominantly in a particular tissue, organ, or cell type, respectively. Rather than being expressed "specifically" in a given tissue, organ, or cell type, a promoter may display "enhanced" expression, i.e., a higher level of expression, in one part (e.g., cell type, tissue, or organ) of the plant compared to other parts of the plant. Temporally regulated promoters are functional only or predominantly during certain periods of plant development or at certain times of day, as in the case of genes associated with circadian rhythm, for example. Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, flooding or drought, phytohormones, wounding, or chemicals such as ethanol, jasmonate, salicylic acid, or safeners.

Any plant promoter can be used as a 5' regulatory sequence for modulation expression of a particular gene or genes. One preferred promoter would be a plant RNA polymerase II promoter. Plant RNA polymerase II promoters, like those of other higher eukaryotes, have complex structures and are comprised of several distinct elements. One such element is the TATA box or Goldberg-Hogness box, which is required for correct expression of eukaryotic genes in vitro and accurate, efficient initiation of transcription in vivo. The TATA box is typically positioned at approximately −25 to −35, that is, at 25 to 35 basepairs (bp) upstream (5') of the transcription initiation site, or cap site, which is defined as position +1 (Breathnach and Chambon, Ann. Rev. Biochem. 50:349–383, 1981; Messing et al., In: Genetic Engineering of Plants, Kosuge et al., eds., pp. 211–227, 1983). Another common element, the CCAAT box, is located between −70 and −100 bp. In plants, the CCAAT box may have a different consensus sequence than the functionally analogous sequence of mammalian promoters (the plant analogue has been termed the "AGGA box" to differentiate it from its animal counterpart; Messing et al., In: Genetic Engineering of Plants, Kosuge et al., eds., pp. 211–227, 1983). In addition, virtually all promoters include additional upstream activating sequences or enhancers (Benoist and Chambon, Nature 290:304–310, 1981; Gruss et al., Proc. Nat. Acad. Sci. USA 78:943–947, 1981; and Khoury and Gruss, Cell 27:313–314, 1983) extending from around −100 bp to −1,000 bp or more upstream of the transcription initiation site.

When fused to heterologous DNA sequences, such promoters typically cause the fused sequence to be transcribed in a manner that is similar to that of the gene sequence with which the promoter is normally associated. Promoter fragments that include regulatory sequences can be added (for example, fused to the 5' end of, or inserted within, an active promoter having its own partial or complete regulatory sequences (Fluhr et al., Science 232:1106–1112, 1986; Ellis et al., EMBO J. 6:11–16, 1987; Strittmatter and Chua, Proc. Nat. Acad. Sci. USA 84:8986–8990, 1987; Poulsen and Chua, Mol. Gen. Genet. 214:16–23, 1988; Comai et al., Plant Mol. Biol. 15:373–381, 1991). Alternatively, heterologous regulatory sequences can be added to the 5' upstream region of an inactive, truncated promoter, e.g., a promoter including only the core TATA and, sometimes, the CCAAT elements (Fluhr et al., Science 232:1106–1112, 1986; Strittmatter and Chua, Proc. Nat. Acad. Sci. USA 84:8986–8990, 1987; Aryan et al., Mol. Gen. Genet. 225:65–71, 1991).

Promoters are typically comprised of multiple distinct "cis-acting transcriptional regulatory elements," or simply "cis-elements," each of which appears to confer a different aspect of the overall control of gene expression (Strittmatter and Chua, Proc. Nat. Acad. Sci. USA 84:8986–8990, 1987; Ellis et al., EMBO J. 6:11–16, 1987; Benfey et al., EMBO J. 9:1677–1684, 1990)."cis elements" bind trans-acting protein factors that regulate transcription. Some cis elements bind more than one factor, and trans-acting transcription factors may interact with different affinities with more than one cis element (Johnson and McKnight, Ann. Rev. Biochem. 58:799–839, 1989). Plant transcription factors, corresponding cis elements, and analysis of their interaction are discussed, for example, in: Martin, Curr. Opinions Biotech. 7:130–138, 1996; Murai, In: Methods in Plant Biochemistry and Molecular Biology, Dashek, ed., CRC Press, 1997, pp. 397–422; and Methods in Plant Molecular Biology, Maliga et al., eds., Cold Spring Harbor Press, 1995, pp. 233–300. The promoter sequences of the present invention can contain "cis elements" which can confer or modulate gene expression.

Cis elements can be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by sequence similarity with known cis element motifs by conventional sequence comparison methods. The fine structure of a cis element can be further studies by mutagenesis (or substitution) of one or more nucleotides or by other conventional methods. See, e.g., Methods in Plant Biochemistry and Molecular Biology, Dashek, ed., CRC Press, 1997, pp. 397–422; and Methods in Plant Molecular Biology, Maliga et al., eds., Cold Spring Harbor Press, 1995, pp. 233–300.

Cis elements can be obtained by chemical synthesis or by cloning from promoters that includes such elements, and they can be synthesized with additional flanking sequences that contain useful restriction enzyme sites to facilitate subsequence manipulation. In one embodiment, the promoters are comprised of multiple distinct "cis-acting transcriptional regulatory elements," or simply "cis-elements," each of which appears to confer a different aspect of the overall control of gene expression (Strittmatter and Chua, Proc. Nat. Acad. Sci. USA 84:8986–8990, 1987; Ellis et al., EMBO J. 6:11–16, 1987; Benfey et al., EMBO J. 9:1677–1684, 1990). In a preferred embodiment sequence regions comprising "cis elements" of the nucleic acid sequences of SEQ ID NOS: 53–75 are identified using computer programs designed specifically to identify cis elements, or domains or motifs within sequences.

The present invention includes cis elements of SEQ ID NOS: 53–75 or homologues of cis elements known to effect gene regulation that show homology with the nucleic acid sequences of the present invention. A number of such elements are known in the literature, such as elements which are regulated by numerous factors such as light, heat, or stress; elements which are regulated or induced by pathogens or chemicals, and the like. Such elements may either positively or negatively regulated gene expression, depending on the conditions. Examples of cis elements would include but are not limited to oxygen responsive elements (Cowen et al., J. Biol. Chem. 268(36):26904, 1993), light regulatory elements (see for example, Bruce and Quaill, Plant Cell 2(11): 1081. 1990, and Bruce et al., EMBO J. 10:3015, 1991, a cis element reponsive to methyl jasmonate treatment (Beaudoin and Rothstein, Plant Mol. Biol. 33:835, 1997, salicylic acid responsive elements (Strange et al., Plant J. 11:1315, 1997, heat shock response elements (Pelham et al., Trends Genet. 1:31, 1985, elements responsive to wounding and abiotic stress (Loace et al., Proc. Natl. Acad. Sci. U.S.A. 89:9230, 1992; Mhiri et al., Plant Mol. Biol. 33:257, 1997), low temperature elements (Baker et al., Plant Mol. Biol. 24:701, 1994; Jiang et al., Plant Mol. Biol. 30:679, 1996; Nordin et al., Plant Mol. Biol. 21:641, 1993; Zhou et al., J. Biol. Chem. 267:23515, 1992), and drought responsive elements, (Yamaguchi et al., Plant Cell 6:251–264, 1994; Wang et al., Plant Mol. Biol. 28:605, 1995; Bray E. A. Trends in Plant Science 2:48, 1997).

The present invention therefore encompasses fragments or "cis elements" of the disclosed nucleic acid molecules and the nucleic acid fragments can include any region of the disclosed sequences. The promoter regions or partial promoter regions of the present invention as shown in SEQ ID NOS: 53–75 can contain one or more regulatory elements including but not limited to "cis elements" or domains which are capable of regulating transcription of operably linked DNA sequences in multiple tissues.

Plant promoters can include promoters produced through the manipulation of known promoters to produce synthetic, chimeric, or hybrid promoters. Such promoters can also combine cis elements from one or more promoters, for example, by adding a heterologous regulatory sequence to an active promoter with its own partial or complete regulatory sequences (Ellis et al., EMBO J. 6:11–16, 1987; Strittmatter and Chua, Proc. Nat. Acad. Sci. USA 84:8986–8990, 1987; Poulsen and Chua, Mol. Gen. Genet. 214:16–23, 1988; Comai et al., Plant. Mol. Biol. 15:373–381, 1991). Chimeric promoters have also been developed by adding a heterologous regulatory sequence to the 5' upstream region of an inactive, truncated promoter, i.e., a promoter that includes only the core TATA and, optionally, the CCAAT elements (Fluhr et al., Science 232:1106–1112, 1986; Strittmatter and Chua, Proc. Nat. Acad. Sci. USA 84:8986–8990, 1987; Aryan et al., Mol. Gen. Genet. 225:65–71, 1991). The design, construction, and use of chimeric or hybrid promoters comprising at least one cis element of SEQ ID NOS: 53–75 for modulating the expression of operably linked nucleic acid sequences is also encompassed by the present invention.

The promoter sequences, fragments, regions or cis elements thereof of SEQ ID NOS: 53–75 are capable of transcribing operably linked DNA sequences in multiple tissues and can selectively regulate expression of genes in these tissues. For a number of agronomic traits, expression of a gene or genes of interest is desirable in multiple tissues in order to confer the desired characteristic(s). The availability of suitable promoters which regulate transcription of operably linked genes in selected target tissues of interest is important since it may not be desirable to have expression in every tissue, but only in certain tissues. For example, if one desires to control an insect pest which targets particular tissues, it would be of interest to express the desired gene product(s) in those tissues. For herbicide tolerance, it may be desirable to have a promoter which transcribes operably linked genes in a manner which confers herbicide tolerance at the desired levels in both vegetative and reproductive tissues. Consequently, it is important to have a wide variety of choices of 5' regulatory elements for any plant biotechnology strategy.

The advent of genomics, which comprises molecular and bioinformatics techniques, has resulted in rapid sequencing and analyses of a large number of DNA samples from a vast number of targets, including but not limited to plant species of agronomic importance. To identify the nucleic acid sequences of the present invention from a database or collection of cDNA sequences, the first step involves constructing cDNA libraries from specific plant tissue targets of interest. Briefly, the cDNA libraries are first constructed from these tissues that are harvested at a particular developmental stage, or under particular environmental conditions. By identifying differentially expressed genes in plant tissues at different developmental stages, or under different conditions, the corresponding regulatory sequences of those genes can be identified and isolated. Transcript imaging enables the identification of tissue-preferred sequences based on specific imaging of nucleic acid sequences from a cDNA library. By transcript imaging as used herein is meant an analysis which compares the abundance of expressed genes in one or more libraries. The clones contained within a cDNA library are sequenced and the sequences compared with sequences from publicly available databases. Computer-based methods allows the researcher to provide queries which compare sequences from multiple libraries. The process enables quick identification of clones of interest compared with conventional hybridization subtraction methods known to those of skill in the art.

Using conventional methodologies, cDNA libraries can be constructed from the mRNA (messenger RNA) of a given tissue or organism using poly dT primers and reverse transcriptase (Efstratiadis, et al., Cell 7:279, 1976; Higuchi, et al., Proc. Natl. Acad. Sci. (U.S.A.) 73:3146, 1976; Maniatis, et al., Cell 8:163, 1976; Land et al., Nucleic Acids Res. 9:2251, 1981; Okayama, et al., Mol. Cell. Biol. 2:161, 1982; Gubler, et al., Gene 25:263, 1983).

Several methods can be employed to obtain full-length cDNA constructs. For example, terminal transferase can be used to add homopolymeric tails of dC residues to the free 3' hydroxyl groups (Land, et al., Nucleic Acids Res. 9:2251, 1981). This tail can then be hybridized by a poly dG oligo which can act as a primer for the synthesis of full length second strand cDNA. Okayama and Berg, report a method for obtaining full length cDNA constructs. This method has been simplified by using synthetic primer-adapters that have both homopolymeric tails for priming the synthesis of the first and second strands and restriction sites for cloning into plasmids (Coleclough, et al., Gene 34:305, 1985) and bacteriophage vectors (Krawinkel, et al., Nucleic Acids Res. 14:1913, 1986; and Han, et al., Nucleic Acids Res. 15:6304, 1987).

These strategies can be coupled with additional strategies for isolating rare mRNA populations. For example, a typical mammalian cell contains between 10,000 and 30,000 different mRNA sequences. Davidson, Gene Activity in Early Development, 2nd ed., Academic Press, New York, 1976. The number of clones required to achieve a given probability that a low-abundance mRNA will be present in a cDNA library is $N=(\ln(1-P))/(\ln(1-1/n))$ where N is the number of clones required, P is the probability desired, and $1/n$ is the fractional proportion of the total mRNA that is represented by a single rare mRNA (Sambrook, et al.,1989).

One method to enrich preparations of mRNA for sequences of interest is to fractionate by size. One such method is to fractionate by electrophoresis through an agarose gel (Pennica, et al., Nature 301:214, 1983). Another such method employs sucrose gradient centrifugation in the presence of an agent, such as methylmercuric hydroxide, that denatures secondary structure in RNA (Schweinfest, et al., Proc. Natl. Acad. Sci. (U.S.A.) 79:4997–5000, 1982).

A frequently adopted method is to construct equalized or normalized cDNA libraries (Ko, Nucleic Acids Res. 18:5705, 1990; Patanjali, S. R. et al., Proc. Natl. Acad. Sci. (U.S.A.) 88:1943, 1991). Typically, the cDNA population is normalized by subtractive hybridization. Schmid, et al., J. Neurochem. 48:307, 1987; Fargnoli, et al., Anal. Biochem. 187:364, 1990; Travis, et al., Proc. Natl. Acad. Sci (U.S.A.) 85:1696, 1988; Kato, Eur. J. Neurosci. 2:704, 1990; and Schweinfest, et al., Genet. Anal. Tech. Appl. 7:64, 1990). Subtraction represents another method for reducing the population of certain sequences in the cDNA library (Swaroop, et al., Nucleic Acids Res. 19:1954, 1991). Normalized libraries can be constructed using the Soares procedure (Soares et al., Proc. Natl. Acad. Sci. (U.S.A.) 91:9228, 1994). This approach is designed to reduce the initial 10,000-fold variation in individual cDNA frequencies to achieve abundances within one order of magnitude while maintaining the overall sequence complexity of the library. In the normalization process, the prevalence of high-abundance cDNA clones decreases dramatically, clones with mid-level abundance are relatively unaffected, and clones for rare transcripts are effectively increased in abundance.

ESTs can be sequenced by a number of methods. Two basic methods can be used for DNA sequencing, the chain termination method of Sanger et al., Proc. Natl. Acad. Sci. (U.S.A.) 74: 5463, 1977 and the chemical degradation method of Maxam and Gilbert, Proc. Nat. Acad. Sci. (U.S.A.) 74: 560, 1977. Automation and advances in technology such as the replacement of radioisotopes with fluorescence-based sequencing have reduced the effort required to sequence DNA (Craxton, Methods, 2: 20, 1991; Ju et al., Proc. Natl. Acad. Sci. (U.S.A.) 92: 4347, 1995; Tabor and Richardson, Proc. Natl. Acad. Sci. (U.S.A.) 92: 6339, 1995). Automated sequencers are available from a number of manufacturers, for example, Pharmacia Biotech, Inc., Piscataway, N.J. (Pharmacia ALF), LI-COR, Inc., Lincoln, Nebr. (LI-COR 4,000) and Millipore, Bedford, Mass. (Millipore BaseStation).

ESTs longer than 150 bp have been found to be useful for similarity searches and mapping. (Adams, et al., Science 252:1651, 1991. EST sequences normally range from 150–450 bases. This is the length of sequence information that is routinely and reliably generated using single run sequence data. Typically, only single run sequence data is obtained from the cDNA library, Adams, et al., Science 252:1651, 1991. Automated single run sequencing typically results in an approximately 2–3% error or base ambiguity rate. (Boguski, et al., Nature Genetics, 4:332, 1993).

EST databases have been constructed or partially constructed from, for example, *C. elegans* (McCombrie, et al., Nature Genetics 1:124, 1992, human liver cell line HepG2 (Okubo, et al., Nature Genetics 2:173, 1992); human brain RNA (Adams, et al., Science 252:1651, 1991; Adams, et al., Nature 355:632, 1992); Arabidopsis, (Newman, et al., Plant Physiol. 106:1241, 1994); and rice (Kurata, et al., Nature Genetics 8:365, 1994). The present invention uses ESTs from a number of libraries prepared from multiple corn tissues as a tool for the identification of genes expressed in desired tissues which then facilitates the isolation of 5' regulatory sequences such as promoters which regulate the genes.

Computer-based sequence analyses can be used to identify differentially expressed sequences including but not limited to those sequences expressed in one tissue compared with another tissue. For example, a different set of sequences can be found from cDNA isolated from plant tissue isolated from root tissue versus leaf tissue. Accordingly, sequences can be compared from cDNA libraries prepared from plants grown under different environmental or physiological conditions. Once the preferred sequences are identified from the cDNA library of interest, the genomic clones can be isolated from a genomic library prepared from the plant tissue, and corresponding regulatory sequences including but not limited to 5' regulatory sequences can be identified and isolated.

In one preferred embodiment, expressed sequence tags (EST) sequences from a variety of cDNA libraries are catalogued in a sequence database. This database is used to identify promoter targets from a particular tissue of interest. The selection of expressed sequence tags for subsequent promoter isolation is reflective of the presence of one or more sequences among the representative ESTs from a random sampling of an individual cDNA library, or a collection of cDNA libraries. For example, the identification of regulatory sequences that regulate the expression of transcripts in leaf and root tissue is conducted by identifying ESTs found in leaf and root cDNA libraries and absent or in lower abundance in other cDNA libraries and the expression profile for a given EST is assessed. By abundance as used herein is meant the number of times a clone or cluster of clones appears in a library. The sequences that are enhanced or in high abundance in a specific tissue or organ which represent a target expression profile are identified in this manner and primers can be designed from the identified EST sequences. A PCR-based approach can be used to amplify flanking regions from a genomic library of the target plant of interest. A number of methods are known to those of skill in the art to amplify unknown DNA sequences adjacent to a core region of known sequence. Methods include but are not limited to inverse PCR (IPCR), vectorette PCR, Y-shaped PCR and genome walking approaches.

In a preferred embodiment, genomic DNA ligated to an adapter is subjected to a primary round of PCR amplification with a gene-specific primer and a primer which anneals to the adapter sequence. The PCR product is next used as the template for a nested round of PCR amplification with a second gene-specific primer and second adapter. The resulting fragments from the nested PCR reaction are then isolated, purified and subcloned into an appropriate vector. The fragments are sequenced and the translational start sites can be identified when the EST is derived from a truncated cDNA. The fragments can be cloned into plant expression vectors as transcriptional or translational fusions with a reporter gene such as β-glucuronidase (GUS). The constructs can be tested in transient analyses and subsequently the 5' regulatory regions are operably linked to other genes and regulatory sequences of interest in a suitable plant transformation vector and the transformed plants are ana-lyzed for the expression of the gene(s) of interest by any number of methods known to those of skill in the art.

Any plant can be selected for the identification of genes and regulatory sequences. Examples of suitable plant targets for the isolation of genes and regulatory sequences would include but are not limited to Acadia, alfalfa, apple, apricot, Arabidopsis, artichoke, arugula, asparagus, avocado, banana, barley, beans, beet, blackberry, blueberry, broccoli, brussels sprouts, cabbage, canola, cantaloupe, carrot, cassava, castorbean, cauliflower, celery, cherry, chicory, cilantro, citrus, clementines, clover, coconut, coffee, corn, cotton, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, linseed, mango, melon, mushroom, nectarine, nut, oat, oil palm, oil seed rape, okra, olive, onion, orange, an ornamental plant, palm, papaya, parsley, parsnip, pea, peach, peanut, pear, pepper, persimmon, pine, pineapple, plantain, plum, pomegranate, poplar, potato, pumpkin, quince, radiata pine, radiscchio, radish, rapeseed, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf, turnip, a vine, watermelon, wheat, yams, and zucchini. Particularly preferred plant targets would include corn, cotton, soybean, and wheat.

The nucleic acid molecules of the present invention are isolated from corn (*Zea mays*). The corn plant develops about 20–21 leaves, silks about 65 days post-emergence, and matures about 125 days post-emergence. Normal corn plants follow a general pattern of development, but the time interval between different stages and morphology varies between different hybrids, growth and environmental conditions.

There are a number of identifiable stages in corn plant development. The stages are defined as vegetative (V) and reproductive (R) stages. Subdivisions of the V stages are numerically designated as V1, V2,V3, etc., through V(n) where (n) represents the last leaf stage before tasseling (VT) and the first V stage is the emergence (VE) stage. For example, VE is the emergence from the soil of a seedling leaf, V1 represents the first true leaf, V2 represents the second leaf, etc. The reproductive stages include the first appearance of silk to the mature seed and are represented as follows: R1 is silking, R2 is blistering, R3 is the milk stage, R4 is the dough stage, R5 is the dent stage, and R6 is physiological maturity (see for example, Ritchie S W et al. (1986) How a Corn Plant Develops, Iowa State University of Science and Technology Cooperative Exension Service, Ames, Iowa 48: 1–21).

Any type of plant tissue can be used as a target tissue for the identification of genes and associated regulatory elements, including but not limited to promoter sequences. For the present invention multiple tissues of corn are used. More preferably, corn meristem, immature tassel, leaf, root, culm, etiolated seedlings, sheath, primary shoot, ear, silk and endosperm are the target tissues for identification of promoter sequences.

Any method which allows a differential comparison between different types or classes of sequences can be used to isolate genes or regulatory sequences of interest. For example in one differential screening approach, a cDNA library from mRNA isolated from a particular tissue can be prepared in a bacteriophage host using a commercially available cloning kit. The plaques are spread onto plates containing lawns of a bacterial host such as *E. coli* to generate bacteriophage plaques. About 105–106 plaques can be lifted onto DNA binding membranes. Duplicate membranes are probed using probes generated from mRNA from the target and non-target or background tissue. The probes are labeled to facilitate detection after hybridization and development. Plaques that hybridize to target tissue-derived probes but not to non-target tissue derived probes that display a desired differential pattern of expression can be selected for further analysis. Genomic DNA libraries can also be prepared from a chosen species by partial digestion with a restriction enzyme and size selecting the DNA fragments within a particular size range. The genomic DNA can be cloned into a suitable vector including but not limited to a bacteriophage, and prepared using a suitable kit as described earlier (see for example, Stratagene, La Jolla, Calif. or Gibco BRL, Gaithersburg, Md.).

Differential hybridization techniques as described are well known to those of skill in the art and can be used to isolate a desired class of sequences. By classes of sequences as used herein is meant sequences that can be grouped based on a common identifier including but not limited to sequences isolated from a common target plant, a common library, or a common plant tissue type. In a preferred embodiment, sequences of interest are identified based on sequence analyses and querying of a collection of diverse cDNA sequences from libraries of different tissue types. The disclosed method provides an example of a differential screening approach based on electronic sequence analyses of plant ESTs derived from diverse cDNA libraries.

A number of methods used to assess gene expression are based on measuring the mRNA level in an organ, tissue, or cell sample. Typical methods include but are not limited to RNA blots, ribonuclease protection assays and RT-PCR. In another preferred embodiment, a high-throughput method is used whereby regulatory sequences are identified from a transcript profiling approach. The development of cDNA microarray technology enables the systematic monitoring of gene expression profiles for thousands of genes (Schena et al, Science, 270: 467, 1995). This DNA chip-based technology arrays thousands of cDNA sequences on a support surface. These arrays are simultaneously hybridized to a-multiple of labeled cDNA probes prepared from RNA samples of different cell or tissue types, allowing direct comparative analysis of expression. This technology was first demonstrated by analyzing 48 Arabidopsis genes for differential expression in roots and shoots (Schena et al, Science, 270:467, 1995). More recently, the expression profiles of over 1400 genes were monitored using cDNA microarrays (Ruan et al, The Plant Journal 15:821, 1998). Microarrays provide a high-throughput, quantitative and reproducible method to analyze gene expression and characterize gene function. The transcript profiling approach using microarrays thus provides another valuable tool for the isolation of regulatory sequences such as promoters associated with those genes.

The present invention uses high throughput sequence analyses to form the foundation of rapid computer-based identification of sequences of interest. Those of skill in the art are aware of the resources available for sequence analyses. Sequence comparisons can be undertaken by determining the similarity of the test or query sequence with sequences in publicly available or proprietary databases ("similarity analysis") or by searching for certain motifs ("intrinsic sequence analysis") (e.g. cis elements) (Coulson, Trends in Biotechnology, 12:76, 1994; Birren, et al., Genome Analysis, 1:543, 1997).

The nucleotide sequences provided in SEQ ID NOS: 53–75 or fragments thereof, or complements thereof, or a nucleotide sequence at least 90% identical, preferably 95% identical even more preferably 99% or 100% identical to the sequence provided in SEQ ID NOS: 53–75 or fragment thereof, or complement thereof, can be "provided" in a variety of mediums to facilitate use. Such a medium can also provide a subset thereof in a form that allows one of skill in the art to examine the sequences.

In one application of this embodiment, a nucleotide sequence of the present invention can be recorded on computer readable media. As used herein, "computer readable media" refers to any medium that can be read and accessed directly by a computer. Such media include, but are not limited to: magnetic storage media, such as floppy discs, hard disc, storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising computer readable medium having recorded thereon a nucleotide sequence of the present invention.

By providing one or more of nucleotide sequences of the present invention, those of skill in the art can routinely access the sequence information for a variety of purposes. Computer software is publicly available that allows one of ordinary skill in the art to access sequence information provided in a computer readable medium. Examples of public databases would include but are not limited to the DNA Database of Japan (DDBJ); Genbank; and the European Molecular Biology Laboratory Nucleic Acid Sequence Database or versions thereof. A number of different search algorithms have been developed, including but not limited to the suite of programs referred to as BLAST programs. There are five implementations of BLAST, three designed for nucleotide sequence queries (BLASTN, BLASTX, AND TBLASTX) and two designed for protein sequence queries (BLASTP and TBLASTN) (Coulson, Trends in Biotechnology, 12:76–80, 1994; Birren, et al., Genome Analysis, 1:543, 1997).

Any program designed for motif searching also has utility in the present invention. Sequence analysis programs designed for motif searching can be used for identification of cis elements. Preferred computer programs would include but are not limited to MEME, SIGNAL SCAN, and GENESCAN. Meme is a program that identifies conserved motifs (either nucleic acid or peptide) in a group of unaligned sequences. Meme saves these motifs as a set of profiles. These profiles can be used to search a database of sequences. A MEME algorithm (version 2.2) can be found in version 10.0 of the GCC package; MEME (T. Bailey and C. Elkan, Machine Learning, 21 (1–2):51–80, 1995 ). SignalScan is a program that identifies known motifs in the test sequences using information from other motif databases (Prestridge, D. S., CABIOS 7, 203–206 (1991). GeneScan is another suitable program for motif searching (Burge, C and Karlin, S. J. Mol. Biol. 268, 78–94(1997).

As used herein, "a target structural motif", or "target motif" refers to any rationally selected sequence or combination of sequences in which the sequence(s) are chosen based on a three-dimensional configuration which is formed upon the folding of the target motif. There are a variety of target motifs known to those of skill in the art. Protein target motifs include but are not limited to, enzymatic active sites and signal sequences. Preferred target motifs of the present invention would include but are not limited to promoter sequences, cis elements, hairpin structures and other expression elements such as protein building sequences.

As used herein, "search means" refers to one or more programs which are implemented on the computer-based system to compare a target sequence or target structural motif with the sequence information stored within the data storage means. Search means are used to identify fragments or regions of the sequences of the present invention that match a particular target sequence or target motif. Also, multiple sequences can be compared in order to identify common regions or motifs which may be responsible for specific functions. For example, cis elements or sequence domains which confer a specific expression profile can be identified when multiple promoter regions of similar classes of promoters are aligned and analyzed by certain software packages.

The present invention further provides systems, particularly computer-based systems, which contain the sequence information described herein. As used herein, a "computer-based system" refers to the hardware means, software means, and data storage means used to analyze the nucleotide sequence information of the present invention. The minimum hardware means of the computer-based systems of the present invention comprises a central processing unit (CPU), input means, output means, and data storage means. Those of skill in the art can appreciate that any one of the available computer-based systems are suitable for use in the present invention.

SEQ ID NOS: 6–52 are primers designed from the cDNA sequences identified from the computer-based sequence comparisons. These sequences are used to extend the nucleic acid sequence using polymerase chain reaction (PCR) amplification techniques (see for example, Mullis et al., Cold Spring Harbor Symp. Quant. Biol. 51:263, 1986; Erlich, et al., European Patent Appln. 50,424; European Patent Appln. 84,796, European Patent Appln. 258,017, European Patent Appln. 237,362; Mullis, European Patent Appln. 201,184; Mullis, et al., U.S. Patent No. 4,683,202; Erlich, U.S. Pat. No. 4,582,788; and Saiki, et al., U.S. Pat. No. 4,683,194). A number of PCR amplification methods are known to those of skill in the art, and are used to identify nucleic acid sequences adjacent to a known sequence. For example, inverse pcr (IPCR) methods to amplify unknown DNA sequences adjacent to a core region of known sequence have been described. Other methods are also available such as capture PCR (Lagerstrom M., et al., PCR Methods Applic. 1: 111, 1991, and walking PCR (Parker, J D et al.,Nucleic Acids Res 19:3055, 1991). A number of manufacturers have also developed kits based on modifications of these methods for the purposes of identifying sequences of interest. Technical advances including improvements in primer and adapter design, improvements in the polymerase enzyme, and thermocycler capabilities have facilitated quicker, efficient methods for isolating sequences of interest.

In a preferred embodiment, the flanking sequences containing the 5' regulatory elements of the present invention are isolated using a genome-walking approach (Universal GenomeWalker™ Kit, CLONTECH Laboratories, Inc., Palo, Alto, Calif.). In brief, the purified genomic DNA is subjected to a restriction enzyme digest which produces genomic DNA fragments with ends that are ligated with GenomeWalker™ adapters. GenomeWalker™ primers are used along with gene specific primers in two consecutive PCR reactions (primary and nested PCR reactions) to produce PCR products containing the 5' regulatory sequences which are subsequently cloned and sequenced.

In addition to their use in modulating gene expression, the promoter sequences of the present invention also have utility as probes or primers in nucleic acid hybridization experiments. The nucleic-acid probes and primers of the present invention can hybridize under stringent conditions to a target DNA sequence. The term "stringent hybridization conditions" is defined as conditions under which a probe or primer hybridizes specifically with a target sequence(s) and not with non-target sequences, as can be determined empirically. The term "stringent conditions" is functionally defined with regard to the hybridization of a nucleic-acid probe to a target nucleic acid (i.e., to a particular nucleic-acid sequence of interest) by the specific hybridization procedure discussed in Sambrook et al., 1989, at 9.52–9.55. See also, Sambrook et al., 1989 at 9.47–9.52, 9.56–9.58; Kanehisa, Nucl. Acids Res. 12:203–213, 1984; and Wetmur and Davidson, J. Mol. Biol. 31:349–370, 1968. Appropriate stringency conditions which promote DNA hybridization are, for example, 6.0× sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y., 1989, 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

For example, hybridization using DNA or RNA probes or primers can be performed at 65° C. in 6×SSC, 0.5% SDS, 5×Denhardt's, 100 µg/mL nonspecific DNA (e.g., sonicated salmon sperm DNA) with washing at 0.5×SSC, 0.5% SDS at 65° C., for high stringency.

It is contemplated that lower stringency hybridization conditions such as lower hybridization and/or washing temperatures can be used to identify related sequences having a lower degree of sequence similarity if specificity of binding of the probe or primer to target sequence(s) is preserved. Accordingly, the nucleotide sequences of the present invention can be used for their ability to selectively form duplex molecules with complementary stretches of DNA fragments. Detection of DNA segments via hybridization is well-known to those of skill in the art, and thus depending on the application envisioned, one will desire to employ varying hybridization conditions to achieve varying degrees of selectivity of probe towards target sequence and the method of choice will depend on the desired results.

The nucleic acid sequences in SEQ ID NOS: 53–75 and any variants thereof, are capable of hybridizing to other nucleic acid sequences under appropriately selected conditions of stringency. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low stringency" conditions. Similarly, the molecules are said to be "complementary" is they can hybridize to one another with sufficient stability to permit them to remain annealed to one another under conventional "high stringency" conditions. Conventional stringency conditions are described by Sambrook, et al., Molecular Cloning, A Laboratory Manual, 2nd Ed., Cold Spring Harbor Press, Cold Spring Harbor, N.Y., 1989, and by Haymes et al., Nucleic Acid Hybridization, A Practical Approach, IRL Press, Washington, D.C., 1985.

In a preferred embodiment, the nucleic acid sequences, SEQ ID NOS: 53–75, or a fragment, region, cis element, or oligomer of any of these sequences, may be used in hybridization assays of other plant tissues to identify closely related or homologous genes and associated regulatory sequences. These include but are not limited to Southern or northern hybridization assays on any substrate including but not limited to an appropriately prepared plant tissue, cellulose, nylon, or combination filter, chip, or glass slide. Such methodologies are well known in the art and are available in a kit or preparation which can be supplied by commercial vendors.

Of course, fragments can also be obtained by other techniques such as by directly synthesizing the fragment by chemical means, as is commonly practiced by using an automated oligonucleotide synthesizer. Also, fragments can be obtained by application of nucleic acid reproduction technology, such as the PCR™ (polymerase chain reaction) technology by recombinant DNA techniques generally known to those of skill in the art of molecular biology. Regarding the amplification of a target nucleic-acid sequence (e.g., by PCR) using a particular amplification primer pair, "stringent PCR conditions" refer to conditions that permit the primer pair to hybridize only to the target nucleic-acid sequence to which a primer having the corresponding wild-type sequence (or its complement) would bind and preferably to produce a unique amplification product.

A fragment of a nucleic acid as used herein refers to any portion of the nucleic acid that is less than full-length. For example, for the present invention any length of nucleotide sequence that is less than the disclosed nucleotide sequences of SEQ ID NOS: 53–75 is considered to be a fragment. A fragment can also comprise at least a minimum length capable of hybridizing specifically with a native nucleic acid under stringent hybridization conditions as defined above. The length of such a minimal fragment is preferably at least eight nucleotides, more preferably 15 nucleotides, even more preferably at least 20 nucleotides, and most preferably at least 30 nucleotides of a native nucleic acid sequence.

The nucleic acid sequences of the present invention can also be used as probes and primers. Nucleic acid probes and primers can be prepared based on a native gene sequence. A "probe" is an isolated nucleic acid to which is attached a conventional detectable label or reporter molecule, e.g., a radioactive isotope, ligand, chemiluminescent agent, or enzyme. "Primers" are isolated nucleic acids that are annealed to a complementary target DNA strand by nucleic acid hybridization to form a hybrid between the primer and the target DNA strand, then extended along the target DNA strand by a polymerase, e.g., a DNA polymerase. Primer pairs can be used for amplification of a nucleic acid sequence, e.g., by the polymerase chain reaction (PCR) or other conventional nucleic-acid amplification methods.

Probes and primers are generally 15 nucleotides or more in length, preferably 20 nucleotides or more, more preferably 25 nucleotides, and most preferably 30 nucleotides or more. Such probes and primers hybridize specifically to a target DNA or RNA sequence under high stringency hybridization conditions and hybridize specifically to a target native sequence of another species under lower stringency conditions. Preferably, probes and primers according to the present invention have complete sequence similarity with the native sequence, although probes differing from the native sequence and that retain the ability to hybridize to target native sequences may be designed by conventional methods. Methods for preparing and using probes and primers are described, for example, in Molecular Cloning: A Laboratory Manual, 2nd ed., vol. 1–3, ed. Sambrook et al., Cold Spring Harbor Laboratory Press, Cold Spring Harbor, N.Y., 1989 (hereinafter, "Sambrook et al., 1989"); Current Protocols in Molecular Biology, ed. Ausubel et al., Greene Publishing and Wiley-Interscience, New York, 1992 (with periodic updates) (hereinafter, "Ausubel et al., 1992); and Innis et al., PCR Protocols: A Guide to Methods and Applications, Academic Press: San Diego, 1990. PCR-primer pairs can be derived from a known sequence, for example, by using computer programs intended for that purpose such as Primer (Version 0.5, © 1991, Whitehead Institute for Biomedical Research, Cambridge, Mass.). Primers and probes based on the native promoter sequences disclosed herein can be used to confirm and, if necessary, to modify the disclosed sequences by conventional methods, e.g., by re-cloning and re-sequencing.

In another embodiment, the nucleotide sequences of the promoters disclosed herein can be modified. Those skilled in the art can create DNA molecules that have variations in the nucleotide sequence. The nucleotide sequences of the present invention as shown in SEQ ID NOS: 53–75 may be modified or altered to enhance their control characteristics. One preferred method of alteration of a nucleic acid sequence is to use PCR to modify selected nucleotides or regions of sequences. These methods are known to those of skill in the art. Sequences can be modified, for example by insertion, deletion or replacement of template sequences in a PCR-based DNA modification approach. "Variant" DNA molecules are DNA molecules containing changes in which one or more nucleotides of a native sequence is deleted, added, and/or substituted, preferably while substantially maintaining promoter function. In the case of a promoter fragment, "variant" DNA can include changes affecting the transcription of a minimal promoter to which it is operably linked. Variant DNA molecules can be produced, for example, by standard DNA mutagenesis techniques or by chemically synthesizing the variant DNA molecule or a portion thereof.

In another embodiment, the nucleotide sequences as shown in SEQ ID NOS: 53–75 includes any length of said nucleotide sequences which is capable of regulating an operably linked DNA sequence. For example, the sequences as disclosed in SEQ ID NOS: 53–75 may be truncated or portions deleted and still be capable of regulating transcription of an operably linked DNA sequence. In a related embodiment, a cis element of the disclosed sequences may confer a particular specificity such as conferring enhanced expression of operably linked DNA sequences in certain tissues and therefore is also capable of regulating transcription of operably linked DNA sequences. Consequently, any sequence fragments, portions, or regions of the disclosed sequences of SEQ ID NOS: 53–75 can be used as regulatory sequences, including but not limited to cis elements or motifs of the disclosed sequences. For example, one or more base pairs may be deleted from the 5' or 3' end of a promoter sequence to produce a "truncated" promoter. One or more base pairs can also be inserted, deleted, or substituted internally to a promoter sequence. Promoters can be constructed such that promoter fragments or elements are operably linked, for example, by placing such a fragment upstream of a minimal promoter. A minimal or basal promoter is a piece of DNA which is capable of recruiting and binding the basal transcription machinery. One example of basal transcription machinery in eukaryotic cells is the RNA polymerase II complex and its accessory proteins. The enzymatic components of the basal transcription machinery are capable of initiating and elongating transcription of a given gene, utilizing a minimal or basal promoter. That is, there are not added cis-acting sequences in the promoter region which are capable of recruiting and binding transcription factors that modulate transcription, e.g., enhance, repress, render transcription hormone-dependent, etc. Substitutions, deletions, insertions or any combination thereof can be combined to produce a final construct.

Native or synthetic nucleic acids according to the present invention can be incorporated into recombinant nucleic acid constructs, typically DNA constructs, capable of introduction into and replication in a host cell. In one preferred embodiment, the nucleotide sequences of the present invention as shown in SEQ ID NOS: 53–75 or fragments, variants, or derivatives thereof are incorporated into an expression vector cassette which includes the promoter regions of the present invention operably linked to a genetic component such as a selectable, screenable, or scorable marker gene. The disclosed nucleic acid sequences of the present invention are preferably operably linked to a genetic component such as a nucleic acid which confers a desirable characteristic associated with plant morphology, physiology, growth and development, yield, nutritional enhancement, disease or pest resistance, or environmental or chemical tolerance. These genetic components such as marker genes or agronomic genes of interest can function in the identification of a transformed plant cell or plant, or a produce a product of agronomic utility.

In a preferred embodiment, one genetic component produces a product which serves as a selection device and functions in a regenerable plant tissue to produce a compound which would confer upon the plant tissue resistance to an otherwise toxic compound. Genes of interest for use as a selectable, screenable, or scorable marker would include but are not limited to the coding sequence for β-glucuronidase (GUS), the coding sequence for green fluorescent protein (GFP), the coding sequence for luciferase (LUX), antibiotic or herbicide tolerance genes. examples of transposons and associated antibiotic resistance genes include the transposons Tns (b1a), Tn5 (nptII), Tn7 (dhfr), penicillins, kanamycin (and neomycin, G418, bleomycin); methotrexate (and trimethoprim); chloramphenicol; kanamycin and tetracycline.

Characteristics useful for selectable markers in plants have been outlined in a report on the use of microorganisms (Advisory Committee on Novel Foods and Processes, July 1994). These include stringent selection with minimum number of nontransformed tissues, large numbers of independent transformation events with no significant interference with the regeneration, application to a large number of species, and availability of an assay to score the tissues for presence of the marker.

A number of selectable marker genes are known in the art and several antibiotic resistance markers satisfy these criteria, including those resistant to kanamycin (nptII), hygromycin B (aph IV) and gentamycin (aac3 and aacC4). Useful dominant selectable marker genes include genes encoding antibiotic resistance genes (e.g., resistance to hygromycin, kanamycin, bleomycin, G418, streptomycin or spectinomycin); and herbicide resistance genes (e.g., phosphinothricin acetyltransferase). A useful strategy for selection of transformants for herbicide resistance is described, e.g., in Vasil, Cell Culture and Somatic Cell Genetics of Plants, Vols. I–III, Laboratory Procedures and Their Applications Academic Press, New York, 1984. Particularly preferred selectable marker genes for use in the present invention would genes which confer resistance to compounds such as antibiotics like kanamycin , and herbicides like glyphosate (Della-Cioppa et al., Bio/Technology 5(6), 1987, U.S. Pat. No. 5,463,175, U.S. Pat. No. 5,633,435). Other selection devices can also be implemented and would still fall within the scope of the present invention.

For the practice of the present invention, conventional compositions and methods for preparing and using vectors and host cells are employed, as discussed, inter alia, in Sambrook et al., 1989). In a preferred embodiment, the host cell is a plant cell. A number of vectors suitable for stable transfection of plant cells or for the establishment of transgenic plants have been described in, e.g., Pouwels et al., Cloning Vectors: A Laboratory Manual, 1985, supp. 1987); Weissbach and Weissbach, Methods for Plant Molecular Biology, Academic Press, 1989; Gelvin et al., Plant Molecular Biology Manual, Kluwer Academic Publishers, 1990; and R. R. D. Croy, Plant Molecular Biology LabFax, BIOS Scientific Publishers, 1993. Plant expression vectors can include, for example, one or more cloned plant genes under the transcriptional control of 5' and 3' regulatory sequences. They can also can include a selectable marker as described to allow selection of host cells containing the expression vector. Such plant expression vectors also typically contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and a polyadenylation signal. Other sequences, of bacterial origin are also included to allow the vector to be cloned in a bacterial host. The vector will also typically contain a broad host range prokaryotic origin of replication. In a particularly preferred embodiment, the host cell is a plant cell and the plant expression vector comprises a promoter region as disclosed in SEQ ID NOS: 53–75, an operably linked transcribable sequence, and a transcription termination sequence. Other regulatory sequences can also be included such as 5' non-translated leaders, in addition to restriction enzyme sites for cloning purposes.

A number of promoters have utility for plant gene expression for any gene of interest including but not limited to selectable markers, scorable markers, genes for pest tolerance, disease tolerance, nutritional enhancements and any other gene of agronomic interest. Examples of constitutive promoters useful for plant gene expression include but are not limited to, the cauliflower mosaic virus (CaMV) 35S promoter, which confers constitutive, high-level expression in most plant tissues (see, e.g., Odel et al., Nature 313:810, 1985), including monocots (see, e.g., Dekeyser et al., Plant Cell 2:591, 1990; Terada and Shimamoto, Mol. Gen. Genet. 220:389, 1990); the nopaline synthase promoter (An et al., Plant Physiol. 88:547, 1988) and the octopine synthase promoter (Fromm et al., Plant Cell 1:977, 1989) and the figwort mosaic virus (FMV) promoter.

A variety of plant gene promoters that are regulated in response to environmental, hormonal, chemical, and/or developmental signals can be used for expression of an operably linked gene in plant cells, including promoters regulated by (1) heat (Callis et al., Plant Physiol. 88:965, 1988), (2) light (e.g., pea rbcS-3A promoter, Kuhlemeier et al., Plant Cell 1:471, 1989; maize RbcS promoter, Schaffner and Sheen, Plant Cell 3:997, 1991; or chlorophyll a/b-binding protein promoter, Simpson et al., EMBO J. 4:2723, 1985), (3) hormones, such as abscisic acid (Marcotte et al., Plant Cell 1:969, 1989), (4) wounding (e.g., wunl, Siebertz et al., Plant Cell 1:961, 1989); or (5) chemicals such as methyl jasmonate, salicylic acid, or Safener. It may also be advantageous to employ (6) organ-specific promoters (e.g., Roshal et al., EMBO J. 6:1155, 1987; Schernthaneret al., EMBO J. 7:1249, 1988; Bustos et al., Plant Cell 1:839, 1989).

The promoters of the present invention are plant promoters that are capable of transcribing operatively linked DNA sequences in multiple tissues and can be operably linked to any gene of interest in an expression vector.

Plant expression vectors can include RNA processing signals, e.g., introns, which may be positioned upstream or downstream of a polypeptide-encoding sequence in the transgene. In addition, the expression vectors may include additional regulatory sequences from the 3'-untranslated region of plant genes (Thornburg et al., Proc. Natl. Acad. Sci. USA 84:744 (1987); An et al., Plant Cell 1:115 (1989), e.g., a 3' terminator region to increase mRNA stability of the mRNA, such as the PI-II terminator region of potato or the octopine or nopaline synthase 3' terminator regions. 5' non-translated regions of a mRNA can play an important role in translation initiation and can also be a genetic component in a plant expression vector. For example, non-translated 5' leader sequences derived from heat shock protein genes have been demonstrated to enhance gene expression in plants (see, for example U.S. Pat. No. 5,362,865 herein incorporated by reference in its entirety). These additional upstream and downstream regulatory sequences may be derived from a source that is native or heterologous with respect to the other elements present on the expression vector.

The promoter sequences of the present invention are used to control gene expression in plant cells. The disclosed promoter sequences are genetic components which are part of vectors used in plant transformation. The promoter sequences of the present invention can be used with any suitable plant transformation plasmid or vector containing a selectable or screenable marker and associated regulatory elements, as described, along with one or more nucleic acids expressed in a manner sufficient to confer a particular desirable trait. Examples of suitable structural genes of agronomic interest envisioned by the present invention would include but are not limited to one or more genes for insect tolerance, such as *Bacillus thuringiensis*., pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). Particularly preferred genes would include any herbicide tolerance gene which confers tolerance to the herbicide glyphosate. These genes would include but are not limited to AGRTU.aroA:CP4 and GOX genes as described in U.S. Pat. Nos. 5,463,175 herein incorporated by reference in its entirety and 5,633,435 herein incorporated by reference in its entirety.

Alternatively, the DNA coding sequences can effect these phenotypes by encoding a non-translatable RNA molecule that causes the targeted inhibition of expression of an endogenous gene, for example via antisense- or cosuppression-mediated mechanisms (see, for example, Bird et al., Biotech. Gen. Engin. Rev. 9:207,1991). The RNA could also be a catalytic RNA molecule (i.e., a ribozyme) engineered to cleave a desired endogenous mRNA product (see for example, Gibson and Shillitoe, Mol. Biotech. 7:125, 1997). Thus, any gene which produces a protein or mRNA which expresses a phenotype or morphology change of interest are useful for the practice of the present invention.

In addition to regulatory elements or sequences located upstream (5') or within a DNA sequence, there are downstream (3') sequences which affect gene expression and thus the term regulatory sequence as used herein refers to any nucleotide sequence located upstream, within, or downstream to a DNA sequence which controls, mediates, or affects expression of a gene product in conjunction with the protein synthetic apparatus of the cell.

The promoter sequences of the present invention may be modified, for example for expression in other plant systems. In another approach, novel hybrid promoters can be designed or engineered by a number of methods. Many promoters contain upstream sequences which activate, enhance or define the strength and/or specificity of the promoter (Atchison, Ann. Rev. Cell Biol. 4:127, 1988). T-DNA genes, for example contain "TATA" boxes defining the site of transcription initiation and other upstream elements located upstream of the transcription initiation site modulate transcription levels (Gelvin, In Transgenic Plants (Kung, S.-D. And Us, R., eds), San Diego: Academic Press, pp.49–87, 1988). Another chimeric promoter combined a trimer of the octopine synthase (ocs) activator to the mannopine synthase (mas) activator plus promoter and reported an increase in expression of a reporter gene (Min Ni et al., The Plant Journal 7:661, 1995). The upstream regulatory sequences of the present invention can be used for the construction of such chimeric or hybrid promoters. Methods for construction of variant promoters of the present invention include but are not limited to combining control elements of different promoters or duplicating portions or regions of a promoter (see for example U.S. Pat. No. 5,110732 herein incorporated by reference in its entirety and U.S. Pat. No. 5,097,025 herein incorporated by reference in its entirety). Those of skill in the art are familiar with the standard resource materials which describe specific conditions and procedures for the construction, manipulation and isolation of macromolecules (e.g., DNA molecules, plasmids, etc.), generation of recombinant organisms and the screening and isolation of genes, (see for example Sambrook et al., Molecular Cloning: A Laboratory Manual, Cold Spring Harbor Press, 1989; Mailga et al., Methods in Plant Molecular Biology, Cold Spring Harbor Press, 1995; Birren et al., Genome Analysis: volume 1, Analyzing DNA, (1997); volume 2, Detecting Genes, (1998); volume 3, Cloning Systems, (1999), volume 4, Mapping Genomes, (1999), Cold Spring Harbor, N.Y.).

The promoter sequences of the present invention can be incorporated into an expression vector using screenable or scorable markers as described and tested in transient analyses which provide an indication of gene expression in stable plant systems. Methods of testing gene expression in transient assays are known to those of skill in the art. Transient expression of marker genes has been reported using a variety of plants, tissues and DNA delivery systems. For example, types of transient analyses can include but are not limited to direct gene delivery via electroporation or particle bombardment of tissues in any transient plant assay using any plant species of interest. Such transient systems would include but are not limited to protoplasts from suspension cultures in wheat (Zhou et al., Plant Cell Reports 12:612. 1993), electroporation of leaf protoplasts of wheat (Sethi et al., J.

Crop Sci. 52: 152, 1983); electroporation of protoplast prepared from corn tissue (Sheen, J. The Plant Cell 3: 225, 1991), or particle bombardment of specific tissues of interest. The present invention encompasses the use of any transient expression system to evaluate regulatory sequences operatively linked to selected reporter genes, marker genes or agronomic genes of interest. Examples of plant tissues envisioned to test in transients via an appropriate delivery system would include but are not limited to leaf base tissues, callus, cotyledons, roots, endosperm, embryos, floral tissue, pollen, and epidermal tissue.

Any scorable or screenable marker can be used in a transient assay. Preferred marker genes for transient analyses of the promoters or 5' regulatory sequences of the present invention include a GUS gene (coding sequence for β-glucuronidase) or a GFP gene (coding sequence for green fluorescent protein). The expression vectors containing the 5' regulatory sequences operably linked to a marker gene are delivered to the tissues and the tissues are analyzed by the appropriate mechanism, depending on the marker. The quantitative or qualitative analyses are used as a tool to evaluate the potential expression profile of the 5' regulatory sequences when operatively linked to genes of agronomic interest in stable plants. Ultimately, the promoter sequences of the present invention are directly incorporated into suitable plant transformation expression vectors comprising the 5' regulatory sequences operatively linked to selectable markers and genes of interest, transformed into plants and the plants analyzed for the desired expression profile conferred by the 5' regulatory sequences.

Those of skill in the art are aware of the vectors and suitable for plant transformation. Suitable vectors would include but are not limited to disarmed Ti-plasmids for Agrobacterium-mediated methods. These vectors can contain a resistance marker, 1–2 T-DNA borders, and origins of replication for *E. coli* and Agrobacterium along with one or more genes of interest and associated regulatory regions. Those of skill in the art are aware that for Agrobacterium-mediated approaches a number of strains and methods are available. Such strains would include but are not limited to Agrobacterium strains C58, LBA4404, EHA101 and EHA105. Particularly preferred strains are *Agrobacterium tumefaciens* strains. Other DNA delivery systems for plant transformation are also known to those of skill in the art and include but is not limited to particle bombardment of selected plant tissues.

Exemplary nucleic acids which may be introduced by the methods encompassed by the present invention include, for example, DNA sequences or genes from another species, or even genes or sequences which originate with or are present in the same species, but are incorporated into recipient cells by genetic engineering methods rather than classical reproduction or breeding techniques. However, the term exogenous, is also intended to refer to genes which are not normally present in the cell being transformed, or perhaps simply not present in the form, structure, etc., as found in the transforming DNA segment or gene, or genes which are normally present yet which one desires, e.g., to have overexpressed. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

The plant transformation vectors containing the promoter sequences of the present invention may be introduced into plants by any plant transformation method. Several methods are available for introducing DNA sequences into plant cells and are well known in the art. Suitable methods include but are not limited to bacterial infection, binary bacterial artificial chromosome vectors, direct delivery of DNA (e.g. via PEG-mediated transformation, desiccation/inhibition-mediated DNA uptake, electroporation, agitation with silicon carbide fibers, and acceleration of DNA coated particles (reviewed in Potrykus, Ann. Rev. Plant Physiol. Plant Mol. Biol., 42: 205, 1991).

Methods for specifically transforming dicots primarily use *Agrobacterium tumefaciens*. For example, transgenic plants reported include but are not limited to cotton (U.S. Pat. No. 5,004,863; U.S. Pat. No. 5,159,135; U.S. Pat. No. 5,518,908, WO 97/43430), soybean (U.S. Pat. No. 5,569,834; U.S. Pat. No. 5,416,011; McCabe et al., Bio/Technology, 6:923, 1988; Christou et al., Plant Physiol., 87:671, 1988); Brassica (U.S. Pat. No. 5,463,174), and peanut (Cheng et al., Plant Cell Rep., 15: 653, 1996).

Similar methods have been reported in the transformation of monocots. Transformation and plant regeneration using these methods have been described for a number of crops including but not limited to asparagus (*Asparagus officinalis*; Bytebier et al., Proc. Natl. Acad. Sci. U.S.A., 84: 5345, 1987); barley (*Hordeum vulgarae*; Wan and Lemaux, Plant Physiol., 104: 37, 1994); maize (*Zea mays*; Rhodes, C. A., et al., Science, 240: 204, 1988; Gordon-Kamm, et al., Plant Cell, 2: 603, 1990; Fromm, et al., Bio/Technology, 8: 833, 1990; Koziel, et al., Bio/Technology, 11: 194, 1993); oats (*Avena sativa*; Somers, et al., Bio/Technology, 10: 1589, 1992); orchardgrass (*Dactylis glomerata*; Horn, et al., Plant Cell Rep., 7: 469, 1988); rice (*Oryza sativa*, including indica and japonica varieties, Toriyama, et al., Bio/Technology, 6: 10, 1988; Zhang, et al., Plant Cell Rep., 7: 379, 1988; Luo and Wu, Plant Mol. Biol. Rep., 6: 165, 1988; Zhang and Wu, Theor. Appl. Genet., 76: 835, 1988; Christou, et al., Bio/Technology, 9: 957, 1991); sorghum (*Sorghum bicolor*; Casas, A. M., et al., Proc. Natl. Acad. Sci. U.S.A., 90: 11212, 1993); sugar cane (Saccharum spp.; Bower and Birch, Plant J., 2: 409, 1992); tall fescue (*Festuca arundinacea*; Wang, Z.Y. et al., Bio/Technology, 10: 691, 1992); turfgrass (*Agrostis palustris*; Zhong et al., Plant Cell Rep., 13: 1, 1993); wheat (*Triticum aestivum*; Vasil et al., Bio/Technology, 10: 667, 1992; Weeks T., et al., Plant Physiol., 102: 1077, 1993; Becker, et al., Plant, J. 5: 299, 1994), and alfalfa (Masoud, S. A., et al., Transgen. Res., 5: 313, 1996). It is apparent to those of skill in the art that a number of transformation methodologies can be used and modified for production of stable transgenic plants from any number of target crops of interest.

The transformed plants are analyzed for the presence of the genes of interest and the expression level and/or profile conferred by the promoter sequences of the present invention. Those of skill in the art are aware of the numerous methods available for the analysis of transformed plants. A variety of methods are used to assess gene expression and determine if the introduced gene(s) is integrated, functioning properly, and inherited as expected. For the present invention the promoters can be evaluated by determining the expression levels of genes to which the promoters are operatively linked. A preliminary assessment of promoter function can be determined by a transient assay method using reporter genes, but a more definitive promoter assessment can be determined from the analysis of stable plants. Methods for plant analysis include but are not limited to Southern blots or northern blots, PCR-based approaches, biochemical analyses, phenotypic screening methods, field evaluations, and immunodiagnostic assays.

The methods of the present invention including but not limited to cDNA library preparation, genomic library preparation, sequencing, sequence analyses, PCR technologies, vector construction, transient assays, and plant transformation methods are well known to those of skill in the art and are carried out using standard techniques or modifications thereof.

The following examples are included to demonstrate preferred embodiments of the invention. It should be appreciated by those of skill in the art that the techniques disclosed in the examples which follow represent techniques discovered by the inventors to function well in the practice of the invention. However, those of skill in the art should, in light of the present disclosure, appreciate that many changes can be made in the specific embodiments which are disclosed and still obtain a like or similar result without departing from the spirit and scope of the invention, therefore all matter set forth or shown in the accompanying drawings is to be interpreted as illustrative and not in a limiting sense.

EXAMPLES

Example 1
Plant Material, DNA Isolation and Library Construction

A number of tissues and plant developmental stages are selected for preparation of the corn libraries. Those of skill in the art are aware of the variations in tissue selection and preparation that occur from one tissue sampler to the next. The following are the conditions for the target libraries:

Plant Growth Conditions. Seeds are planted at a depth of about 3 cm in soil into 2"–3" pots containing Metro Mix 200 growing medium and transplanted into larger 10" pots containing the same soil after 2–3 weeks. Peters 15-16-17 fertilizer is applied abut 3 times per week after transplanting, at a strength of 150 ppm N. 2–3 times during the life of the plant from transplanting to flowering. A total of about 900 mg Fe is added to each pot. Corn plants are grown in the greenhouse in 15 hr day/9 hr night cycles. The daytime temperature is 80° F. and the night temperature is 70° F. Lighting is provided by 1000W sodium vapor lamps. Tissue Isolation. The corn immature tassel cDNA library (SATMON021) is generated from immature maize (DK604, DEKALB Genetics, Dekalb Ill., U.S.A.) tassel at the V8 plant developmental stage. The tassel is an immature tassel at about 2–3 cm in length. The tassels are collected and frozen in liquid nitrogen and the harvested tissue is stored at −80° C. until the RNA is prepared.

The corn root cDNA library (SATMON010) is generated from maize (DK604, DEKALB Genetics, Dekalb Ill., U.S.A.) root tissue. at the V8 plant developmental stage. The root tissue is collected when the corn plant is at the 8-leaf stage. The root system is cut from the plant and rinsed with water to remove the soil. The tissue is frozen in liquid nitrogen and the harvested tissue is stored at −80° C. until the RNA is prepared.

The corn leaf cDNA library (SATMON004) is generated from maize (B73×Mo17, Illinois Foundation Seeds, Champaign, Ill. U.S.A.) total leaf tissue at the V6 plant developmental stage. The older leaves in the basal position and the younger leaves in the upper positions are all cut at the leaf base. The leaves are pooled and immediately frozen in liquid nitrogen and crushed. The harvested tissue is stored at −80° C. until the RNA is prepared.

The corn primary root cDNA library (SATMON007) is generated from the primary root tissue of maize (DK604, DEKALB Genetics, Dekalb, Ill. U.S.A) 5 day old seedlings. The seeds are planted on a moist filter paper on a covered tray kept in the dark until germination (one day). After germination, the tray containing the moist filter paper is moved to the greenhouse at a 15 hour day/9 hour night cycle and grown until the seedlings are 5 days old. The day temperature is 80° F. and the night temperature is 70° F. The tissue is collected when the seedlings are 5 days old. At this stage, the primary root (radicle) has pushed through the coleorhiza which has pushed through the seed coat. The primary root which is about 2–3 cm long is cut and frozen in liquid nitrogen. The harvested tissue is stored at −80° C. until the RNA is prepared.

The corn primary shoot cDNA library (SATMON008) is generated from the primary shoot (coleoptile 2–3 cm) of maize (DK604, DEKALB Genetics, Dekalb, Ill. U.S.A.) seedlings which are approximately 5 days old (same conditions described for primary root library). The coleoptile is dissected away from the rest of the seedling and immediately frozen in liquid nitrogen and stored at −80° C. until the RNA is prepared.

The corn undeveloped leaf cDNA library (SATMON011) is generated from maize (DK604, DEKALB Genetics, Dekalb, Ill. U.S.A.). The tissue is collected when the corn plant is at a 6-leaf developmental stage. The second youngest leaf which is at the base of the apical leaf of the V6 corn plant is cut at the base and immediately transferred to liquid nitrogen containers and the leaves are crushed. The harvested tissue is stored at −80° C. until the RNA is prepared.

The corn meristem cDNA library (SATMON013) is generated from maize (DK604, DEKALB Genetics, Dekalb, Ill. U.S.A.). The corn plant is at a 4-leaf stage. The leaf at the apex of the V4 stage corn plant is known as the meristem founder. This apical meristem founder is cut and immediately frozen in liquid nitrogen and crushed. The harvested tissue is then stored at −80° C. until the RNA is prepared.

The corn sheath cDNA library (SATMON016) is generated from maize (DK604, DEKALB Genetics, Dekalb, Ill. U.S.A.). Sheath tissue is collected from the corn plant at the V8 stage. When the maize plants are at the V8 stage the 5th and 6th leaves from the base of the plant have fully developed leaf blades. At the base of these leaves, the ligule is differentiated and the leaf blade is joined to the sheath. The sheath is dissected away from the base of the leaf and frozen in liquid nitrogen crushed. The tissue is stored at −80° C. until RNA preparation.

The corn culm (stem) cDNA library (SATMON019) is generated from maize (DK604, DEKALB Genetics, Dekalb, Ill. U.S.A.). The corn plant is at a V8 developmental stage and the 5th and 6th leaves from the bottom have fully developed leaf blades. The region between the nodes of the 5th and 6th leaves from the bottom is the region of the stem that is collected. The leaves are pulled out and the sheath is also torn away from the stem. This stem tissue is completely freed of any leaf and sheath tissue. The tissue is frozen in liquid nitrogen and stored at −80° C. until the RNA is prepared.

The corn immature tassel cDNA library (SATMON001) is generated from maize (B73, Illinois Foundation Seeds, Champaign, Ill. U.S.A.). Corn immature tassels are collected at the V6 developmental stage. Tassels which are 2–3 cm in length are collected and frozen in liquid nitrogen. The harvested tissue is stored at −80° C. until the RNA is prepared.

The corn ear cDNA library (SATMON023) is generated from maize (DK604, DEKALB Genetics, Dekalb, Ill.

U.S.A.). Tissue is collected when the plant is in the V8 stage. The length of the ear that is harvested is about 10–15 cm and the silks are just exposed (approximately one inch). The ear along with the silks is frozen in liquid nitrogen and the tissue is stored at 80° C. until the RNA is prepared.

The corn etiolated seedling cDNA library (SATMON029) is generated from maize (DK604, DEKALB Genetics, Dekalb, Ill. U.S.A.). Seeds are planted on a moist filter paper on a covered tray and kept in the dark for 4 days. The daytime temperature is about 80° F. and the nighttime temperature is about 70° F. The tissue is collected when the seedlings are 4 days old. All the structures of the seedlings appear thin and elongated. The primary root has penetrated the colerhiza and is about 4–5 cm in length. Secondary lateral roots have also appeared. The coleoptile has also pushed through the seed coat and is about 4–5 cm long. The seedlings are then frozen in liquid nitrogen and crushed. The harvested tissue is then stored at −80° C. until the RNA is prepared.

The corn endosperm cDNA library (twenty-two days after pollination or 22-DAP) (SATMON036) is generated from maize RX601. The growth conditions are as follows: Corn seeds are sterilized for 1 minute in 10% Clorox solution, rolled in germination paper, and germinated in 0.5 mM calcium sulfate for two days at 30° C. The seedlings are transplanted into a peat mix media in 3" pots at the rate of three seedlings per pot. The seedlings are grown in the greenhouse and twenty pots are placed in a high CO2 environment (~1000 ppm CO2) and twenty plants are grown under about 450 ppm CO2. The plants are hand watered and lightly fertilized with Peters 20–20–20. At 10 days after planting, the shoots from both atmospheres are placed in liquid nitrogen and light ground by hand. The roots are rinsed in distilled water to remove most of the support media, and frozen in liquid nitrogen. The tissues are stored at −80° C. until RNA is prepared.

For preparation of the cDNA libraries, the RNA is purified using Trizol reagent available from Life Technologies (Gaithersburg, Md.) essentially as recommended by the manufacturer. Poly A+RNA (mRNA) is purified using magnetic oligo dT beads essentially as recommended by the manufacturer (Dynabeads, Dynal Corporation, Lake Success, N.Y.).

Construction of cDNA libraries is well-known in the art and a number of cloning strategies exist. A number of cDNA library construction kits are commercially available. The Superscript™ Plasmid System for cDNA synthesis and Plasmid Cloning (Gibco BRL, Life Technologies, Gaithersburg, Md.) is used, following the conditions suggested by the manufacturer.

The cDNA libraries are plated on LB agar containing the appropriate antibiotics for selection and incubated at 37° C. for a sufficient time to allow the growth of individual colonies. Single colonies are individually placed in each well of a 96-well microtiter plate containing LB liquid including selective antibiotics. The plates are incubated overnight at approximately 37° C. with gentle shaking to promote growth of the cultures. The plasmid DNA is isolated from each clone using Qiaprep Plasmid Isolation kits, using the conditions recommended by the manufacturer (Qiagen Inc., Santa Clara, Calif.).

Template plasmid DNA clones are used for subsequent sequencing. For sequencing, the ABI PRISM dRhodamine Terminator Cycle Sequencing Ready Reaction Kit with AmpliTaq® DNA Polymerase, FS, is used (PE Applied Biosystems, Foster City, Calif.).

Example 2

Promoter Identification

The database of EST sequences derived from the cDNA libraries prepared from various corn tissues is used to identify the promoter candidates for expression of operably linked DNA sequences in multiple tissues. The sequences are also used as query sequences against GenBank databases which contain previously identified and annotated sequences and searched for regions of homology using BLAST programs. The selection of expressed sequence tags (ESTs) for subsequent promoter isolation is reflective of the presence of one or more sequences among the representative ESTs from a random sampling of an individual cDNA library or collection of cDNA libraries. To identify regulatory sequences that regulate the expression of transcripts in the target tissues of interest from EST sequences in the database, a subsetting function is done, requesting ESTs found in target libraries such as leaf, ear, culm, tassel, meristem, root and seedling. For promoters of expression of glyphosate tolerance genes, a search is performed particularly selecting libraries from reproductive and rapidly dividing tissues, since suitable 5' regulatory sequences for vegetative and reproductive tolerance can be identified. The chosen targets are subjected to an electronic northern function in which the putative tissue expression profile and abundance levels in a library for a given EST is displayed. Target ESTs with the desired expression profile and abundance levels are identified and gene specific primers are designed based on the identified EST sequence. Percent abundance relates to the number of times the members of a group of related sequences appears in a library the EST is derived from. A number of parameters can be selected to obtain the selected ESTs and will depend upon the EST database and computer programs available for sequence analyses and queries. For the promoters or 5' regulatory sequences of SEQ ID NOS: 53–75, a percent abundance in the selected libraries of about 0.05 to 0.50 is used.

Table 1 provides background clone ID (EST) information, library sources, and GenBank identifier (g) information for the ESTs used for subsequent isolation of the promoter sequences of SEQ ID NOS: 54–75. Sequence annotation is listed for clone IDs based on a GenBank BLAST search with a p-value cut-off of 10–8. The information is subject to change as new sequences are submitted to the sequence databases. The annotations for the ESTs are listed as follows with the annotation information in parentheses: Clone ID 700333814 (corn mRNA for cysteine proteinase, clone CCP, complete cds); Clone ID 700806028 (maize mRNA for enolase); Clone ID 700210506 (*H. vulgare* mRNA for UDP glucose pyrophosphorylase); Clone ID 700043360 (Maize pyruvate, orthophosphate dikinase mRNA, complete cds); Clone ID 700094769 (Wheat mRNA for cytosolic phosphoglycerate kinase); Clone ID 700150082 (*Z. mays* strain B73 Beta-D-glucosidase mRNA, nuclear gene encoding chloroplast protein, complete cds); Clone ID 700094721 (Wheat mRNA for cytosolic phosphoglycerate kinase); Clone ID 700164347 (*Z. mays* W-22 histone H2A mRNA complete cds), two clones (SEQ ID NO:53 and SEQ ID NO:54 which contains about 2.0 kb of additional sequence); Clone ID 700154443 (*Z. mays* elongation factor 1-alpha); Clone ID 700017196 (*Z. mays* gene for cyclophilin); Clone ID 700342364 (*Z. mays* mRNA for translation initiation factor 5A); Clone ID 700342580 (*Z. mays* MNB 1b mRNA for DNA-binding protein); Clone ID 700342746 (*Z. mays* ribosomal protein S8 mRNA, complete cds); Clone ID 700164205 (*Z. mays* DnaJ-related protein ZMDJ1 (mdJ1) gene, complete cds); Clone ID 700343485 (*Sorghum bicolor* heat shock protein 70 cognate (hsc70) mRNA, partial cds); Clone ID 700345557 (*Z. mays* ubiquitin conjugating enzyme (UBC) mRNA, complete cds); Clone ID 700345819 (*Z. mays* superoxide dismutase 4A (sod4A) gene, complete cds); Clone ID 700345704 (*V. faba* guanine nucleotide regulatory protein mRNA, complete cds).

TABLE 1

Promoter Summary Information

| SEQ. ID NO. | Clone ID Number | Library Source | GenBank Identifier (g) |
|---|---|---|---|
| 57 | 700046047 | leaf | g1532072 |
| 62 | 700333814 | culm (stem) | g643596 |
| 58 | 700806028 | endosperm, 22-DAP | g22272 |
| 61 | 700210506 | sheath | g212995 |
| 59 | 700043360 | leaf | g168579 |
| 60 | 700094769 | primary shoot | g21834 |
| 63 | 700150082 | primary root | g4096601 |
| 64 | 700094721 | primary shoot | g21834 |
| 53 | 700164347 | meristem | g473602 |
| 54 | 700164347 | meristem | g473602 |
| 55 | 700154443 | primary root | g2282583 |
| 56 | 700017196 | immature tassel | g829147 |
| 65 | 700342364 | immature tassel | g1546918 |
| 72 | 700342580 | immature tassel | g397395 |
| 73 | 700342976 | immature tassel | none |
| 66 | 700342746 | immature tassel | g1498052 |
| 75 | 700350638 | ear, growing silks | none |
| 67 | 700342649 | immature tassel | none |
| 68 | 700164205 | meristem | g2984708 |
| 69 | 700343485 | immature tassel | g1181672 |
| 70 | 700345557 | immature tassel | g2668743 |
| 71 | 700345819 | immature tassel | g1899026 |
| 74 | 700345704 | immature tassel | g395071 |

Example 3

Genomic Library Construction, PCR Amplification and Promoter Isolation

For genomic libraries, corn DNA (from maize hybrid Fr27xFrMo17) is isolated by a CsCl purification protocol according to Ausubel et al., 1992, by a CTAB purification method (Rogers and Bendich, Plant Mol. Biol., 5:69, 1988) or a similar DNA isolation method suitable for the isolation of plant DNA. Reagents are available commercially (see, for example Sigma Chemical Co., St. Louis, Mo.). The libraries are prepared according to manufacturer instructions (GENOME WALKER, a trademark of CLONTECH Laboratories, Inc, Palo Alto, Calif.). In separate reactions, genomic DNA is subjected to restriction enzyme digestion overnight at 37° C. with the following blunt-end endonucleases: EcoRV, ScaI, DraI, PvuII, or StuI (CLONTECH Laboratories, Inc. Palo Alto, Calif.). The reaction mixtures are extracted with phenol:chloroform, ethanol precipitated, and resuspended in Tris-EDTA buffer. The purified blunt-ended genomic DNA fragments are then ligated to the GenomeWalker™ adaptors and ligation of the resulting DNA fragments to adaptors were done according to manufacturer protocol. The GenomeWalker™ sublibraries are aliquoted and stored at −20° C.

Genomic DNA ligated to the GenomeWalker™ adaptor (above) is subjected to a primary round of PCR amplification with gene-specific primer 1 (GSP1) and a primer which anneals to the adaptor sequence, adaptor primer 1 (AP1) SEQ ID NO:1. A diluted (1:50) aliquot of the primary PCR reaction is used as the input DNA for a nested round of PCR amplification with gene-specific primer 2 (GSP2) and adaptor primer 2 (AP2) SEQ ID NO:2, or adaptor primer 3 (AP3) SEQ ID NO:3. The annealing temperatures of the GenomeWalker™ primary primer (AP1) and nested primer (AP2) are 59° C. and 71° C., respectively. Generally, gene specific primers are designed to have the following characteristics: 26–30 nucleotides in length, GC content of 40–60% with resulting temperatures for most of the gene specific primers in the high 60° C. range or about 70° C. The Taq polymerase used is Amplitaq Gold™, available through Perkin-Elmer Biosystems (Branchbury, N.J.). A number of temperature cycling instruments and reagent kits are commercially available for performing PCR experiments and include those available from PE Biosystems (Foster City, Calif.), Strategene (La Jolla, Calif.), and MJ Research Inc. (Watertown, Mass.). Following the primary PCR reaction, an aliquot is taken (10–15 µl) for agarose gel analysis. Isolation of each unknown sequence required amplification from 5 sub-genomic libraries and a negative control (without DNA).

The PCR components and conditions generally used are outlined below:

| Component | Amount/Volume required |
|---|---|
| PRIMARY PCR (Method 1) | |
| Sub-library aliquot | 1 µl |
| Gene-specific primer 1 | 1 µl (100 pmol) |
| Genome Walker ™ Adaptor primer 1 (AP1) | 1 µl |
| dNTP mix (10 mM of each dNTP) | 1 µl |
| DMSO | 2.5 µl (or 2–5% final concentration) |
| 10X PCR buffer (containing MgCl2) | 5 µl (final concentration of 1X) |
| Amplitaq Gold ™ | 0.5 µl |
| Distilled Water | For final reaction volume of 50 µl |

Reaction Conditions for Primary PCR:

A. 9 minutes at 95° C.
B. 94° C. for 2 seconds, 70° C. for 3 minutes; repeat 94° C./70° C. cycling for total of 7 times
C. 94° C. for 2 seconds, 65° C. for 3 minutes; repeat 94° C./65° C. cycling for total of 36 times
D. 65° C. for 4 minutes as a final extension
E. 10° C. for an extended incubation NESTED PCR (secondary PCR reaction)

| | |
|---|---|
| 1:50 dilution of the primary PCR reaction | 1 µl |
| Gene-specific primer 2 | 1 µl (100 pmol) |
| Genome Walker ™ Adaptor primer 2 or 3 (AP2 or AP3)) | 1 µl |
| dNTP mix (10 mM of each dNTP) | |
| DMSO | 2.5 µl |
| 10X PCR buffer (containing MgCl2) | 5 µl (final concentration of 1X) |
| Amplitaq Gold ™ | 0.5 µl |
| Distilled water | to final reaction volume of 50 µl |

Reaction Conditions for Nested PCR:

A. 9 minutes at 95° C.
B. 94° C. for 2 seconds, 70° C. for 3 minutes; repeat 94° C./70° C. cycling for total of 5 times
C. 94° C. for 2 seconds, 65° C. for 3 minutes; repeat 94° C./65° C. cycling for total of 24 times
D. 65° C. for 4 minutes as a final extension
E. 10° C. for an extended incubation Those of skill in the art are aware of the variations in PCR conditions including choice of polymerase, cycling conditions and concentrations of the reaction components. Other modifications to the above procedure include the use of Expand High Fidelity polymerase (Boehringer Mannheim, Indianapolis, Ind.), Taq polymerase (Promega Corp., Madison, Wis.) and slight variations in temperature are outlined below:

| MODIFICATION 1: Polymerase (Expand High Fidelity, Boehringer Mannheim, IN) |
| --- |

Primary PCR reaction step 1 95° C. 2 min
step 2 94° C. 2 sec
step 3 72° C. 3 min
step 4 repeat step 2 and 3, 7 times
step 5 94° C. 2 sec
step 6 68° C. 3 min
step 7 repeat steps 5 and 6, 36 times Secondary PCR reaction step 1, step 2, step 3 (same as primary PCR reaction)
step 4 repeat step 2 and 3, 5 times
step 5 and step 6 (same as primary PCR reaction)
step 7 repeat step 5 and step 6, 24 times

| MODIFICATION 2: Polymerase (Amplitaq Gold ™, Perkin Elmer, Foster City, CA) |
| --- |

Primary PCR reaction step 1 95° C. 10 min
step 2 94° C. 2 sec
step 3 70° C. 3 min
step 4 repeat step 2 and 3, 7 times
step 5 94° C. 2 sec
step 6 68° C. 3 min
step 7 repeat step 5 and step 6, 24 times

| MODIFICATION 3: Polymerase enzyme is Taq (Promega Corp., Madison, WI) |
| --- | same cycle conditions as Modification 2 except step 1 is 2 minutes.

| MODIFICATION 4: Polymerase enzyme is AccuTaq (Sigma, St. Louis, MO) |
| --- | same cycle conditions as Modification 3.

| MODIFICATION 5: Polymerase is Expand High Fidelity (BM) | | |
| --- | --- | --- |
| Mixture | Primary PCR | Secondary PCR |
| 10X PCR buffer 2 | 2 μl | 1 μl |
| dNTP | 1 μl | |
| adaptor primer (10 mM) | 1 μl<br>AP1 | 1 μl |
| gene specific primer (10 mM) | 1 μl<br>GSP1 | 1 μl<br>GSP2 |
| Polymerase | 2.5 units | 3.5 units |
| template DNA | Genome Walker ™ library<br>1 μl | 1:50 of primary PCR product |
| H2O | to<br>20 μl | to<br>50 μl |

| Modification 5: PCR Cycling Conditions: |
| --- |
| step 1 94° C. 1 min |
| step 2 94° C. 2 sec |
| step 3 70° C. 3 min |
| step 4 repeat step 2 another 5 cycles |
| step 5 94° C. 2 sec |
| step 6 68° C. 3 min |
| step 7 repeat step 5 another 34 cycles |
| step 8 68° C. 10 min |
| step 9 10° C. hold |

| MODIFICATION 6: PCR Conditions |
| --- | step 1 95° C. 2 min
step 2 94° C. 30 sec
step 3 65° C. 30 sec, decrease 1° C. each cycle for 14 cycles
step 4 72° C. 3 minutes
step 5 repeat 2–4, 14 times
step 6 50° C.
step 7 72° C.
step 8 repeat 6–7, 15 times Modification 5 is used for the isolation of promoter sequence SEQ ID NO: 53 (clone ID #700164347). SEQ ID NO: 1 is combined with GSP1 SEQ ID NO: 6 in the primary PCR reaction. For the nested PCR reaction SEQ ID NO: 2 is combined with GSP2 SEQ ID NO: 7 in the secondary PCR reaction and a PCR product is isolated.

Modification 5 is used for the isolation of promoter sequence SEQ ID NO: 54 (clone ID #700164347 that contains additional 2 kb of 5' sequence). SEQ ID NO: 1 is combined with GSP1 SEQ ID NO: 6 in the primary PCR reaction. For the nested PCR reaction, SEQ ID No. 2 is combined with GSP2 SEQ ID NO: 7 in the secondary PCR reaction and a PCR product is isolated.

Modification 5 is used for the isolation of promoter sequence SEQ ID NO: 55 (clone ID #700154443). SEQ ID NO: 1 is combined with GSP1 SEQ ID NO: 8 in the primary PCR reaction. For the nested PCR reaction, SEQ ID NO: 2 is combined with GSP2 SEQ ID No. 9 in the secondary PCR reaction and a PCR product is isolated.

Modification 5 is used for the isolation of promoter sequence SEQ ID NO: 56 (clone ID #700017196). SEQ ID No. 1 is combined with GSP1 SEQ ID NO: 10 in the primary PCR reaction. For the nested PCR reaction, SEQ ID No. 2 is combined with GSP2 SEQ ID NO: 11 in the secondary PCR reaction and a PCR product is isolated.

PCR method 1 is used for the isolation of promoter sequence SEQ ID NO:62 (clone ID #700333814) SEQ ID NO:1 is combined with GSP1 SEQ ID NO: 22 in the primary PCR reaction. For the nested PCR reaction, SEQ ID NO: 2 is combined with GSP2 SEQ ID NO: 23 in the secondary PCR reaction and a PCR product is isolated.

PCR method 1 is used for the isolation of promoter sequence SEQ ID NO: 59 (clone ID #700043360). SEQ ID NO: 1 is combined with GSP1 SEQ ID NO: 16 in the primary PCR reaction. For the nested PCR reaction, SEQ ID NO: 2 is combined with GSP2 SEQ ID NO: 17 in the secondary PCR reaction and a PCR product is isolated.

PCR method 1 is used for the isolation of promoter sequence SEQ ID NO: 60 (clone ID #700094769) SEQ ID NO: 1 is combined with GSP1 SEQ ID NO: 18 in the primary PCR reaction. For the nested PCR reaction, SEQ ID NO: 2 is combined with GSP2 SEQ ID NO: 19 in the secondary PCR reaction and a PCR product is isolated.

PCR method 1 is used for the isolation of promoter sequence SEQ ID NO: 61 (clone ID #700210506) SEQ ID NO: 1 is combined with GSP1 SEQ ID NO: 20 in a primary PCR reaction. For the nested PCR reaction, SEQ ID NO: 2 is combined with GSP2 SEQ ID NO: 21 in the secondary PCR reaction and a PCR product is isolated.

PCR method 1 is used for the isolation of promoter sequence SEQ ID NO: 57 (clone ID #700046047) SEQ ID NO: 1 is combined with GSP1 SEQ ID NO:12 in the primary PCR reaction. For a nested PCR reaction, SEQ ID NO: 2 is combined with GSP2 SEQ ID NO: 13 in the secondary PCR reaction and the PCR product is isolated.

PCR method 1 is used for the isolation of promoter sequence SEQ ID NO: 58 (clone ID #700806028). SEQ ID NO: 1 is combined with SEQ ID NO: 14 in the primary PCR reaction. For the nested PCR reaction, SEQ ID NO: 2 is combined with SEQ ID NO: 15 in the secondary PCR reaction and a PCR product is isolated.

PCR method 1 is used for the isolation of promoter sequence SEQ ID NO: 63 (clone ID #700150082). SEQ ID NO: 1 is combined with GSP1 SEQ ID NO: 24 in the primary PCR reaction. For the nested PCR reaction, SEQ ID NO: 2 is combined with GSP2 SEQ ID NO: 25 in the secondary PCR reaction and a PCR product is isolated.

PCR method 1 is used for the isolation of promoter sequence SEQ ID NO: 64 (clone ID #70094721). SEQ ID NO: 1 is combined with GSP1 SEQ ID NO: 26 in the primary PCR reaction. For the nested PCR reaction, SEQ ID NO: 2 is combined with GSP2 SEQ ID NO: 27 in the secondary PCR reaction and a PCR product is isolated.

For the isolation of promoter sequence SEQ ID NO: 65 (clone ID #700342364), GSP1 primer SEQ ID NO: 28 is combined with SEQ ID NO: 1 in a primary PCR reaction according to PCR modification 1. For the secondary PCR reaction nested primer SEQ ID NO: 2. is combined with GSP2 primer SEQ ID NO: 29 and a PCR product is isolated, cloned into a pGEM-T easy vector (Promega, Madison, Wis.), and transformed into E. coli HB101. To introduce a StuI restriction site at the 3' end and a HindIII site at the 5' end of the promoter, the pGEM-T promoter clone is used as the template in a PCR reaction using method 6 with SEQ ID NO: 3 and GSP primer SEQ ID NO: 30.

For the isolation of promoter sequence SEQ ID NO: 66 (clone ID #700342746), GSP1 SEQ ID NO: 31 is combined with SEQ ID NO: 1 in a primary PCR reaction according to PCR modification 1. For the secondary PCR reaction nested primer SEQ ID NO: 2 is combined with GSP2 SEQ ID NO: 32 and a PCR product is isolated (~1.2 kb PCR product using the DraI digested genomic library). To introduce a StuI site at the 3' end and a HindIII site at the 5' end of the promoter the promoter clone is used as a template in a PCR reaction using method 6 with adapter primer SEQ ID NO: 3 and GSP primer SEQ ID NO: 33. The PCR product is isolated and cloned into pGEM-T easy (Promega Corp., Madison, Wis.).

For the isolation of promoter sequence SEQ ID NO: 67 (clone ID #700342649), GSP1 SEQ ID NO: 34 is combined with SEQ ID NO: 1 in a primary PCR reaction according to PCR Modification 2. For the secondary PCR reaction nested primer SEQ ID NO: 2 is combined with GSP2 SEQ ID NO: 35 and the PCR product is isolated. To introduce a StuI site at the 3' end and a HindIII site at the 5' end, the promoter clone is used as the template in a PCR reaction using method 6 with adapter primer SEQ ID NO: 3 and GSP primer SEQ ID NO: 33.

For the isolation of SEQ ID NO: 68 (clone ID #700164205), GSP1 SEQ ID NO: 37 is combined with SEQ ID NO: 1 in a primary PCR reaction according to PCR Modification 3. For the secondary PCR reaction nested primer SEQ ID NO: 3. is combined with GSP2 primer SEQ ID NO: 38 and a PCR product is isolated (~0.5 kb PCR product using the StuI digested genomic library) and cloned into pGEM-T Easy (Promega Corp., Madison, Wis.).

For the isolation of promoter sequence SEQ ID NO: 69 (clone ID #700343485), GSP1 SEQ ID NO: 39 is combined with SEQ ID NO: 1 in a primary PCR reaction according to PCR Modification 3. For the secondary PCR reaction nested primer SEQ ID NO: 3 is combined with GSP2 SEQ ID NO: 40 and the PCR product is isolated and cloned into pGEM-T Easy (Promega Corp., Madison, Wis.).

For the isolation of promoter SEQ ID NO: 70 (clone ID #700345557), GSP1 SEQ ID NO: 41 is combined with SEQ ID NO: 1 in a primary PCR reaction according to PCR Modification 3. For the secondary PCR reaction nested primer SEQ ID NO: 3 is combined with GSP2 SEQ ID NO:42 and the PCR product is isolated.

For the isolation of promoter sequence SEQ ID NO:71, (clone ID #700345819) GSP1 SEQ ID NO: 43 is combined with SEQ ID NO: 1 in a primary PCR reaction according to PCR Modification 3. For the secondary PCR reaction nested primer SEQ ID NO: 3 is combined with GSP2 SEQ ID NO: 44 and a PCR product is isolated using the EcoRV digested library).

For the isolation of promoter sequence SEQ ID NO: 72 (clone ID #700342580), GSP1 SEQ ID NO: 45 is combined with SEQ ID NO: 1 in a primary PCR reaction according to PCR Modification 4. For the secondary PCR reaction nested primer SEQ ID NO: 3 is combined with GSP2 SEQ ID NO: 46. An ~2.2 kb PCR product is isolated using the ScaI digested library.

For the isolation of promoter sequence SEQ ID NO: 73 (clone ID #700342976), GSP1 SEQ ID NO: 47 is combined with SEQ ID NO: 1 according to PCR Modification 4. For the secondary PCR reaction nested primer SEQ ID NO: 3 is combined with GSP2 SEQ ID NO: 48. An ~4.0 kb PCR product is isolated using the ScaI digested library.

For the isolation of promoter sequence SEQ ID NO: 74 (clone ID #700345704), GSP1 SEQ ID NO: 49 is combined with SEQ ID NO: 1 in a primary PCR reaction according to PCR Modification 4. For the secondary PCR reaction nested primer SEQ ID NO: 3 is combined with GSP2 SEQ ID NO: 50. An ~1.3 kb PCR product is isolated using the EcoRV digested library.

For the isolation of promoter sequence SEQ ID NO: 75 (clone ID #700350638), GSP1 SEQ ID NO: 51 is combined with SEQ ID NO: 1 in a primary PCR reaction according to PCR Modification 4. For the secondary PCR reaction nested primer SEQ ID NO: 3 is combined with GSP2 SEQ ID NO: 52. An ~1.0 kb PCR product is isolated using the StuI digested library (PCR Method 4).

Example 4

Promoter Isolation and Cloning

The DNA fragments resulting from the nested PCR amplification described above are isolated and gel purified. A 40 µl aliquot of the secondary PCR is run on an agarose gel. The DNA fragment of the secondary PCR product is purified from the agarose gel using the BIO101 Geneclean II Kit (Midwest Scientific, Valley Park, Mo.) following the conditions suggested by the manufacturer. The purified DNA is ligated to pGEM-T Easy vector (pGEM-T Easy Vector System I, Promega Corp., Madison, Wis.) following the conditions recommended by the manufacturer. An aliquot of the ligation reaction is transformed into a suitable E. coli host such as DH10B and the cells plated on selection medium (for DH10B, 100: g/ml carbenicillin). Bacterial transformants are selected, grown in liquid culture, and the plasmid DNA isolated using a commercially available kit such as the Qiaprep Spin Miniprep Kit (Qiagen Corp., Valencia, Calif.). Purified plasmid containing the predicted insert size based on restriction enzyme analysis are sequenced using the dye terminator method in both directions using the M13 forward and reverse primers shown in SEQ ID NO: 4 (M13 forward primer) and SEQ ID NO: 5 (M13 reverse primer). Restriction enzymes are available from a number of manufacturers (see for example, Boehringer Mannheim (Indianapolis, Ind.). The 5' flanking region containing the promoter sequence is determined and shown in SEQ ID NOS: 53–75. Engineering restriction sites for cloning into suitable vectors generally use the PCR method outlined in method 6, using standard molecular biology techniques known to those of skill in the art.

Example 5
Plant cell Analysis of Promoter Activity

Figure 3:
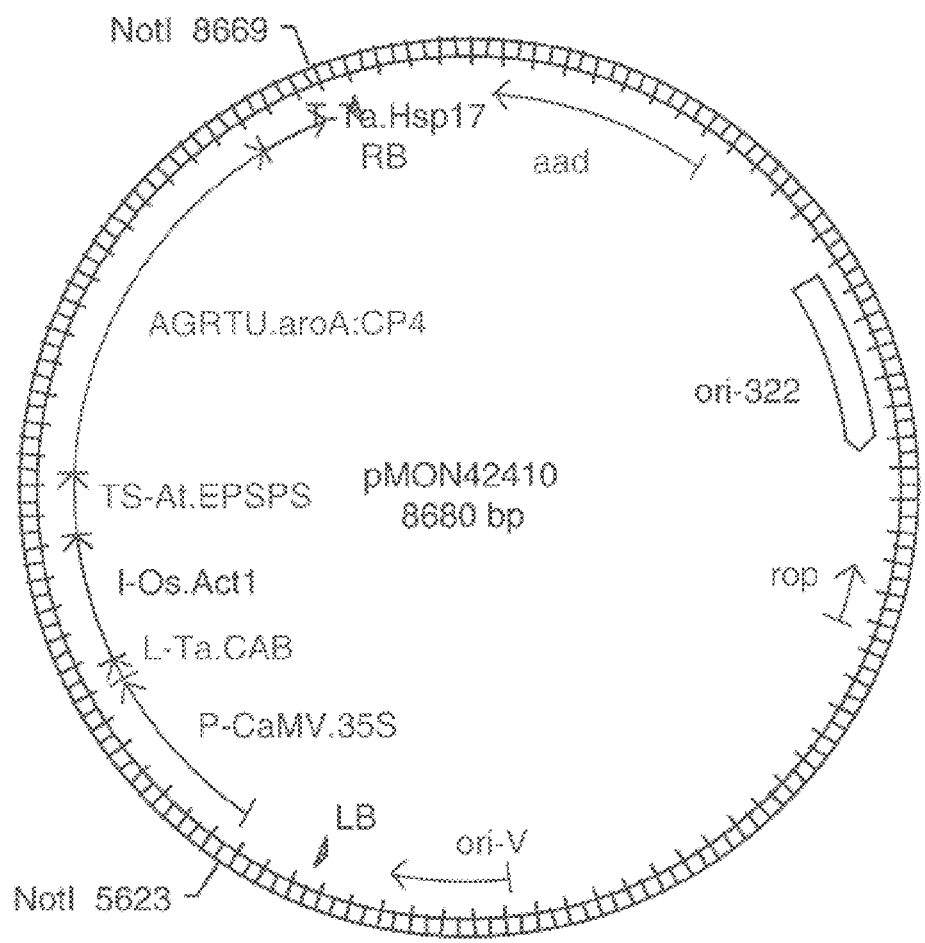
FIG. 3 is a plasmid map of pMON42410
Figure 4:
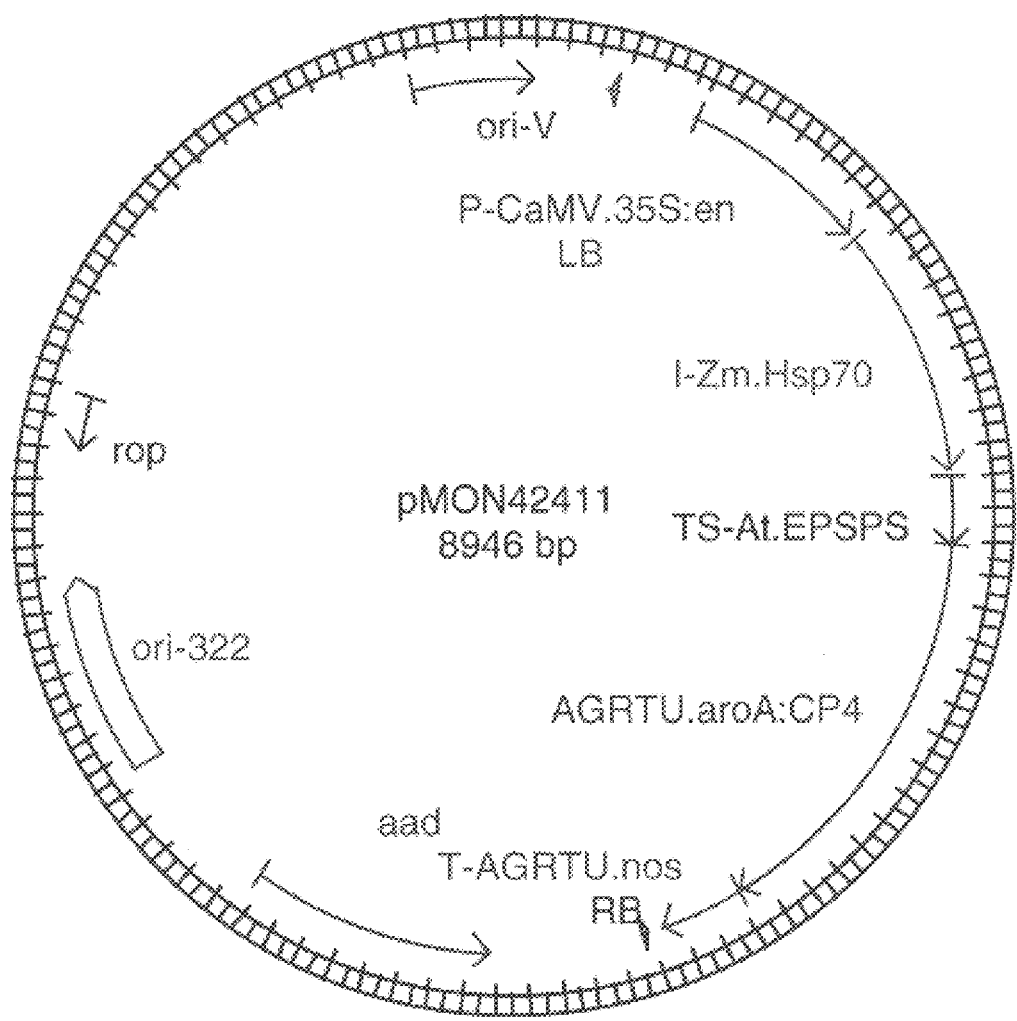
FIG. 4 is a plasmid map of pMON42411
Figure 5:
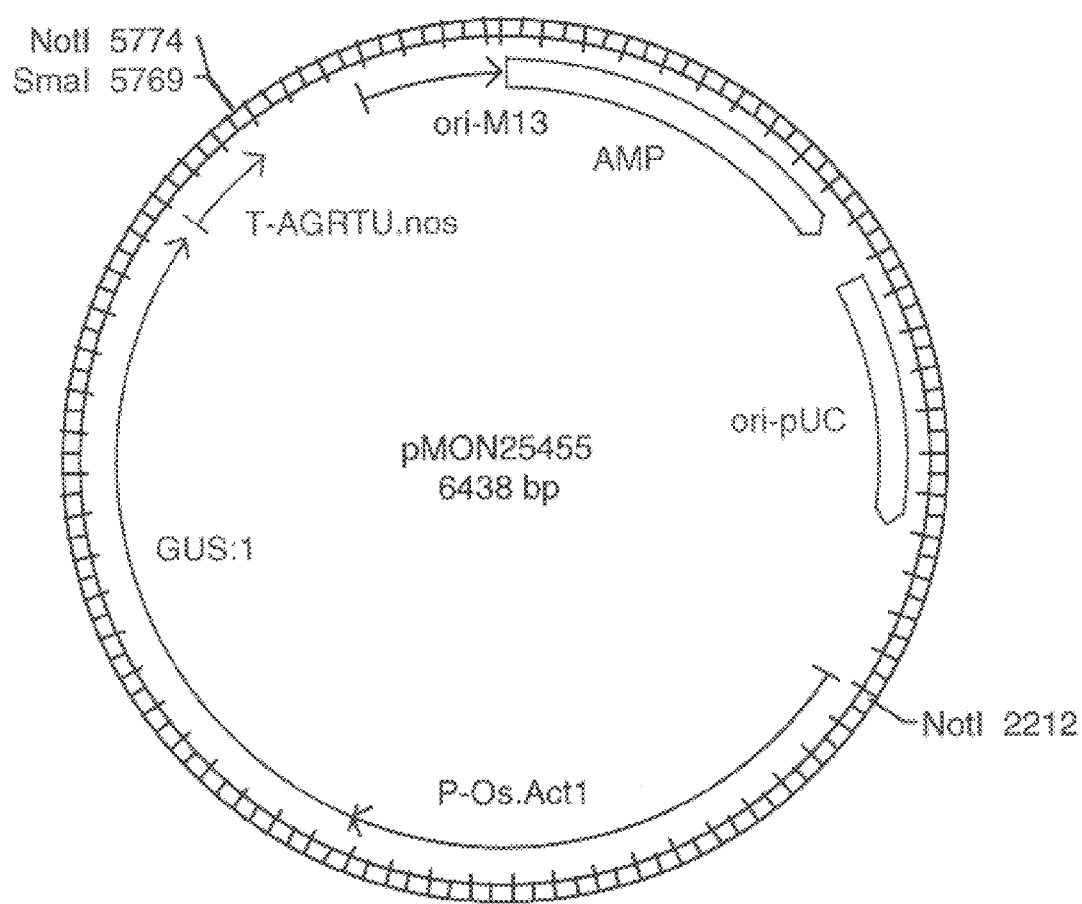
FIG. 5 is a plasmid map of pMON25455
Figure 6:
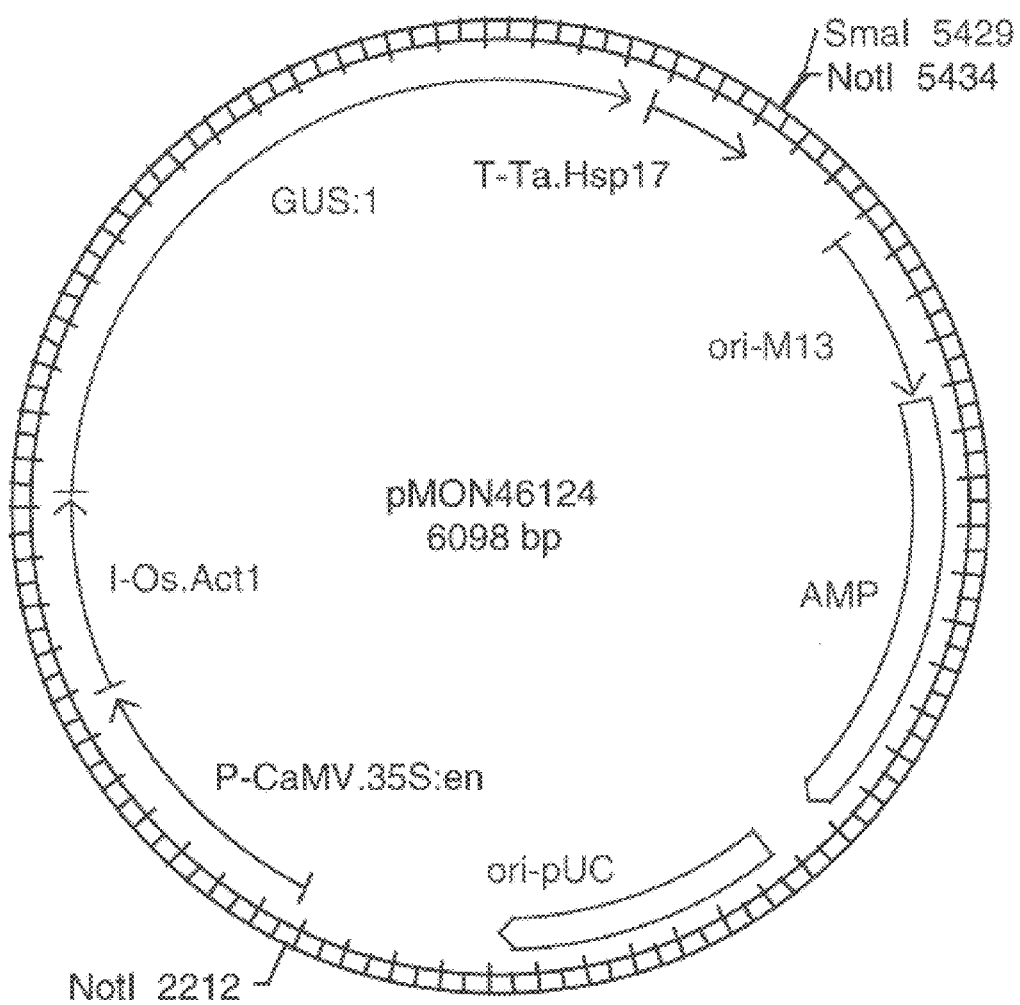
FIG. 6 is a plasmid map of pMON46124

For plant cell expression, promoter fragments are cloned into expression vectors such pMON19469 as shown in FIG. 1. Plasmid pMON19469 is an expression vector consisting of the following genetic components: P-CaMV.35S:en is the promoter for the 35S RNA from Cauliflower mosaic virus containing a duplication of the −90 to −300 region; I-Zm.Hsp70 is an intron of the maize heat shock protein as described in U.S. Pat. Nos. 5,593,874 herein incorporated by reference in its entirety and U.S. Pat. No. 5,859,347 herein incorporated by reference in its entirety; Ec.GUS:1 (GUS:1) is the coding region for β-glucuronidase; T-AGRTU.nos is the termination signal from the nopaline synthase gene isolated from *Agrobacterium tumefaciens*; ori-M 13 and ori-pUC are origins of replication; AMP is the regulatory region for ampicillin selection. If an AUG of a target promoter is identified, the fragment is cloned into pMON19469 in place of the P-CaMV.35S:en genetic element. If an AUG is not identified, the promoter fragment is cloned into an expression vector modified to enable translational fusions with a reporter gene such as β-glucuronidase (GUS) (Jefferson et al., EMBO J., 6:3901, 1987) or green fluorescent protein (GFP) as described in Pang et al., Plant Physiol. 112:893 (1996). pMON25455 (FIG. 5) is a basic expression vector consisting of the rice actin promoter from Act1 gene, the GUS:1 coding sequence and the T-AGRTU.nos terminator. Additional basic expression vectors containing various expression elements include but are not limited to pMON42410 (FIG. 3), pMON42411 (FIG. 4), and pMON46124 (FIG. 6). The promoter DNA fragments of the present invention can replace the promoter elements of the basic expression vector to determine the promoter activity of the DNA fragments.

The promoter DNA fragments that are clone ID #s 70094769 (SEQ ID NO.60), 70094721 (SEQ ID NO.64), 700342746 (SEQ ID NO.66), 700342364 (SEQ ID NO. 65), 700350638 (SEQ ID NO. 75), 700164205 (SEQ ID NO. 68), 700343485 (SEQ ID NO. 69), 700345557 (SEQ ID NO. 70), 700345819 (SEQ ID NO. 71), 7003442580 (SEQ ID NO. 72), 700342976 (SEQ ID NO. 73), 700345704 (SEQ ID NO. 74), are cloned into the GUS containing basic expression constructs by restriction enzyme digestion and DNA ligase treatment of the fragments under the appropriate conditions well known by those of skill in the art of molecular biology. The purified plasmid DNA of the resulting expression cassettes are tested in a corn protoplast electroporation assay for GUS activity. A number of assays are available and known to those of skill in the art. Analysis of reporter genes in a protoplast system can be used to assess the activity of a regulatory element, such as a promoter operably linked to the reporter gene. A leaf protoplast isolation and electroporation protocol is followed essentially as described by Sheen, (Plant Cell 3:225–245, 1991) with the following modifications: The seed used is FR27RHM×FRMo17RHM from Illinois Foundation Seeds. The seed is surface sterilized for 2 minutes in 95% ethanol, rinsed twice with sterile water, 30 minutes in 50% bleach (Clorox) plus 2 drops of Tween-20, three rinses in sterile water followed by a 5 minute soak in benlate/captan solution to prevent fungal growth. The seeds are germinated in phytotrays containing 100 mls ½ MS media (2.2 g/L MS salts, 0.25% gelrite), 7 seeds per phytotray. The seeds are grown 5 days at 26° C. in 16/8 hour day/night photoperiod and 7 days in the dark at 28° C. The second leaf from each plant is sliced longitudinally using Feather no. 11 surgical blades. Digestion time is two hours and 10 minutes in the light at 26° C. After digestion, the plates are swirled two times at 80–100 rpm for 20 seconds each and the protoplast/enzyme solution is pipetted through a 190 μm tissue collector. Protoplasts are counted using a hemacytometer counting only protoplasts that are intact and circular. Ten to fifty micrograms of DNA containing the vector of interest is added per cuvette. Final protoplast densities at electroporation range from 3×106/ml to 4.5×106/ml. Electroporations are performed in the light using Bio-rad Gene pulser cuvettes (Bio/Rad Hercules, Calif.) with a 0.4 cm gap and a maximum volume of 0.8 ml at 125 μFarads capacitance and 260 volts. The protoplasts are incubated on ice after resuspension in electroporation buffer and are kept on ice in cuvettes until 10 minutes after electroporation. The protoplasts are kept at room temperature for ten minutes before adding 7 mls of protoplast growth media. The protoplast culture media has been described (Fromm et al., Methods in Enzymology 153, 351–366, 1987). Culture plates are layered with growth media and 1.5% SeaPlaque agarose (FMC BioProducts, Rockland, Me.) to prevent protoplast loss. Samples are cultured in the light at 26° C., 16/8 day/night cycle, until harvested for the assay (typically 18–22 hours after electroporation). Samples are pipetted from the petri plates to 15 ml centrifuge tubes and harvested by centrifugation at 800–1000 rpm. The supernatant is removed and samples are assayed immediately for the gene of interest. Samples can also be frozen for later analysis.

The expression of GUS by the DNA promoters of the present invention is measured as a percentage of the activity observed when the basic expression vector, pMON25455 (P-Os.Act1/GUS/AGRTU.nos) is electroporated into corn protoplasts (Table 2). The MUG assays provided a quantitative analysis of the GUS expression in the transgenic plant cells. Total protein was extracted from each sample. The MUG assay used 500 μl of GUS extraction buffer added to the tissues, and tissues were ground with a teflon pestle in 1.5 ml eppendorf tube and centrifuged at 10K RPM for 5min at 4 degree (Beckman GS-15R). 400 μl of supernatant was transferred to a fresh 96-deep well plate. The extracts are frozen on dry ice and stored at −80 till use. The MUG assay consisted of generating a standard curve of activity with a serial dilution of 4-methyl umbelliferone ( Sigma Chemical Co M1381) from 31.2 pmoles to 2000 pmoles. 5 μl of each extract was added to a flat bottom 96-well plate (Falcon 3872) in duplicate after the plant was preread for blanking the background. 200 μl of GUS assay solution (0.1M $KPO_4$ pH7.8, 1.0 mM EDTA, 5% glycerol, 10.0 mM DTT, 2mM 4-methyl umbelliferyl glucuronide Fluka 69602) was added to each well and mixed with the samples by pipetting. The Plate was read kinetically on a F-max (Molecular Devices) at 37° C. with the filter pair: excitiation-355/emission-460. A typical read consists of 21 readings at 3 min intervals and last 1 hour. GUS activity (pmol/min/μg protein) was calculated base on MUG results and protein results of each sample. Total protein was assayed using Bio-Rad Protein Assay kit. Serial dilutions of BSA protein from 0.05 mg/ml to 0.5 mg/ml were used for the standard curve. 1.5 μl of extracts was added to flat bottom 96-well plate (Falcon) in duplicate. 200 ul of diluted dye reagent was added and mixed with the samples. The absorbance at 595 nm was measured in Spectromax 250 (Molecular Devices) at room temperature after 5 min incubation at room temperature.

Figure 9:
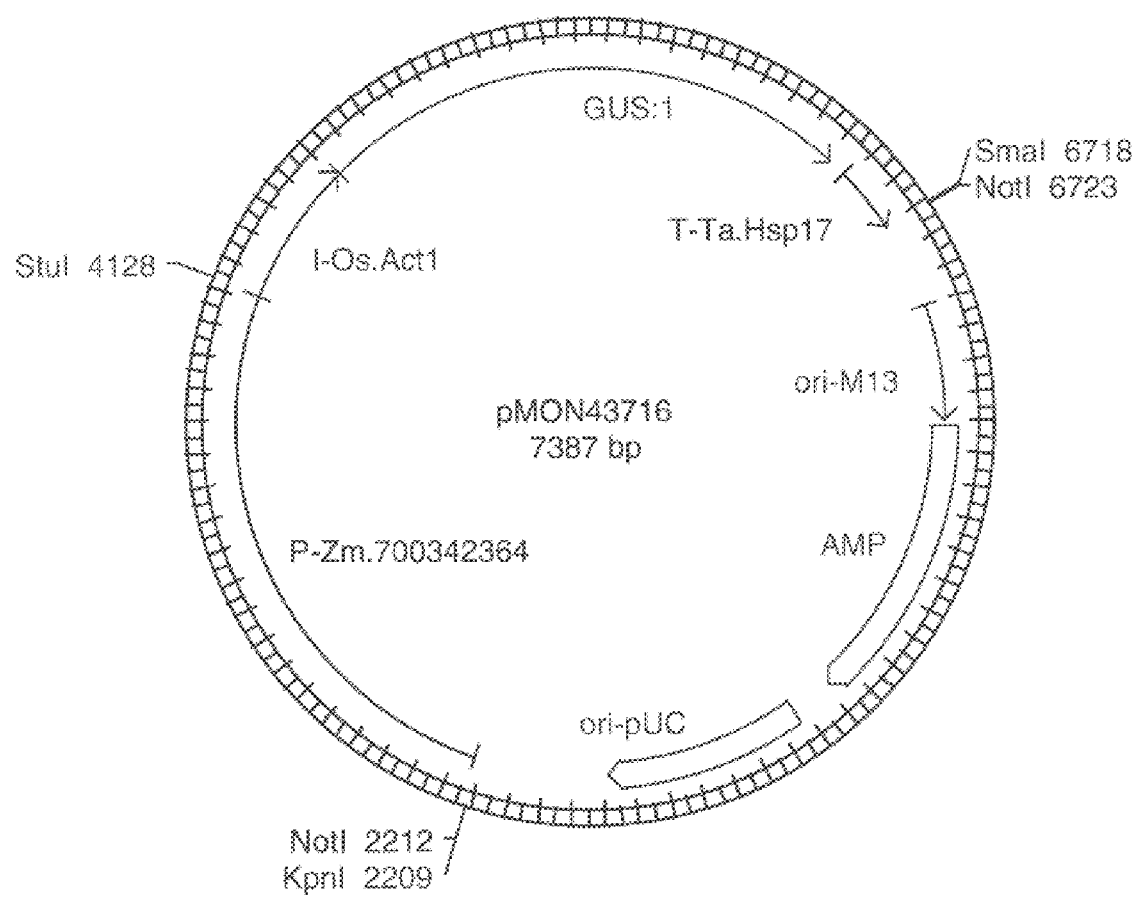
FIG. 9 is a plasmid map of pMON43716
Figure 12:
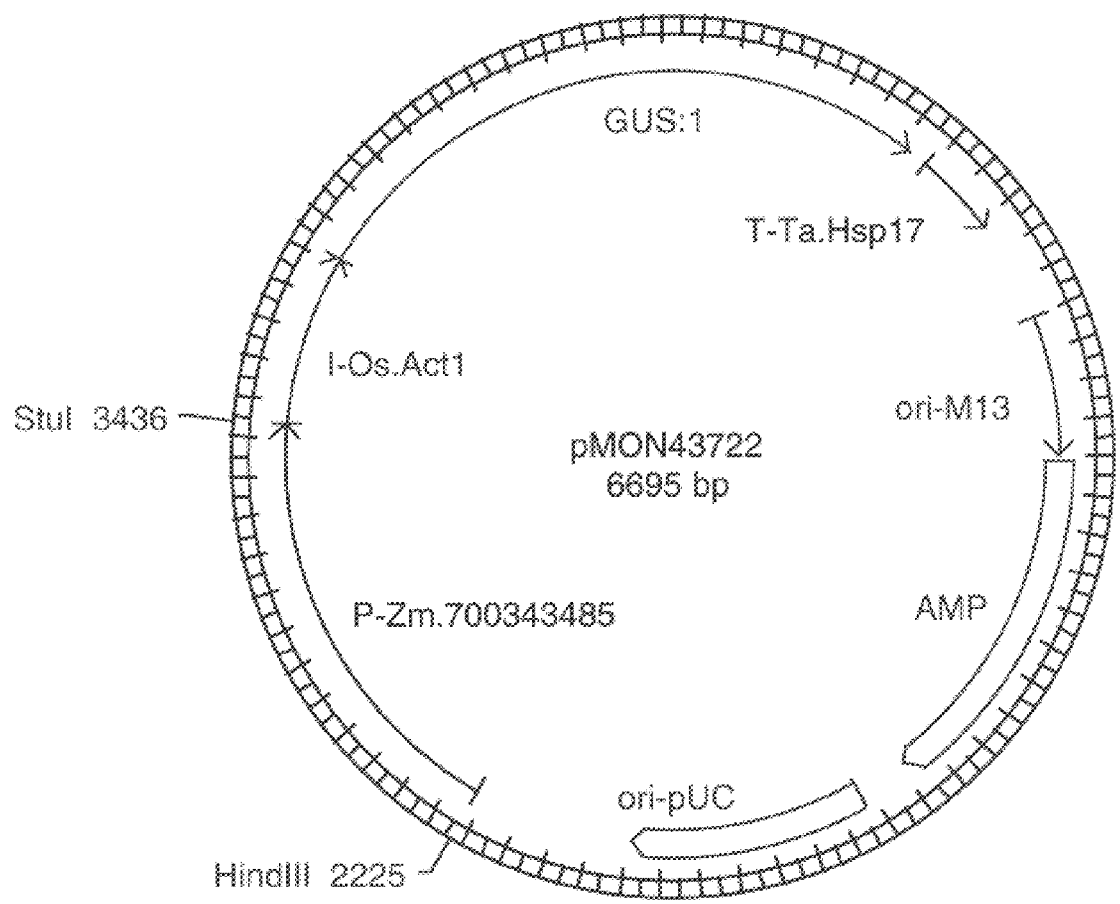
FIG. 12 is a plasmid map of pMON43722

Three experiments (1, 2, and 3) with 2 replications each were conducted to assay the expression of the 10 promoter sequences as shown in Table 2. This analysis identified 4 promoter sequences that are equal to or higher than that observed from the rice actin 1 promoter sequence, these expression cassettes are contained in pMON43716 (FIG. 9), pMON43722 (FIG. 12), pMON43734 (P-Zm.700342976/I-Os.Act1/GUS/T-Ta.Hsp17), and pMON43736 (P-Zm.700345704/I-Os.Act1/GUS/T-Ta.Hsp 17).

TABLE 2

Corn protoplast analysis of DNA promoter sequences driving expression of GUS:1

| | pMON | Promoter Fragment, ~Kb | GUS (% Os.Act1/GUS) 1 | 2 | 3 |
|---|---|---|---|---|---|
| 1 700342746 SEQ ID NO.66 | 43710 | 1.2 | 1, 2 | | |
| 2 700342364 SEQ ID NO.65 | 43716 | 2.0 | 66, 145 | 126, 111 | |
| 3 700350638 SEQ ID NO.75 | 43730 | 1.0 | | 24, 32 | |
| 4 700164205 SEQ ID NO.68 | 43720 | 0.5 | | 16, 17 | |
| 5 700343485 SEQ ID NO.69 | 43722 | 1.3 | | 232, 275 | |
| 6 700345557 SEQ ID NO.70 | 43726 | 1.5 | | 26, 29 | |
| 7 700345819 SEQ ID NO.71 | 43728 | 0.6 | | 47, 54 | |
| 8 700342580 SEQ ID NO.72 | 43732 | 2.2 | | 7, NA | |
| 9 700342976 SEQ ID NO.73 | 43734 | 4.0 | | | 118, 100 |
| 10 700345704 SEQ ID NO.74 | 43736 | 1.2 | | | 300, 409 |
| CaMV.35S | 46124 | | 484, 573 | 831, 682 | 1445, 1081 |
| Os.Act1 | 25455 | | 100 | 100 | 100 |

Example 6
Transformation of Wheat with Plant Expression Vectors Comprising DNA Promoter Sequences of the Present Invention.

Figure 2:
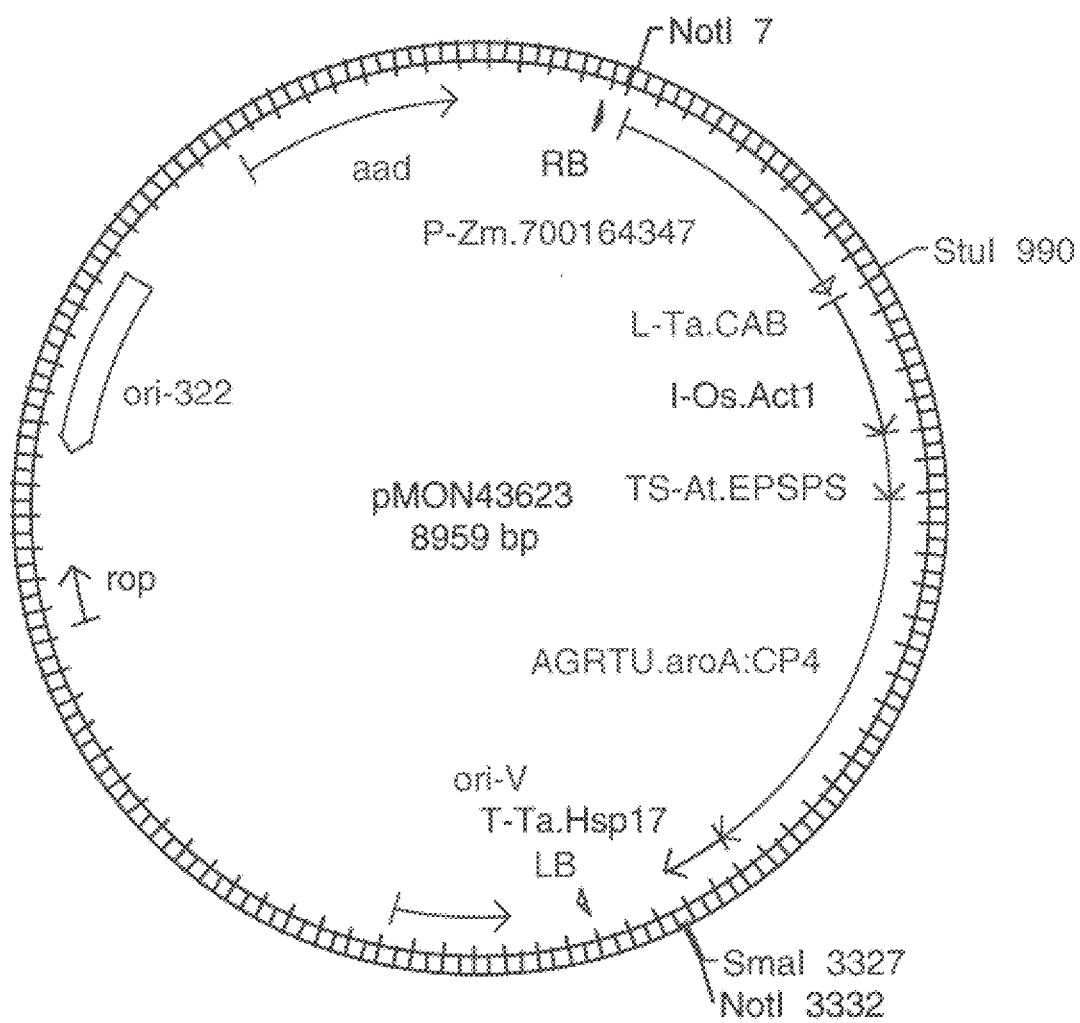
FIG. 2 is a plasmid map of pMON43623
Figure 7:
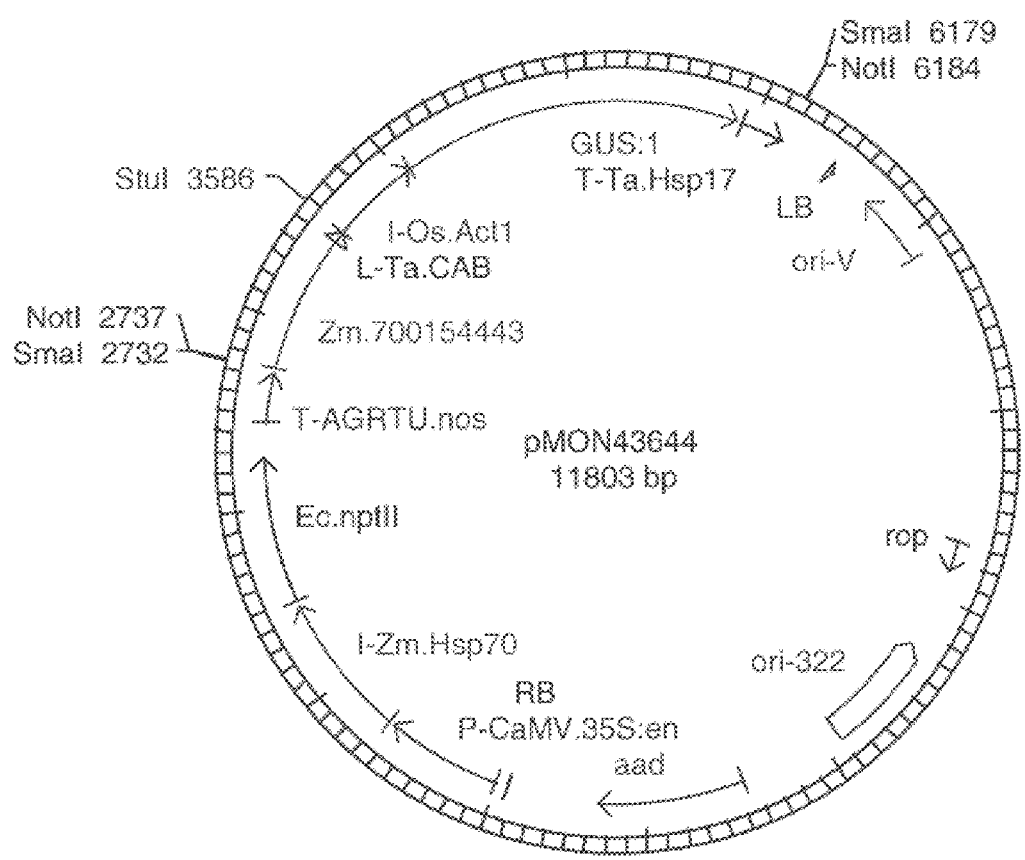
FIG. 7 is a plasmid map of pMON43644
Figure 8:
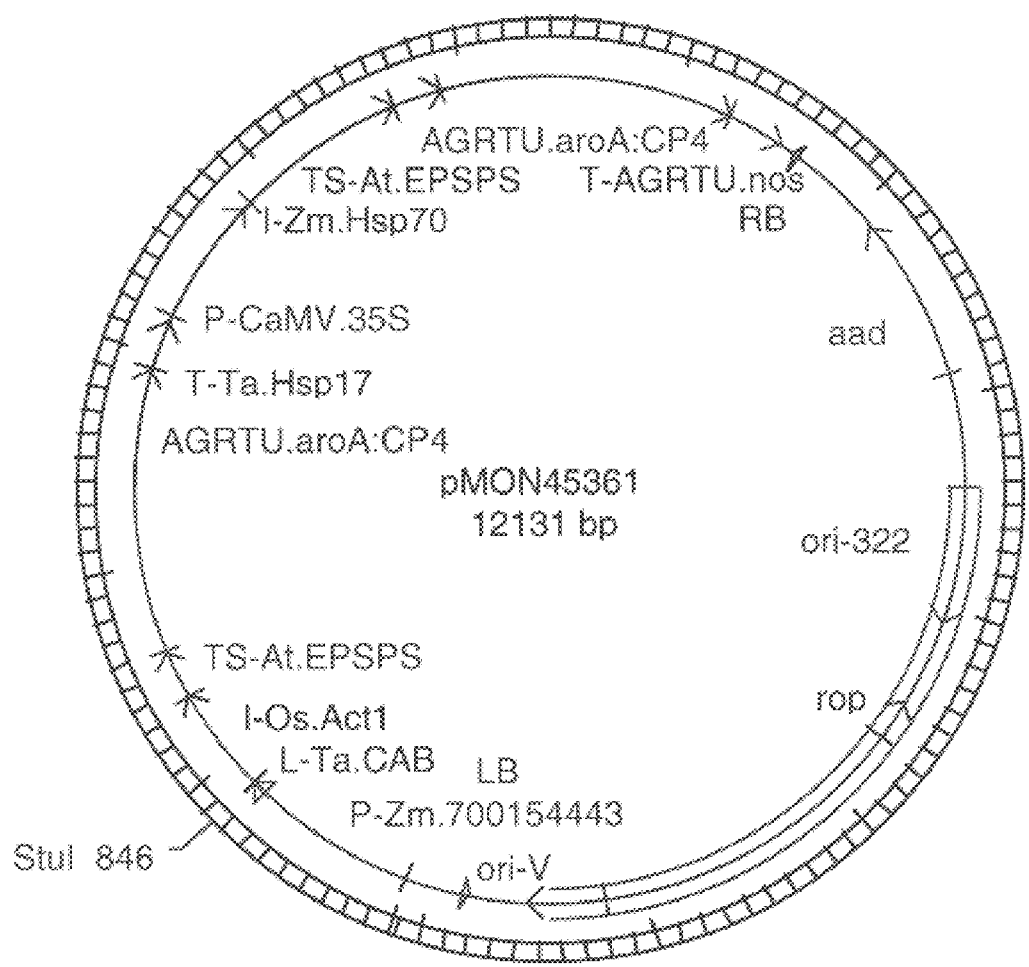
FIG. 8 is a plasmid map of pMON45361
Figure 10:
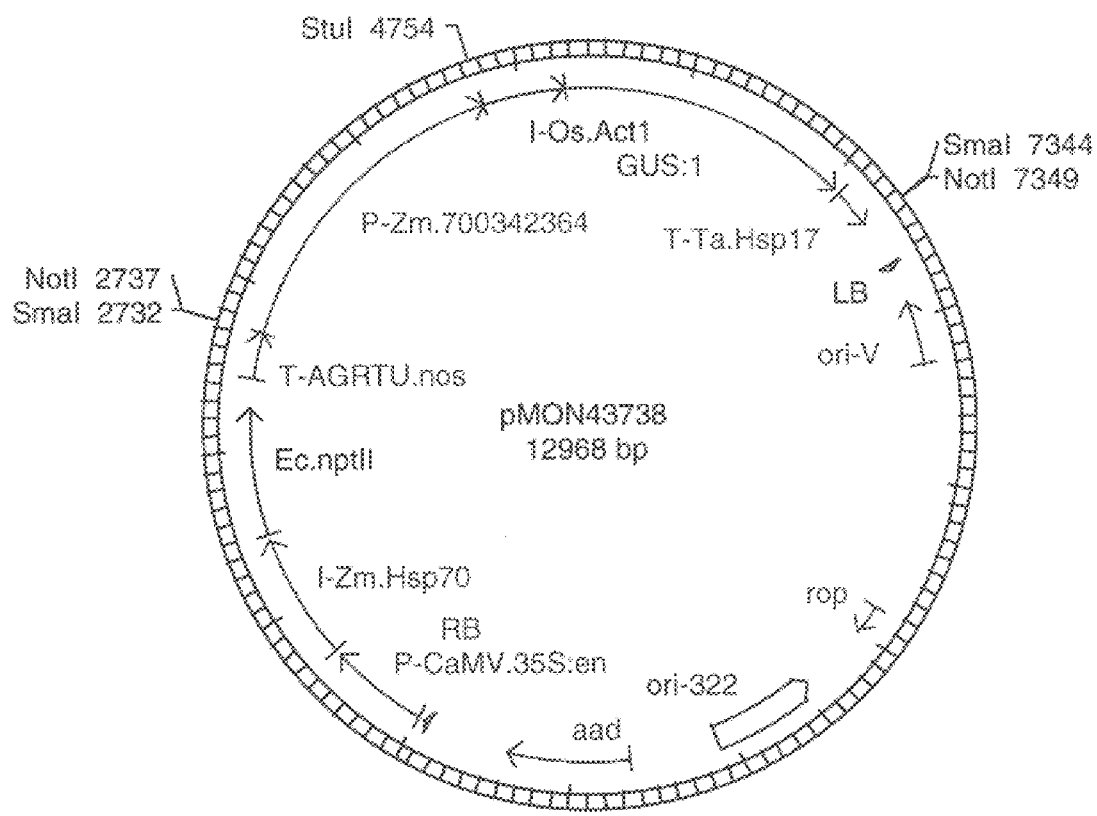
FIG. 10 is a plasmid map of pMON43738
Figure 11:
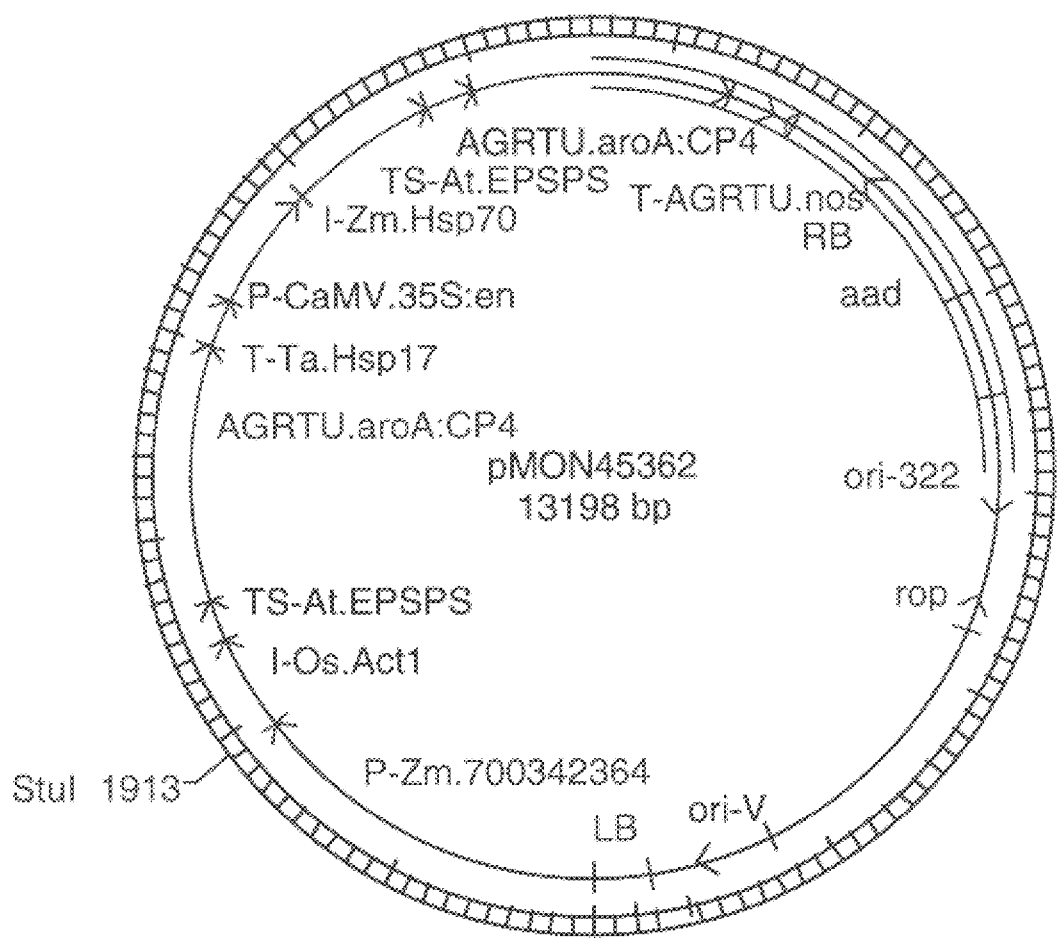
FIG. 11 is a plasmid map of pMON45362
Figure 13:
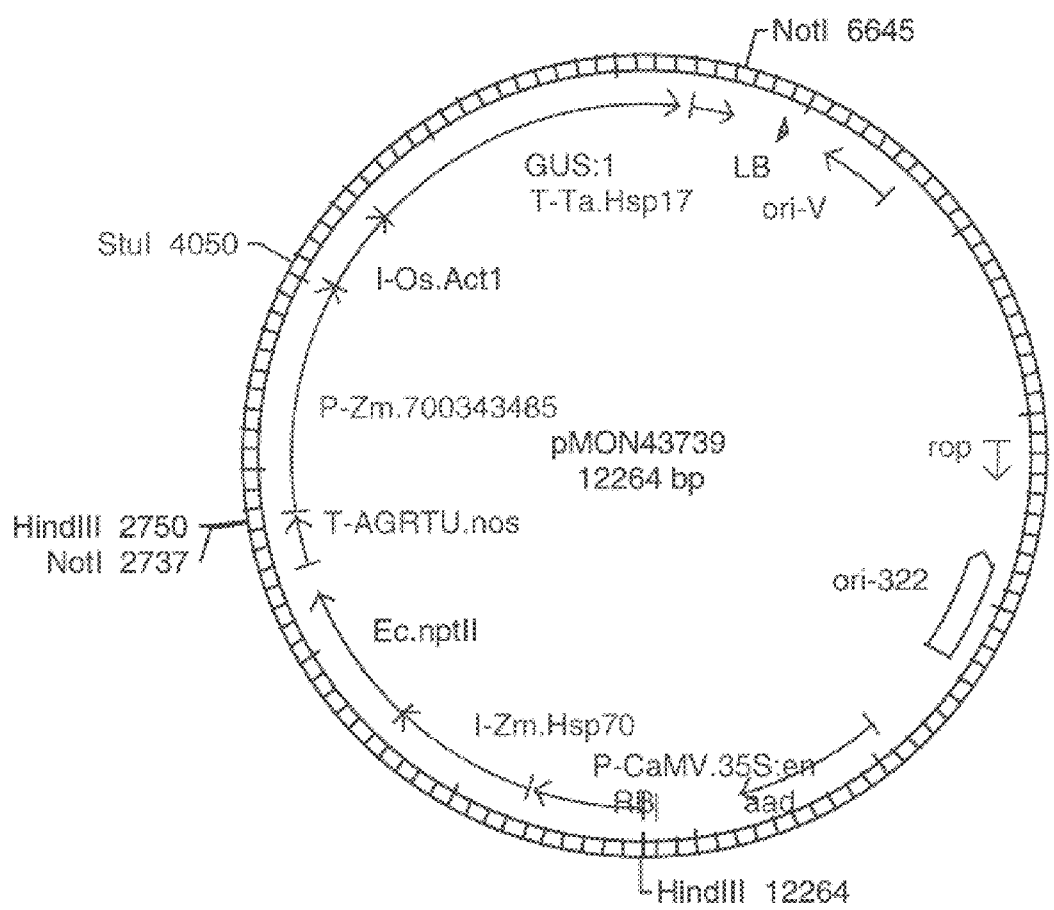
FIG. 13 is a plasmid map of pMON43739
Figure 14:
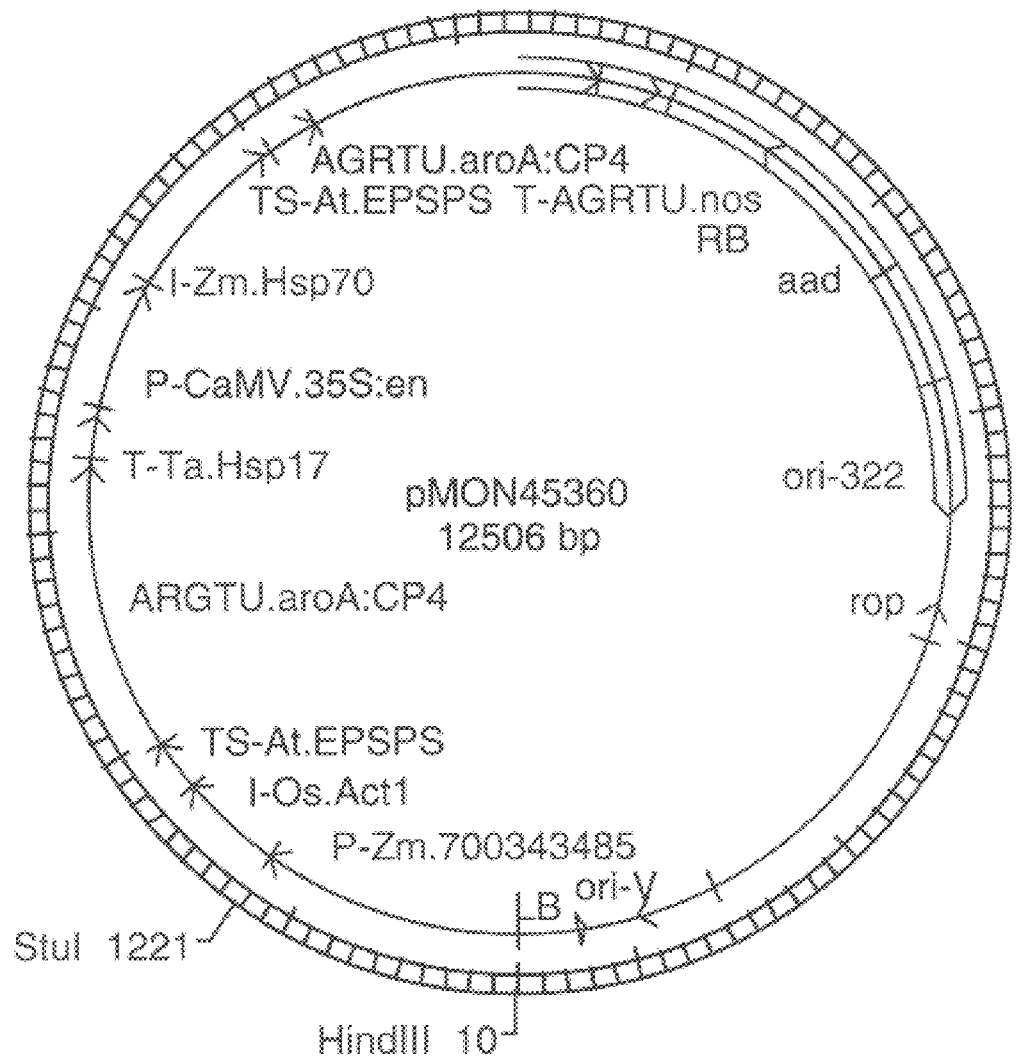
FIG. 14 is a plasmid map of pMON45360

Wheat cells are transformed with DNA vectors containing the DNA promoter sequences of the present invention expressing GUS:1 reporter coding sequence. pMON43644 (clone ID #700154443) FIG. 7, pMON43738 (clone ID #700342364) FIG. 10 and pMON43739 (clone ID #700343485) FIG. 13 express the GUS gene in the leaves, ovaries and anthers of transgenic wheat plants. Wheat plants are transformed with DNA promoter sequences of the present invention expressing the AGRTU.aroA:CP4 (CP4) coding sequence of a glyphosate EPSPS enzyme for conferring glyphosate tolerance to transgenic wheat plants. Wheat plants containing pMON45360 (P-Zm.700343485/I-Os.Act/CP4/Ta.hsp17::P-CaMV.35S/Zm.Hsp70/CP4/T-AGRTU.nos) FIG. 14, a double expression cassette vector with the P-Zm.700343485 promoter driving expression of the CP4 EPSPS coding sequence and the P-CaMV.35S promoter driving expression of an additional copy of the CP4 EPSPS coding sequence; pMON45361 (P-Zm.700154443/Ta.CAB/I-Os.Act/CP4/Ta.Hsp17::P-CaMV.35S/Zm.Hsp70/CP4/T-AGRTU.nos) FIG. 8, a double expression cassette vector with the P-Zm.70015443 promoter driving expression of the CP4 EPSPS coding sequence and the P-CaMV.35S promoter driving expression of an additional copy of the CP4 EPSPS coding sequence; pMON45362 (P-Zm.700342364/I-Os.Act/CP4/Ta.Hsp17::P-CaMV.35S/Zm.Hsp70/CP4/T-AGRTU.nos) FIG. 11, a double expression cassette vector with the P-Zm.700342364 promoter driving expression of the CP4 EPSPS coding sequence and the P-CaMV.35S promoter driving expression of an additional copy of the CP4 EPSPS coding sequence; pMON43623 (P-700164347/Ta.CAB/I-Os.Act/CP4/Ta.Hsp17) FIG. 2, a single expression cassette vector with the P-Zm.700164347 promoter driving expression of the CP4 EPSPS coding sequence. These vectors and control vectors, pMON42411 (FIG. 4), pMON42410 (FIG. 3) and pMON30167 (P-Os.Act/I-Os.Act/CP4/T-AGRTU.nos) are transformed into wheat cells by the following method.

Immature embryos of wheat (*Triticum aestivum* L) cv Bobwhite are isolated from the immature caryopsis 13–15 days after pollination, and cultured on CM4C (Table 3) for 3–4 days.

The embryos showing active cell division, but no apparent callus formation are selected for Agrobacterium infection.

TABLE 3

Supplemental Components in Basal Media[1]

| Components | CM4 | CM4C | MMS.2C | MMS0 |
|---|---|---|---|---|
| 2,4-D (mg/l) | 0.5 | 0.5 | 0.2 | — |
| Pichloram (mg/l)[2] | | 2.2 | 2.2 | |
| Maltose (g/l) | 40.0 | 40.0 | 40.0 | 40.0 |
| Glutamine (g/l) | | 0.5 | 0.5 | |
| Magnesium Chloride (g/l) | | 0.75 | 0.7 | |
| Casein Hydrolysate (g/l) | | 0.1 | 0.1 | |
| MES (g/l) | | 1.95 | 1.95 | 1.95 |
| Ascorbic Acid (mg/l)[2] | | 100.0 | 100.0 | 100.0 |
| Gelling Agent (g/l)[3] | 2(P) | 2(P) | 2(G) | 2(G) |

[1]All media contain basal salts (MS basal salts) and vitamins (MS vitamins) from Murashige and Skoog (1962). The pH in each medium is adjusted to 5.8.
[2]Filter-sterilized and added to the medium after autoclaving.
[3]Phytagel ™ (P) or Gelrite ® (G).

A disarmed Agrobacterium strain C58 (ABI) harboring a binary vector of interest (pMON45367, FIG. 5) is used for all the experiments. The pMON vectors are transferred into Agrobacterium by a triparental mating method (Ditta et al., Proc. Natl. Acad. Sci. 77:7347–7351). Liquid cultures of Agrobacterium are initiated from glycerol stocks or from a freshly streaked plate and grown overnight at 26° C.–28° C. with shaking (approximately 150 rpm) to mid-log phase ($OD_{660}$=1–1.5) in liquid LB medium, pH 7.0 containing 50 mg/l kanamycin, 50 mg/l streptomycin and spectinomycin and 25 mg/l chloramphenicol with 200 µM acetosyringone (AS). The Agrobacterium cells are resuspended in the inoculation medium (liquid CM4C) and the density is adjusted to $OD_{660}$ of 1. The immature embryos cultured in CM4C medium are transferred into sterile petri plates (16×20 mm) or wells of a 6-well cell culture plate (Costar Corporation, Cambridge, Mass.) containing 10 ml of inoculation medium per petri plate or 5 ml per cell culture cluster plate. An equal amount of the Agrobacterium cell suspension is added such that the final concentration of Agrobacterium cells is an $OD_{600}$ of 0.5. In most experiments, pluronic F68 is added to the inoculation mixture at a final concentration of 0.01 %. The ratio between the Agrobacterium and immature embryos (IEs) is about 10 ml: 20–200 IEs. The inoculation is allowed to proceed at 23° C.–26° C. from 5–60 minutes. After the inoculation period, the remaining Agrobacterium cells are removed from the explants by using the in-house vacuum equipment. A piece of sterile Whatman No. 1 filter paper (to fit the size of the petri plate) is placed in each of 60×15 or 60×20 mm petri dishes. Two hundred μl of sterile water is placed in the middle of the filter paper. After 2–3 minutes, the inoculated immature embryos are placed in the plates. Usually, 20–50 explants are grouped as one stack (about 1 cm in size and 60–80 mg/stack), with 4–5 stacks on each plate. The plates are immediately covered with Parafilm® and then co-cultivated in the dark at 24° C.–26° C. for 2–3 days.

The co-cultivated PCIEs are transferred CM4C+500 mg/l carbenicillin medium (delay medium) at dark. After 7 days on the delay medium, the immature embryos are transferred to CM4C supplemented with 2 mM glyphosate (not Roundup formulation) and 500 mg/l carbenicillin for selection for one week. Then calli are transferred to MMSO.2C+ 0.1 mM glyphosate (not Roundup® formulation)+250 mg/l carbenicillin medium for 2 weeks under light for further selection. Embryogenic calli are transferred to a second regeneration medium MMSOC with lower glyphosate (not Roundup® formulation) concentration (0.02 mM) and 500 mg/L carbenicillin for plant regeneration. Those embryogenic calli are transferred onto fresh medium every two week. Regenerated plantlets are transferred to Sundae cups (Sweetheart Cup Company, Chicago, Ill.) containing the second regeneration medium for further growth and selection. When roots are well established from transgenic plants, the plants are transferred to soil for further evaluation.

The evaluation of transgenic plant tolerance to glyphosate was conducted on the R0 transgenic plants. Glyphosate is administered through the use of a linear track sprayer set to deliver a 64 oz./A rate of glyphosate. Plants are sprayed once or twice. Vegetative tolerance to the glyphosate is visually evaluated a week after spray based on a scale of 0 to 5 (0=No observable/vegetative effect of glyphosate; 1=Chlorosis observed; 2=Advanced chlorosis, minor necrosis; 3=Advanced chlorosis, moderate necrosis; 4=Advanced chlorosis, severe necrosis; 5=No live tissue remaining). The $R_0$ plants produced are allowed to self, and fertility rated as a percent of unsprayed check plants. Plants that show vegetative tolerance and greater than or equal to 80% fertility are advanced to a screen of the $R_1$ progeny using spray applications of glyphosate and the rating system as described for the $R_0$ screen. The efficacy of a promoter is evaluated by this method. Effective transgenic tolerance to glyphosate herbicide and other systemic herbicides is often a function of the constitutive nature of the promoter expression pattern. In the promoter evaluation shown in Table 3, the percentage of the plants produced that show vegetative and reproductive tolerance is a measure of the utility of the promoter for constitutive expression. The promoters P-Zm.700343485, and P-Zm.70015443, in combination with a P-CaMV.35S expression cassette, demonstrated an increase in the vegetative and reproductive tolerance of transgenic wheat plants to glyphosate herbicide. P-Zm.700342364 showed an increase in vegetative tolerance, however, a reduction in the reproductive tolerance was observed. P-Zm.700164347 as a single expression cassette promoter was effective in conferring vegetative and fertility tolerance to transgenic wheat plants. These promoters in combination with regulatory elements of the expression cassette different than those tested in these demonstrations, such as, introns, leaders, transit peptides and 3' untranslated terminator regions can further express desirable expression patterns that can be selected from by those skilled in the art of plant science. For example, as shown in Table 3, transgenic glyphosate tolerant plant lines can be selected at a higher frequency that demonstrate both vegetative and reproductive tolerance when the CaMV.35S promoter is operably linked to the Os.Act1 intron compared to the Zm.Hsp70 intron. These promoters are effective for use in producing herbicide tolerance crop plants, they are as well useful for the expression of insect resistance genes, disease resistance genes, stress resistance genes and yield traits, which is an aspect of this invention.

TABLE 3

Transgenic Wheat R0 Spray Results

| pMON # | Promoter Elements | #R0 Plants | Vegetative Tolerance | >=80% Fertility | % Plants Advanced |
|---|---|---|---|---|---|
| 42411 | P-CaMV.35S/ I-Zm.Hsp70 | 71 | 26 (37%) | 1 (4%) | 1 |
| 42410 | P-CaMV.35S/ I-Os.Act1 | 150 | 78 (52%) | 38 (49%) | 25 |
| 30167 | P-Os.Act/ I-Os.Act1 | 63 | 4 (6%) | 2 (50%) | 3 |
| 45360 | P-Zm.700343485 P-CaMV.35S | 25 | 20 (80%) | 14 (70%) | 56 |
| 45361 | P-Zm.70015443 P-CaMV.35S | 26 | 22 (85%) | 20 (91%) | 77 |
| 45362 | P-Zm.700342364 P-CaMV.35S | 23 | 14 (61%) | 5 (36%) | 22 |
| 43623 | P-Zm.700164347 | 166 | 95 (57%) | 20 (21%) | 12 |

Example 7

Identification of Cis Acting Elements

Cis acting regulatory elements necessary for proper promoter regulation can be identified by a number of means. In one method, deletion analysis is carried out to remove regions of the promoter and the resulting promoter fragments are assayed for promoter activity. DNA fragments are considered necessary for promoter regulation if the activity of the truncated promoter is altered compared to the original promoter fragment. Through this deletion analysis, small regions of DNA can be identified which are necessary for positive or negative regulation of transcription. Promoter sequence motifs can also be identified and novel promoters engineered to contain these cis elements for modulating expression of operably linked transcribable sequences. See for example U.S. Pat. No. 5,223,419, herein incorporated by reference in its entirety, U.S. Pat. No. 4,990,607 herein incorporated by reference in its entirety, and U.S. Pat. No. 5,097,025 herein incorporated by reference in its entirety.

An alternative approach is to look for similar sequences between promoters with similar expression profiles. Promoters with overlapping patterns of activity can have common regulatory mechanisms. Several computer programs can be used to identify conserved, sequence motifs between promoters, including but not limited to MEME, SIGNAL SCAN, or GENE SCAN. These motifs can represent binding sites for transcriptions factors which act to regulate the promoters. Once the sequence motifs are identified, their function can be assayed. For example, the motif sequences can be deleted from the promoter to determine if the motif is necessary for proper promoter function. Alternatively, the motif can be added to a minimal promoter to test whether it is sufficient to activate transcription. Suspected negative regulatory elements can be tested for sufficiency by adding to an active promoter and testing for a reduction in promoter activity. Some cis acting regulatory elements may require other elements to function. Therefore, multiple elements can be tested in various combinations by any number of methods known to those of skill in the art.

Once functional promoter elements have been identified, promoter elements can be modified at the nucleotide level to affect protein binding. The modifications can cause either higher or lower affinity binding which would affect the level of transcription from that promoter.

Promoter elements can act additively or synergistically to affect promoter activity. In this regard, promoter elements from different 5' regulatory regions can be placed in tandem to obtain a promoter with a different spectrum of activity or different expression profile. Accordingly, combinations of promoter elements from heterologous sources or duplication of similar elements or the same element can confer a higher level of expression of operably linked transcribable sequences. For example, a promoter element can be multimerized to increase levels of expression specifically in the pattern affected by that promoter element. The technical methods needed for constructing expression vectors containing the novel engineered 5' regulatory elements are known to those of skill in the art. The engineered promoters are tested in expression vectors and tested transiently by operably linking the novel promoters to a suitable reporter gene such as GUS and testing in a transient plant assay. The novel promoters are operably linked to one or more genes of interest and incorporated into a plant transformation vector along with one or more additional regulatory elements and transformed into a target plant of interest by a suitable DNA delivery system. The stably transformed plants and subsequent progeny are evaluated by any number of molecular, immunodiagnostic, biochemical, phenotypic, or field methods suitable for assessing the desired agronomic characteristic(s).

Having illustrated and described the principles of the present invention, it should be apparent to persons skilled in the art that the invention can be modified in arrangement and detail without departing from such principles. We claim all modifications that are within the spirit and scope of the appended claims.

All publications and published patent documents cited in this specification are incorporated herein by reference to the same extent as if each individual publication or patent application is specifically and individually indicated to be incorporated by reference.

We claim:

1. An isolated DNA molecule comprising a polynucleotide of SEQ ID NO:73, or consisting of a fragment of the sequence of SEQ ID NO:73 having at least 30 nucleotides.

2. An isolated DNA molecule consisting of the isolated DNA molecule of claim 1 linked to a second polynucleotide molecule.

3. The isolated DNA molecule of claim 2, wherein the polynucleotide confers expression of said second polynucleotide molecule in transgenic plant tissue.

4. The isolated DNA molecule of claim 2, wherein the polynucleotide is a hybrid promoter.

5. The isolated DNA molecule of claim 4, further comprising a minimal promoter sequence.

6. An isolated DNA construct comprising an isolated polynucleotide of SEQ ID NO:73, or consisting of a fragment of the sequence of SEQ ID NO:73 having at least 30 nucleotides, wherein said isolated DNA construct is operably linked to a second polynucleotide and a 3' non-translated region.

7. A plant cell comprising the isolated DNA construct of claim 6.

* * * * *